US006921644B2

(12) United States Patent
Duan et al.

(10) Patent No.: US 6,921,644 B2
(45) Date of Patent: Jul. 26, 2005

(54) FOLLISTATIN-3

(75) Inventors: D. Roxanne Duan, Bethesda, MD (US); Steven M. Ruben, Olney, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 458 days.

(21) Appl. No.: 10/101,392

(22) Filed: Mar. 20, 2002

(65) Prior Publication Data

US 2002/0164714 A1 Nov. 7, 2002

Related U.S. Application Data

(62) Division of application No. 09/141,027, filed on Aug. 27, 1998, now Pat. No. 6,372,454.
(60) Provisional application No. 60/056,248, filed on Aug. 29, 1997.

(51) Int. Cl.[7] .......................... C07K 16/24; C12N 5/12; G01N 33/53; G01N 33/567
(52) U.S. Cl. .................. 435/7.1; 530/387.9; 530/388.1; 530/387.3; 530/388.15; 530/388.23; 530/389.2; 435/325; 435/326; 435/328; 435/331; 435/335
(58) Field of Search ......................... 435/7.1, 325, 326, 435/328, 331, 335; 530/387.1, 387.9, 388.1, 387.3, 388.15, 388.23, 389.2; 424/1.49

(56) References Cited

U.S. PATENT DOCUMENTS 5,942,420 A 8/1999 Holtzman

FOREIGN PATENT DOCUMENTS

| | | |
|---|---|---|
| WO | WO 99/25371 | 5/1999 |
| WO | WO 99/31237 | 6/1999 |
| WO | WO 99/55865 | 11/1999 |

OTHER PUBLICATIONS

U.S. Appl. No. 09/912,292, Rosen et al., Not Yet Published.
GenBank Accession No. AA227791 Hillier et al. Wash. U.–Merck EST Proj. (Aug. 6, 1997).
GenBank Accession No. N32892 Hillier et al., Wash. U–Merck EST Proj. (Jan. 10, 1996).
GenBank Accession No. AA470722 Nat. Cancer Inst. Cancer Genome Proj.(Aug. 14, 1997).
GenBank Accession No. AA492556 Nat. Cancer Inst. Cancer Genome Proj.(Aug. 19, 1997).
GenBank Accession No. N42037 Hillier et al., Wash. U–Merck EST Proj. (Jan. 24, 1996).
GenBank Accession No. R72628 Hillier et al., Wash. U–Merck EST Proj. (Jun. 2, 1995).
GenBank Accession No. H42225 Hillier et al., Wash. U–Merck EST Proj. (Jul. 31, 1995).
GenBank Accession No. H24937 Hillier et al., Wash. U–Merck EST Proj. (Jul. 7, 1995).
GenBank Accession No. R79389 Hillier et al., Wash. U–Merck EST Proj. (Jun. 9, 1995).
GenBank Accession No. H43043 Hillier et al., Wash. U–Merck EST Proj. (Jul. 31, 1995).
GenBank Accession No. AA227956 Hillier et al., Wash. U–Merck EST Proj. (Aug. 6, 1997).
GenBank Accession No. H14559 Hillier et al., Wash. U–Merck EST Proj. (Jun. 27, 1995).
GenBank Accession No. AA470654 Nat. Cancer Inst. Cancer Genome Proj. (Aug. 14, 1997).
GenBank Accession No. H42566 Hillier et al., Wash. U–Merck EST Proj. (Jul. 31, 1995).
GenBank Accession No. R79390 Hillier et al., Wash. U–Merck EST Proj. (Jun. 9, 1995).
GenBank Accession No. R72699 Hillier et al., Wash. U–Merck EST Proj. (Jun. 2, 1995).
GenBank Accession No. AA258582 Hillier et al., Wash. U–Merck EST Proj. (Aug. 6, 1997).
GenBank Accession No. AA365825 (Apr. 21, 1997) Adams et al., Nature 377 (6547 Sup.) 3–174 (1995).
GenBank Accession No. AA020306 Mara et al., Wash. U–HHMI mouse EST Proj. (Jan. 21, 1997).
GenBank Accession No. H51168 Hillier et al., Wash. U–Merck EST Proj. (Sep. 18, 1995).
GenBank Accession No. R46195 Hillier et al., Wash. U–Merck EST Proj. (May 10, 1995).
GenBank Accession No. AA015105 Marra et al., Wash. U–HHMI mouse EST Proj. (Jan. 21, 1997).
GenBank Accession No. W18317 Marra et al., Wash. U–HHMI mouse EST Proj. (Sep. 10, 1996).
GenBank Accession No. D31566 (Feb. 8, 1995) Sudo et al., Genomics 24:276–279 (1995).
GenBank Accession No. W14649 Marra et al., Wash. U–HHMI mouse EST Proj. (Sep. 10, 1996).
GenBank Accession No. AA568792 (Aug. 22, 1997) Nat. Cancer Inst., Cancer Genome Anatomy Project.

(Continued)

*Primary Examiner*—Prema Mertz
(74) *Attorney, Agent, or Firm*—Human Genome Sciences, Inc.

(57) ABSTRACT

The present invention relates to a novel follistatin-3 protein which is a member of the family of inhibin-related proteins. In particular, isolated nucleic acid molecules are provided encoding the human follistatin-3 protein. Follistatin-3 polypeptides are also provided as are vectors, host cells and recombinant methods for producing the same. The invention further relates to screening methods for identifying agonists and antagonists of follistatin-3 activity. Also provided are diagnostic methods for detecting reproductive system-related disorders and disorders of the regulation of cell growth and differentiation and therapeutic methods for treating reproductive system-related disorders and disorders of the regulation of cell growth and differentiation.

91 Claims, 5 Drawing Sheets

OTHER PUBLICATIONS

Hayette et al. "FLRG (follistatin–related gene), a new target of chromosomal rearrangement in malignant blood disorders" Oncogene 16:2949–2954 (1998).

Shimasaki et al., "Primary structure of the human follistatin precursor and its genomic organization" PNAS 85:4218–4222 (1988).

Online Database, Accession No. AA421522, Hillier et al., "Homo sapiens cDNA clone" (May 19, 1997).

European Search Report, Application No. EP 98 94 1072.5, dated Jul. 25, 2000.

European Search Report, Application No. PCT/US00/19198, dated Nov. 14, 2000.

Mikayama et al., PNAS 90:10056–10060 (1993).

Voet et al., John Wiley and Sons, Inc. pp. 126–128 and 228–234 (1990).

Hemmati–Briuanlou et al., Cell 77:283–295 (1994).

Genbank Accession No. N52331, Hillier et al., (Jan. 30, 1997), Genome Res., 6(9):807–828 (Jan. 30, 1997)**.

Genbank Accession No. AA552990, National Cancer Insitute, Cancer Genome Anatomy Project (Aug. 11, 1997)**.

Genbank Accession No. N28854, Hillier et al., The WashU–Merck EST Project (Jan. 4, 1996)**.

Genbank Accession No. R74502, Hillier et al., The WashU–Merck EST Project (Jun. 5, 1995)**.

Genbank Accession No. N75101. Hillier et al., (Jan. 30, 1997), Genome Res., 6(9):807–828 (Jan. 30, 1997)**.

Genbank Accession No. AC004156, Lamerdin et al., Sequence analysis of a 3.5 Mb contig in human 19p13,3 containing a sanne protease gene cluster (Feb. 19, 1998)**.

Genbank Accession No. AA975541, Adams et al., (Apr. 21, 1997). Nature 377(6547 Suppl):3–174 (1995)**.

Genbank Accession No. AA369965, Adams et al., (Apr. 21, 1997), Nature Genet., 4:373–380 (1993)**.

Genbank Accession No. AC004156 Lamerdin et al., "Homo sapiens chromosome 19, cosmid R33586"(Feb. 19, 1998)**.

Figure 1A
Follistatin-3

```
  1  GCCGTCTCTGCGTTCGCCATGCGTCCCGGGGCGCCAGGGCCACTCTGGCCTCTGCCCTGG   60
  1                    M R P G A P G P L W P L P W                     14

 61  GGGGCCCTGGCTTGGGCCGTGGGCTTCGTGAGCTCCATGGGCTCGGGGAACCCCGCGCCC  120
 15  G A L A W A V G F V S S M G S G N P A P                           34

121  GGTGGTGTTTGCTGGCTCCAGCAGGGCCAGGAGGCCACCTGCAGCCTGGTGCTCCAGACT  180
 35  G G V C W L Q Q G Q E A T C S L V L Q T                           54

        *                                                  #
181  GATGTCACCCGGGCCGAGTGCTGTGCCTCCGGCAACATTGACACCGCCTGGTCCAACCTC  240
 55  D V T R A E C C A S G N I D T A W S N L                           74

241  ACCCACCCGGGGAACAAGATCAACCTCCTCGGCTTCTTGGGCCTTGTCCACTGCCTTCCC  300
 75  T H P G N K I N L L G F L G L V H C L P                           94

301  TGCAAAGATTCGTGCGACGGCGTGGAGTGCGGCCCGGGCAAGGCGTGCCGCATGCTGGGG  360
 95  C K D S C D G V E C G P G K A C R M L G                          114

361  GGCCGCCCGCGCTGCGAGTGCGCGCCCGACTGCTCGGGGCTCCCGGCGCGGTTGCAGGTC  420
115  G R P R C E C A P D C S G L P A R L Q V                          134

                         *
421  TGCGGCTCAGACGGCGCCACCTACCGCGACGAGTGCGAGCTGCGCGCCGCGCGCTGCCGC  480
135  C G S D G A T Y R D E C E L R A A R C R                          154

481  GGCCACCCGGACCTGAGCGTCATGTACCGGGGCCGCTGCCGCAAGTCCTGTGAGCACGTG  540
155  G H P D L S V M Y R G R C R K S C E H V                          174

541  GTGTGCCCGCGGCCACAGTCGTGCGTCGTGGACCAGACGGGCAGCGCCCACTGCGTGGTG  600
175  V C P R P Q S C V V D Q T G S A H C V V                          194

601  TGTCGAGCGGCGCCCTGCCCTGTGCCCTCCAGCCCCGGCCAGGAGCTTTGCGGCAACAAC  660
195  C R A A P C P V P S S P G Q E L C G N N                          214

     #
661  AACGTCACCTACATCTCCTCGTGCCACATGCGCCAGGCCACCTGCTTCCTGGGCCGCTCC  720
215  N V T Y I S S C H M R Q A T C F L G R S                          234

                                         *
721  ATCGGCGTGCGCCACGCGGGCAGCTGCGCAGGCACCCCTGAGGAGCCGCCAGGTGGTGAG  780
235  I G V R H A G S C A G T P E E P P G G E                          254

     *
781  TCTGCAGAAGAGGAAGAGAACTTCGTGTGAGCCTGCAGGACAGGCCTGGGCCTGGTGCCC  840
255  S A E E E E N F V                                                263
```

Figure 1B
*Follistatin-3*

```
 841  GAGGCCCCCCATCATCCCCTGTTATTTATTGCCACAGCAGAGTCTAATTTATATGCCACG   900
 901  GACACTCCTTAGAGCCCGGATTCGGACCACTTGGGGATCCCAGAACCTCCCTGACGATAT   960
 961  CCTGGAAGGACTGAGGAAGGGAGGCCTGGGGGCCGGCTGGTGGGTGGGATAGACCTGCGT  1020
1021  TCCGGACACTGAGCGCCTGATTTAGGGCCCTTCTCTAGGATGCCCCAGCCCCTACCCTAA  1080
1081  GACCTATTGCCGGGGAGGATTCCACACTTCCGCTCCTTTGGGGATAAACCTATTAATTAT  1140
1141  TGCTACTATCAAGAGGGCTGGGCATTCTCTGCTGGTAATTCCTGAAGAGGCATGACTGCT  1200
1201  TTTCTCAGCCCCAAGCCTCTAGTCTGGGTGTGTACGGAGGGTCTAGCCTGGGTGTGTACG  1260
1261  GAGGGTCTAGCCTGGGTGAGTACGGAGGGTCTAGCCTGGGTGAGTACGGAGGATCTAGCC  1320
1321  TGGGTGAGTACGGAGAGTCTAGCCTGGGTGTGTATGGAGGATCTAGCCTGGGTGAGTATG  1380
1381  GAGGGTCTAGCCTGGGTGAGTATGGAGGGTCTAGCCTGGGTGTGTATGGAGGGTCTAGCC  1440
1441  TGGGTGAGTATGGAGGGTCTAGCCTGGGTGTGTATGGAGGGTCTAGCCTGGGTGAGTATG  1500
1501  GAGGGTCTAGCCTGGGTGTGTACGGAGGGTCTAGTCTGAGTGCGTGTGGGGACCTCAGAA  1560
1561  CACTGTGACCTTAGCCCAGCAAGCCAGGCCCTTCATGAAGGCCAAGAAGGCTGCCACCAT  1620
1621  TCCCTGCCAGCCCAAGAACTCCAGCTTCCCCACTGCCTCTGTGTGCCCCTTTGCGTCCTG  1680
1681  TGAAGGCCATTGAGAAATGCCCAGTGTGCCCCCTGGGAAAGGGCACGGCCTGTGCTCCTG  1740
1741  ACACGGGCTGTGCTTGGCCACAGAACCACCCAGCGTCTCCCCTGCTGCTGTCCACGTCAG  1800
1801  TTCATGAGGCAACGTCGCGTGGTCTCAGACGTGGAGCAGCCAGCGGCAGCTCAGAGCAGG  1860
1861  GCACTGTGTCCGGCGGAGCCAAGTCCACTCTGGGGGAGCTCTGGCGGGGACCACGGGCCA  1920
1921  CTGCTCACCCACTGGCCCCGAGGGGGGTGTAGACGCCAAGACTCACGCATGTGTGACATC  1980
1981  CGGAGTCCTGGAGCCGGGTGTCCCAGTGGCACCACTAGGTGCCTGCTGCCTCCACAGTGG  2040
```

Figure 1C
Follistatin-3

```
2041  GGTTCACACCCAGGGCTCCTTGGTCCCCCACAACCTGCCCCGGCCAGGCCTGCAGACCCA  2100

2101  GACTCCAGCCAGACCTGCCTCACCCACCAATGCAGCCGGGGCTGGCGACACCAGCCAGGT  2160

2161  GCTGGTCTTGGGCCAGTTCTCCCACGACGGCTCACCCTCCCCTCCATCTGCGTTGATGCT  2220

2221  CAGAATCGCCTACCTGTGCCTGCGTGTAAACCACAGCCTCAGACCAGCTATGGGGAGAGG  2280

2281  ACAACACGGAGGATATCCAGCTTCCCCGGTCTGGGGTGAGGAGTGTGGGGAGCTTGGGCA  2340

2341  TCCTCCTCCAGCCTCCTCCAGCCCCCAGGCAGTGCCTTACCTGTGGTGCCCAGAAAAGTG  2400

2401  CCCCTAGGTTGGTGGGTCTACAGGAGCCNCAGCCAGGCAGCCCACCCCACCCTGGGGCCC  2460

2461  TGCCTCACCAAGGAAATAAAGACTCAAAGAAGCCT  2495
```

Figure 2

Percent Similarity: 61.508 Percent Identity: 43.254

Follistatin3.aa
x
Follistatin1.aa

```
                   .         .         .         .         .
  7 GPLWPLPWGALAWAVGFVSSMGSGNPAPGGVCWLQQGQEATCSLVLQTDV 56
    .. :. | |:|.: : ::: : .:..|.:| |||.|:.:: | :::..|::
  2 VRARHQP.GGLCLLLLLLLCQFMEDRSAQAGNCWLRQAKNGRCQVLYKTEL 50

                   .         .         .         .         .
 57 TRAECCASGNIDTAWSNLTHPGNKINLLGFL....GLVHCLPCKDSCDGV 102
    .:.|||..|.:.|.|.:  ...|. .|: ::     | .:|:|||:.|:.|
 51 SKEECCSTGRLSTSWTE..EDVNDNTLFKWMIFNGGAPNCIPCKETCENV 98

                   .         .         .         .         .
103 ECGPGKACRM.LGGRPRCECAPDCSGLPARLQVCGSDGATYRDECELRAA 151
    :|||||  |||    .:||| ||||||.:. : .||| || |||:||.|   |
 99 DCGPGKKCRMNKKNKPRCVCAPDCSNITWKGPVCGLDGKTYRNECALLKA 148

                   .         .         .         .         .
152 RCRGHPDLSVMYRGRCRKSCEHVVCPRPQSCVVDQTGSAHCVVCRAAPCP 201
    ||:::|:|.| |.|||:|.| .|.|| . .||||||..|.||.|.    ||
149 RCKEQPELEVQYQGRCKKTCRDVFCPGSSTCVVDQTNNAYCVTCNRI.CP 197

                   .         .         .         .         .
202 VPSSPGQELCGNNNVTYISSCHMRQATCFLGRSIGVRHAGSC..AGTPEE 249
     |.|.:| ||||:.||| |.||:|.|||:|||||||: ..|.|  | ..|:
198 EPASSEQYLCGNDGVTYSSACHLRKATCLLGRSIGLAYEGKCIKAKSCED 247

                   .
250 PPGGESAEEEENF 262
     ...:: .   :|
248 IQCTGGKKCLWDF 260
```

Follistatin-3

FOLLISTATIN-3

This application is a divisional of U.S. application Ser. No. 09/141,027, filed Aug. 27, 1998 (now U.S. Pat. No. 6,372,454), which claims benefit under 35 U.S.C §119(e) of U.S. Provisional Application Ser. No. 60/056,248, filed Aug. 29, 1997, which is hereby incorporated by reference in its entirety.

FIELD OF THE INVENTION

The present invention relates to a novel human gene encoding a polypeptide which is a member of the family of inhibin-related proteins. More specifically, isolated nucleic acid molecules are provided encoding a human polypeptide named follistatin-3. Follistatin-3 polypeptides are also provided, as are vectors, host cells and recombinant methods for producing the same. Also provided are diagnostic methods for detecting disorders related to the reproductive system, and therapeutic methods for treating such disorders. The invention further relates to screening methods for identifying agonists and antagonists of follistatin-3 activity.

BACKGROUND OF THE INVENTION

The family of inhibin-related proteins currently consists of at least four groups of members: inhibins, activins, and two splice variants of follistatin-1 (315 and 288 amino acids). Inhibins and activins are members of the transforming growth factor (TGF)-β superfamily and function with opposing actions in a variety of capacities in paracrine and autocrine regulation of both-reproductive and nonreproductive organs including the liver, kidney, adrenal glands, bone marrow, placenta, anterior pituitary, and brain (Ying, S. Y., et al., *Proc. Soc. Exp. Biol. Med.* 214:114–122 (1997); Mather, J. P., et al., *Proc. Soc. Exp. Biol. Med.* 215:209–222 (1997)). Although the follistatins are not closely related to the TGF-β family, they still play a major role in the follical stimulating hormone (FSH) synthetic pathway by increasing estradiol production and by functioning directly as high affinity activin-binding proteins. Inhibins, activins, and follistatin-1 were all initially identified as regulators of pituitary FSH secretion, but have more recently been further characterized to function as growth factors, embryo modulators, and immune factors (Petraglia, F. Placenta 18:3–8 (1997)). In addition, each of these factors is involved with the regulation of gonadotropin biosynthesis and secretion, ovarian and placental steroidogenesis, and oocyte and spermatogonial maturation (Halvorson, L. M. and DeCherney, A. H. *Fertil. Steril.* 65:459–469 (1996)).

FSH is a vital component of the regulatory cascade governing development of human oocytes. Primary oocytes in newborns are arrested in the prophase stage of Meiosis I and are surrounded by a 1–2 cell thick layer of follicle cells constituting a structure termed the primordial follicle. In concert with other factors, stimulation of the primordial follicle with FSH initiates its progression to the more complex structures designated the developing and antral follicles (Ueno, N., et al., *Proc. Natl. Acad. Sci. USA* 84:8282–8286 (1987); Robertson, D. M., et al., *Biochem. Biophys. Res. Comm.* 149:744–749 (1987)). The antral follicle consists of an enlarged oocyte surrounded by an increased number of follicle cells, a zona pellucida, cortical granules, and a fluid-filled cavity termed the antrum. It is in this state that thousands of developing oocytes are maintained until puberty. Each month following this point, a surge in the local concentration of several additional hormones and other factors, primarily leuteinizing hormone (LH), stimulates accelerates the growth of roughly 15–20 of the developing follicles in the ovary. Only one of these structures will ultimately complete the developmental progression of its enclosed oocyte to the metaphase stage of Meiosis II. The single stimulated follicle will then continue to enlarge until it bursts at the surface of the ovary and releases the oocyte, still surrounded with a coating of follicle cells, for potential fertilization (Boruslaeger, E. A., et al., *Dev. Biol.* 114:453–462 (1986); Masui, Y. and Clarke, H. *J. Int. Rev. Cytol.* 57:185–282 (1979); Richards, J. S. *Recent Prog. Horm. Res.* 35:343–373 (1979)).

Follistatin also plays a central role in the above-described process of follicle development. Follistatin binds stoichiometrically to activins and, as a result, inhibits the activin-induced augmentation of FSH-release from cultured pituitary cells (Kogawa, K., et al., *Endocrinology* 128:1434–1440 (1991)). Further evidencing a feedback mechanism, cultured granulosa cells produce and secrete follistatin in response to treatment with FSH (Saito, S., et al., *Biochem. Biophys. Res. Comm.* 176:413–422 (1991); Klein, R., et al., *Endocrinology* 128:1048–1056 (1991)). Furthermore, it has been determined by synthesizing the results of a number of studies, that follistatin, activin, FSH, LH, and other factors function in concert in a variety of interrelated mechanisms to regulate many developmental processes, including the development of follicles. For example, in the presence of FSH, activin can augment both LH receptor expression and progesterone production by rat granulosa cells (Sugino, H., et al., *Biochem. Biophys. Res. Comm.* 153:281–288 (1988)). In addition, activin can significantly enhance the ability of granulosa cells to express FSH receptor and produce inhibin even in the absence of FSH (Nakamura, T., et al., *Biochim. Biophys. Acta* 1135:103–109 (1992); Sugino, H., et al., supra; Hasegawa, Y., et al., *Biochem. Biophys. Res. Comm.* 156:668–674 (1988)). These and other studies provide support for the idea that follistatin and activin play important roles in the regulation of granulosa cellular differentiation.

In addition to the many well-characterized effects which follistatin, activin, and inhibin elicit on the regulation of various developmental processes in the reproductive system, a large number of studies have more recently begun to define regulatory roles for these molecules in a variety of other tissues and systems. For example, during early embryonic development in Xenoptus laevis, the action of activin A in developing targets of ciliary ganglion neurons is regulated by localized expression of follistatin (Hemmati-Brivanlou, A. and Melton, D. A. *Nature* 359:609–614 (1992); Hemmati-Brivanlou, A. and Melton, D. A. *Cell* 77:273–281 (1994)). In addition, overexpression of follistatin leads to induction of neural tissue (Hemmati-Brivanlou, A., et al., *Cell* 77:283–295 (1994)). In the mouse, follistatin mRNA is first detected on embryonic day 5.5 in the deciduum, and, subsequently, in the developing hindbrain, somites, vibrissae, teeth, epidermis, and muscle (van den Eihnden-van Raaij, A. J. M., et al., *Dev. Biol.* 154:356–365 (1992); Albano, R. M., et al., *Development* 120:803–813 (1994); Feijen, A., et al., *Development* 120:3621–3637 (1994)). Evidence of the relative importance of such a varied expression of follistatin is provided by Matzuk and colleagues (*Nature* 374:360–363 (1995)) who demonstrate that follistatin-deficient mice are retarded in their growth, have decreased mass of the diaphragm and intercostal muscles, shiny taut skin, skeletal defects of the hard palate and the thirteenth pair of fibs, their whisker and tooth development is abnormal, they fail to breathe, and die within hours of birth. Since the defects in mice deficient in follistatin are far more widespread than in mice deficient in activin, Matzuk and coworkers (supra) suggest that follistatin may modulate the cell growth and differentiation regulatory actions of additional members of the TGF-β superfamily.

Thus, there is a need for polypeptides that function as regulators of reproductive development, embryonic development, and cell growth and differentiation since disturbances of such regulation may be involved in disorders relating to reproduction and the regulation of cell growth and differentiation. Therefore, there is a need for identification and characterization of such human polypeptides which can play a role in detecting, preventing, ameliorating or correcting such disorders.

SUMMARY OF THE INVENTION

The present invention provides isolated nucleic acid molecules comprising a polynucleotide encoding at least a portion of the follistatin-3 polypeptide having the complete amino acid sequence shown in SEQ ID NO:2 or the complete amino acid sequence encoded by the cDNA clone deposited as plasmid DNA as ATCC® Deposit Number 209197 on Aug. 8, 1997. The nucleotide sequence determined by sequencing the deposited follistatin-3 clone, which is shown in FIGS. 1A, 1B, and 1C (SEQ ID NO:1), contains a open reading frame encoding a complete polypeptide of 263 amino acid residues, including an initiation codon encoding an N-terminal methionine at nucleotide positions 19–21, and a predicted molecular weight of about 27.7 kDa. Nucleic acid molecules of the invention include those encoding the complete amino acid sequence excepting the N-terminal methionine shown in SEQ ID NO:2, or the complete amino acid sequence excepting the N-terminal methionine encoded by the cDNA clone in ATCC® Deposit Number 209197, which molecule also can encode additional amino acids fused to the N-terminus of the follistatin-3 amino acid sequence.

The encoded polypeptide has a predicted leader sequence of 26 amino acids underlined in FIG. 1A; and the amino acid sequence of the predicted mature follistatin-3 protein is also shown in FIGS. 1A, 1B, and 1C, as amino acid residues 27–263 and as residues 1–237 in SEQ ID NO:2.

Thus, one aspect of the invention provides an isolated nucleic acid molecule comprising a polynucleotide comprising a nucleotide sequence selected from the group consisting of: (a) a nucleotide sequence encoding the follistatin-3 polypeptide having the complete amino acid Sequence in SEQ ID NO:2 (i.e., positions −26 to 237 of SEQ ID NO.2), (b) a nucleotide sequence encoding the follistatin-3 polypeptide having the complete amino acid sequence in SEQ ID NO:2 excepting the N-terminal methionine (i.e., positions −25 to 237 of SEQ ID NO:2); (c) a nucleotide sequence encoding the predicted mature follistatin-3 polypeptide having the amino acid sequence at positions 1 to 237 in SEQ ID NO:2; (d) a nucleotide sequence encoding the follistatin-3 polypeptide having the complete ammo acid sequence encoded by the cDNA clone contained in ATCC® Deposit No. 209197; (e) a nucleotide sequence encoding the follistatin-3 polypeptide having the complete amino acid sequence excepting the N-terminal methionine encoded by the cDNA clone contained in ATCC® Deposit No. 209197; (I a nucleotide sequence encoding the mature follistatin-3 polypeptide having the amino acid sequence encoded by the cDNA clone contained in ATCC® Deposit No. 209197; and (g) a nucleotide sequence complementary to any of the nucleotide Sequences in (a), (b), (c), (d), (e) or (f) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e), .(f) or (g), above, or a polynucleotide which hybridizes under stringent hybridization conditions to a polynucleotide in (a), (b), (c), (d), (e), (f) or (g), above. This polynucleotide which hybridizes does not hybridize under stringent hybridization conditions to a polynucleotide having a nucleotide sequence consisting of only A residues or of only T residues.

An additional nucleic acid embodiment of the invention relates to an isolated nucleic acid molecule comprising a polynucleotide which encodes the amino acid sequence of an epitope-bearing portion of a follistatin-3 polypeptide having an amino acid sequence in (a), (b), (c), (d), (e) or (f), above. A further embodiment of the invention relates to an isolated nucleic acid molecule comprising a polynucleotide which encodes the amino acid sequence of a follistatin-3 polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polynucleotide which encodes the amino acid sequence of a follistatin-3 polypeptide to have an amino acid sequence which contains not more than 10, 9, 8, 7, 6, 5, 4, 3, 2 or 1 amino acid substitutions. Conservative substitutions are preferable.

The present invention also relates to recombinant vectors, which include the isolated nucleic acid molecules of the present invention; and to host cells containing the recombinant vectors, as well as to methods of making such vectors and host cells and for using them for production of follistatin-3 polypeptides or peptides by recombinant techniques.

In accordance with a further aspect of the present invention, there is provided a process for producing such polypeptide by recombinant techniques comprising culturing recombinant prokaryotic and/or eukaryotic host cells, containing a follistatin-3 nucleic acid sequence, under conditions promoting expression of said protein and subsequent recovery of said protein.

The invention further provides in isolated follistatin-3 polypeptide comprising: an amino acid sequence selected from the group consisting of: (a) tie amino acid sequence of the full-length follistatin-3 polypeptide having the complete amino acid sequence shown in SEQ ID NO:2 (i.e., positions −26 to 237 of SEQ ID NO:2); (b) the amino acid sequence of the full-length follistatin-3 polypeptide having the complete amino acid sequence shown in SEQ ID NO:2 excepting the N-terminal methionine (i.e., positions −25 to 237 of SEQ ID NO:2); (c) the amino acid sequence of the predicted mature follistatin-3 polypeptide having the amino acid sequence at positions 1 to 237 in SEQ ID NO:2; (d) the amino acid sequence of the full-length follistatin-3 polypeptide having the complete amino acid sequence encoded by the cDNA clone contained in ATCC® Deposit No. 209197; (e) the amino acid sequence of the full-length follistatin-3 polypeptide having the complete amino acid sequence excepting the N-terminal methionine encoded by the cDNA clone contained in ATCC® Deposit No. 209197; and (f) the amino acid sequence of the mature follistatin-3 polypeptide having the amino acid sequence encoded by the cDNA clone contained in ATCC® Deposit No.209197. The polypeptides of the present invention also include polypeptides having an amino acid sequence at least 80% identical, more preferably at least 90% identical, and still more preferably 95%, 96%, 97%, 98% or 99% identical to those described in (a), (b), (c), (f), (e) or (0 above, as well as polypeptides having an amino acid sequence with at least 90% similarity, and more preferably at least 95% similarity, to those above.

An additional embodiment of this aspect of the invention relates to a peptide or polypeptide which comprises the amino acid sequence of an epitope-bearing portion of a follistatin-3 polypeptide having an amino acid sequence described in (a), (b), (c), (d), (e) or (f) above. Peptides or polypeptides having the amino acid sequence of an epitope-bearing portion of a follistatin-3 polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

A further embodiment of the invention relates to a polypeptide which comprises the amino acid sequence of a follistatin-3 polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of a follistatin-3 polypeptide, which contains at least one, but not more than 10, 9, 8, 7, 6, 5, 4, 3, 2 or 1 amino acid substitutions. In specific embodiments, the number of additions, substitutions, and/or deletions in the amino acid sequence of FIGS. 1A, 1B, and 1C, or fragments thereof (e.g., the mature form and/or other fragments described herein), is 1–5, 5–10, 5–25, 5–50, 10–50 or 50–150, conservative amino acid substitutions are preferable.

In another embodiment, the invention provides an isolated antibody that binds specifically to a follistatin-3 polypeptide having an amino acid sequence described in (a), (b), (c), (d), (e) or (f) above. The invention further provides methods for isolating antibodies that bind specifically to a follistatin-3 polypeptide having an amino acid sequence as described herein. Such antibodies are useful diagnostically or therapeutically as described below.

The invention also provides for pharmaceutical compositions comprising follistatin-3 polypeptides, particularly human follistatin-3 polypeptides, which may be employed, for instance, to treat cancers and other cellular growth and differentiation disorders, as well as disorders of the reproductive system. Methods of treating individuals in need of follistatin-3 polypeptides are also provided.

The invention further provides compositions comprising a follistatin-3 polynucleotide or a follistatin-3 polypeptide for administration to cells in vitro, to cells ex vivo and to cells in vivo, or to a multicellular organism. In certain particularly preferred embodiments of this aspect of the invention, the compositions comprise a follistatin-3 polynucleotide for expression of a follistatin-3 polypeptide in a host organism for treatment of disease. Particularly preferred in this regard is expression in a human patient for treatment of a dysfunction associated with aberrant endogenous activity of follistatin-3.

The present invention also provides a screening method for identifying compounds capable of enhancing or inhibiting a biological activity of the follistatin-3 polypeptide, which involves contacting a ligand which is inhibited by the follistatin-3 polypeptide with the candidate compound in the presence of a follistatin-3 polypeptide, assaying receptor-binding activity of the ligand in the presence of the candidate compound and of follistatin-3 polypeptide, and comparing the ligand activity to a standard level of activity, the standard being assayed when contact is made between the ligand itself in the presence of the follistatin-3 polypeptide and the absence of the candidate compound In this assay, an increase in ligand activity over the standard indicates that the candidate compound is an agonists of follistatin-3 activity and a decrease in ligand activity compared to the standard indicates that the compound is an antagonist of follistatin-3 activity.

In another aspect, a screening assay for agonists and antagonists is provided which involves determining the effect a candidate compound has on follistatin-3 binding to activin or an activin-like molecule. In particular, the method involves contacting the activin or an activin-like molecule with a follistatin-3 polypeptide and a candidate compound and determining whether follistatin-3 polypeptide binding to the activin or an activin-like molecule is increased or decreased due to the presence of the candidate compound. In this assay, an increase in binding of follistatin-3 over the standard binding indicates that the candidate compound is an agonists of follistatin-3 binding activity and a decrease in follistatin-3 binding compared to the standard indicates that the compound is an antagonist of follistatin-3 binding activity.

It has been discovered that follistatin-3 is expressed not only in Hodgkin's Lymphoma but also in synovial fibroblasts, gall bladder, resting and serum-induced smooth muscle, testes, Merkel cells, HEL cells, hippocampus, TNF-α- and IFN-induced epithelial cells, keratinocyte, amygdala depression, HL-60 cells, hepatoma, progesterone-treated epidermal cells, endothelial cells, HSC172 cells, epithelioid sarcoma, activated T-cells, breast lymph node, pancreatic carcinoma, fetal dura mater, fetal lung, epididymis, placenta, dendritic cells, rejected kidney, and uterine cancer. Therefore, nucleic acids of the invention are useful as hybridization probes for differential identification of the tissue(s) or cell type(s) present in a biological sample. Similarly, polypeptides and antibodies directed to those polypeptides are useful to provide immunological probes for differential identification of the tissue(s) or cell type(s). In addition, for a number of disorders of the above tissues or cells, particularly of the reproductive system, or disorders of the regulation of cell growth and differentiation, significantly higher or lower levels of follistatin-3 gene expression may be detected in certain tissues (e.g., cancerous and wounded tissues) or bodily fluids (e.g., serum, plasma, urine, synovial fluid or spinal fluid) taken from an individual having such a disorder, relative to a "standard" follistatin-3 gene expression level, i.e., the follistatin-3 expression level in healthy tissue from an individual not having the reproductive system or regulation of cell growth and differentiation disorder. Thus, the invention provides a diagnostic method useful during diagnosis of such a disorder, which involves: (a) assaying follistatin-3 gene expression level in cells or body fluid of an individual; (b) comparing the follistatin-3 gene expression level with a standard follistatin-3 gene expression level, whereby an increase or decrease in the assayed follistatin-3 gene expression level compared to the standard expression level is indicative of disorder in the reproductive system or of a disorder of the regulation of cell growth and differentiation.

An additional aspect of the invention is related to a method for treating an individual in need of an increased level of follistatin-3 activity in the body comprising administering to such an individual a composition comprising a therapeutically effective amount of an isolated follistatin-3 polypeptide of the invention or an agonists thereof.

A still further aspect of the invention is related to a method for treating an individual in need of a decreased level of follistatin-3 activity in the body comprising, administering to such an individual a composition comprising a therapeutically effective amount of an follistatin-3 antagonist. Preferred antagonists for use in the present invention are follistatin-3-specific antibodies.

BRIEF DESCRIPTION OF THE FIGURES

FIGS. 1A, 1B, and 1C show the nucleotide sequence (SEQ ID NO:1) and deduced amino acid sequence (SEQ ID NO:2) of follistatin-3.

Figure 3:
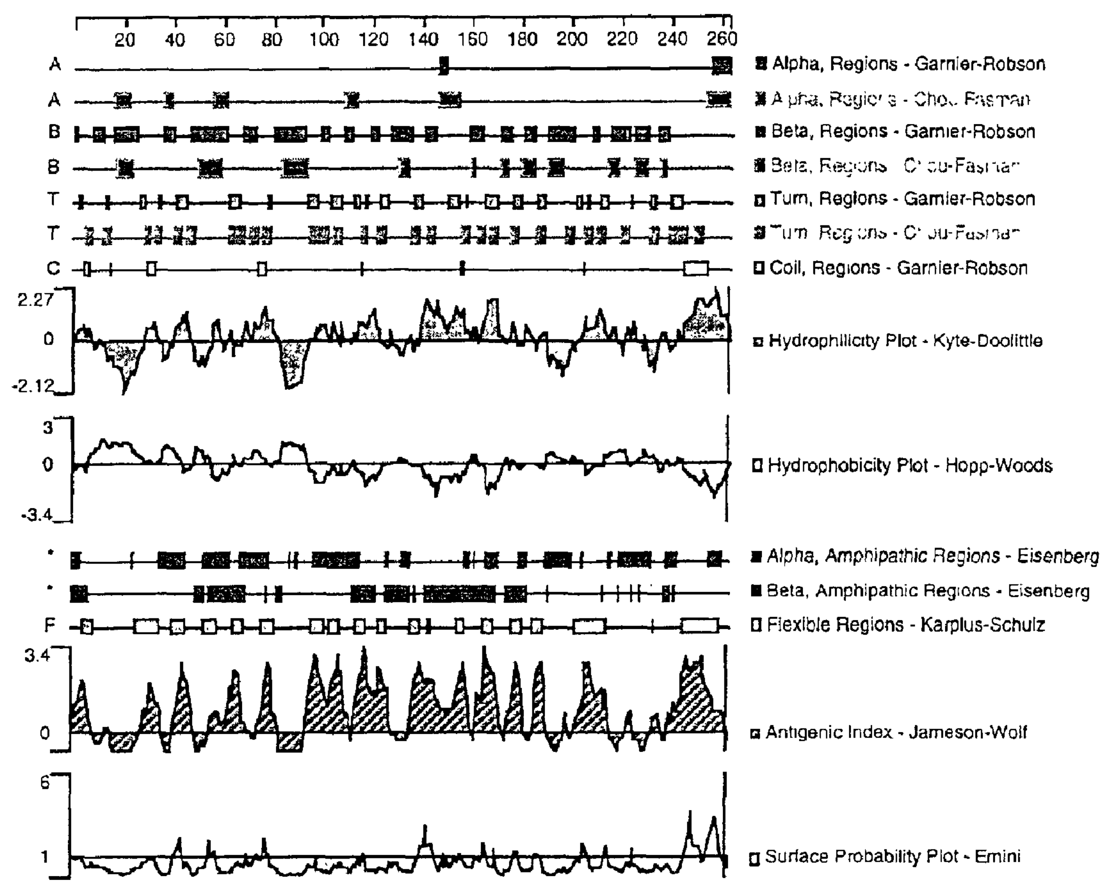

The predicted leader sequence of about 26 amino acids is underlined. Note that the methionine residue at the beginning of the leader sequence in FIG. 1A is shown in position number (positive) 1, whereas the leader positions in the corresponding sequence of SEQ ID NO:2 are designated with negative position numbers. Thus, the leader sequence positions 1 to 26 in FIG. 1A correspond to positions −26 to −1 in SEQ ID NO:2.

Two potential asparagine-linked glycosylation sites are marked in the amino acid sequence of follistatin-3. The sites are asparagine-73 and asparagine-215 in FIG. 1A (asparagine-47 and asparagine-179 in SEQ ID NO:2), and are with the bold pound symbol (#) above the nucleotide sequence coupled with a bolded one letter abbreviation for the asparagine (N) in the amino acid sequence in FIG. 1A; that is, the actual asparagine residues which are potentially glycosylated is bolded in FIG. 1A. The potential N-linked glycosylation sequences are found at the following locations in the follistatin-3 amino acid sequence: N-73 through H-76 (N-73, L-74, T-75, H-76) and N-215 through Y-218 (N-215, V-216, T-217, Y-218). A potential Protein Kinase C (PKC) phosphorylation site is also marked in FIG. 1A with a bolded tyrosine symbol (T) in the follistatin-3 amino acid sequence and an asterisk (*) above the first nucleotide encoding that tyrosine residue in the follistatin-3 nucleotide sequence. The potential PKC phosphorylation sequence is found in the follistatin-3 amino acid sequence from residue T-141 through residue R-143 (T-141, Y-142, R-143). Potential Casein Kinase II (CK2) phosphorylation sites are also marked in FIG. 1A with a bolded tyrosine or serine symbol (T or S) in the follistatin-3 amino acid sequence and an asterisk (*) above the first nucleotide encoding the appropriate tyrosine or serine residue in the follistatin-3 nucleotide sequence. Potential CK2 phosphorylation sequences are found at the following locations in the follistatin-3 amino acid sequence: T-57 through E-60 (T-57, R-58, A-59, E-60); T-141 through D-144 (T-141, Y-142, R-143, D-144); T-246 through E-249 (T-246, P-247, E-248, E-249); and S-255 through E-258 (S-255, A-256, E-257, E-258). Ten potential myristylation sites are found in the follistatin-3 amino acid sequence shown in FIG. 1A. Potential myristylation sites are marked in FIG. 1A with a double underline delineating the amino acid residues representing each potential myristolation site in the follistatin-3 amino acid sequence. The potential myristolation sites are located in the following positions in the follistatin-3 amino acid sequence: G-43 through C-48 (G-43, Q-44, E-45, A-46, T-47, C-48); G-65 through A-70 (G-65, N-66, I-67, D-68, T-69, A-70); G-78 through L-83 (G-78, N-79, K-80, 1–81, N-82, L-83); G-88 through L-93 (G-88, L-89, V-90, H-91, C-92, L-93); G-136 through T-141 (G-136, S-137, D-138, G-139, A-140, T-141); G-188 through V-193 (G-188, S-189, A-190, H-191, C-192, V-193); G-207 through G-212 (G-207, Q-208, E-209, L-210, C-211, G-212); G-236 through G-241 (G-236, V-237, R-238, H-239, A-240, G-241); G-241 through T-246 (G-241, S-242, C-243, A-244, G-245, T-246); and G-252 through E-257 (G-252, G-253, E-254, S-255, A-256, E-257).

FIG. 2 shows the regions of identity between the amino acid sequences of the follistatin-3 protein and translation product of the human mRNA for follistatin-1 (SEQ ID NO:3), determined by the computer program Bestfit (Wisconsin Sequence Analysis Package, Version 8 for Unix, Genetics Computer Group, University Research Park, 575 Science Drive, Madison, Wis. 53711) using the default parameters.

FIG. 3 shows an analysis of the follistatin-3 amino acid sequence (SEQ ID NO:2). Alpha, beta, turn and coil regions; hydrophilicity and hydrophobicity; amphipathic regions; flexible regions; antigenic index and surface probability, as predicted using default parameters of the recited computer programs, are shown.

In the "Antigenic Index or Jameson-Wolf" graph, the positive peaks indicate locations of the highly antigenic regions of the follistatin-3 protein, i.e., regions from which epitope-bearing peptides of the invention can be obtained. Non-limiting examples of antigenic polypeptides or peptides that can be used to generate follistatin-3-specific antibodies include: a polypeptide comprising amino acid residues Lys-54 to Asp-62, Val-91 to Leu-99, Lys-100 to Gln-108, Cys-116 to Pro-124, Gln-140 to Leu-148, Trp-156 to Ser-164, Arg-170 to Gln-181, Cys-212 to Phe-224, Tyr-239 to Thr-247, Pro-251 to Met-259, and Asp-263, to His-271 of SEQ ID NO:2.

The data presented in FIG. 3 are also represented in tabular form in Table I. The columns are labeled with the headings "Res", "Position", and Roman Numerals I–XIV. The column headings refer to the following features of the amino acid sequence presented in FIG. 3 and Table I: "Res": amino acid residue of SEQ ID NO:2 or FIG. 1A (which is the identical sequence shown in SEQ ID NO:2, with the exception that the residues are numbered 1–263 in FIG. 1A and −18 through 348 in SEQ ID NO:4); "Position": position of the corresponding residue within SEQ ID NO:2 or FIGS. 2A and 2B (which is the identical sequence shown in SEQ ID NO:4, with the exception that the residues are numbered 1–366 in FIGS. 2A and 2B and −18 through 348 in SEQ ID NO:4); I: Alpha, Regions—Gamier-Robson; II: Alpha, Regions—Chou-Fasman; III: Beta, Regions—Garnier-Robson; IV: Beta, Regions—Chou-Fasman; V: Turn, Regions-Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot-Hopp-Woods; X: Alpha, Amphipathic Regions—Eisenberg; XI: Beta, Amphipathic Regions—Eisenberg; XII: Flexible Regions—Karplus-Schulz; XIII: Antigenic Index-Jameson-Wolf; and XIV: Surface Probability Plot-Emini.

DETAILED DESCRIPTION

The present invention provides isolated nucleic acid molecules comprising a polynucleoticle encoding a folliStatin-3 polypeptide having the amino acid sequence shown in SEQ ID NO:2, which was determined by sequencing a cloned cDNA. The nucleotide sequence shown in FIGS. 1A. 1B, and 1C (SEQ ID NO:1) was obtained by sequencing the HDTAH85 clone, which was deposited On Aug. 2, 1997 at the American Type Culture Collection, 10801 University floulevard, Manassas, Va. 20110-2209, and given accession number ATCC® 209197. The deposared clone is conTained in the pBluescript SK(−) plasmid (Stratagene, La Jolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIGS. 1A, 1B, and 1C (SEQ ID NO:1), a nucleic acid molecule of the present invention encoding a follistatin-3 polypeptide may be obtained using standard cloning and screening procedures, such as those for cloning cDNAs using mRNA as starting material. Illustrative of the invention, the nucleic acid molecule described in FIGS. 1A, 1B, and 1C (SEQ ID NO:1) was discovered in a cDNA library derived from Hodgkin's Lymphoma.

Additional clones of the same gene were also identified in cDNA libraries from the following cells and tissues: synovial fibroblasts, gall bladder, resting and serum-induced smooth muscle, testes, Merkel cells, HEL cells, hippocampus, TNF-α- and IFN-induced epithelial cells, keratinocyte, amygdala depression, HL-60 cells, hepatoma, progesterone-treated epidermal cells, endothelial cells, HSC172 cells, epithelioid sarcoma, activated T-cells, breast lymph node, pancreatic carcinoma, fetal dura mater, fetal lung, epididymis, placenta, dendritic cells, rejected kidney, and uterine cancer.

The determined nucleotide sequence of the follistatin-3 cDNA of FIGS. 1A, 1B, and 1C (SEQ ID NO:1) contains an open reading frame encoding a protein of 263 amino acid residues, with an initiation codon at nucleotide positions 19–21 of the nucleotide sequence in FIG. 1A (SEQ ID NO:1), and a deduced molecular weight of about 27.7 kDa. The amino acid sequence of the follistatin-3 protein shown in SEQ ID NO:2 is about 43.2% identical to human mRNA for follistatin-1 (FIG. 2; Shimasaki, S., et al., *Proc. Natl. Acad. Sci. U.S.A.* 85:4218–4222 (1988); GenBank Accession No. J03771).

The open reading frame of the follistatin-3 gene shares sequence homology with the translation product of the human mRNA for follistatin-1 (FIG. 2; SEQ ID NO:3). The homology between follistatin-1 and follistatin-3 indicates that follistatin-3 may also be involved in a physiological regulation of cell growth and differentiation, particularly with regard to cells of the reproductive system.

As one of ordinary skill would appreciate, due to the possibilities of sequencing errors discussed above, the actual complete follistatin-3 polypeptide encoded by the deposited cDNA, which comprises about 263 amino acids, may be somewhat longer or shorter. More generally, the actual open reading frame may be anywhere in the range of +20 amino acids, more likely in the range of +10 amino acids, of that predicted from either the methionine codon from the N-terminus shown in FIG. 1A (SEQ ID NO:1). It will further be appreciated that, depending on the analytical criteria used for identifying various functional domains, the exact "address" of the mature form of the follistatin-3 polypeptide may differ slightly from the predicted positions above. For example, the exact location of the cleavage site of the precursor form of the mature follistatin-3 molecule shown in SEQ ID NO:2 may vary slightly (e.g., the address may "shift" by about 6 residues, depending on the criteria used to define the cleavage site. In this case, the ends of the signal peptide and the beginning of the mature follistatin-3 molecule were predicted using the HGSI SignalP computer algorithm. One of skill in the art will realize that another widely accepted computer algorithm used to predict potential sites of polypeptide cleavage, PSORT, will predict the cleavage of an N-terminal signal peptide from the follistatin-3 polypeptide at a point slightly different from that predicted by the HGSI SignalP algorithm. In either case, as discussed further below, the invention further provides polypeptides having various residues deleted from the N-terminus of the complete polypeptide, including polypeptides corresponding to either of the predicted mature follistatin-3 polypeptides described herein.

The amino acid sequence of the complete follistatin-3 protein includes a leader sequence and a mature protein, as shown in SEQ ID NO:2. Morein particular, the present invention provides nucleic acid molecules encoding a mature form of the follistatin-3 protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature follistatin-3 polypeptide having the amino acid sequence encoded by the cDNA clone contained in the host identified as ATCC® Deposit No. 209197. By the "mature follistatin-3 polypeptide having the amino acid sequence encoded by the cDNA clone in ATCC® Deposit No. 209197" is meant the mature form(s) of the follistatin-3 protein produced by expression in a mammalian cell (e.g., COS cells, as described below) of the complete open reading frame encoded by the human DNA sequence of the clone contained in the vector in the deposited host.

In addition, methods for predicting whether a protein has a secretory leader as well as the cleavage point for that leader sequence are available. For instance, the method of McGeoch (*Virus Res.* 3:271–286 (1985)) uses the information from a short N-terminal charged region and a subsequent uncharged region of the complete (uncleaved) protein. The method of von Heinje (*Nucleic Acids Res.* 14:4683–4690 (1986)) uses the information from the residues surrounding the cleavage site, typically residues −13 to +2 where +1 indicates the amino terminus of the mature protein. The accuracy of predicting the cleavage points of known mammalian secretory proteins for each of these methods is in the range of 75–80% (von Heinje, supra). However, the two methods do not always produce the same predicted cleavage point(s) for a given protein.

In the present case, the deduced amino acid sequence of the complete follistatin-3 polypeptide was analyzed by the HGSI SignalP algorithm, which is an expert system for predicting the cellular location of a protein based on the amino acid sequence. As part of this computational prediction of localization, the methods of McGeoch and von Heinje are incorporated. Thus, the computation analysis above predicted a single cleavage site within the complete amino acid sequence shown in SEQ ID NO:2 (see above discussion).

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 19–21 of the nucleotide sequence shown in FIG. 1A (SEQ ID NO:1).

Also included are DNA molecules comprising the coding sequence for the predicted mature follistatin-3 protein shown at positions 1–237 of SEQ ID NO:2.

In addition, isolated nucleic acid molecules of the invention include DNA molecules which comprise a sequence substantially different from those described above but which, due to the degeneracy of the genetic code, still encode the follistatin-3 protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*).

In another aspect, the invention provides isolated nucleic acid molecules encoding the follistatin-3 polypeptide having an amino acid sequence encoded by the cDNA clone contained in the plasmid deposited as ATCC® Deposit No. 209197 on Aug. 8, 1997.

Preferably, this nucleic acid molecule will encode the mature polypeptide encoded by the above-described deposited cDNA clone.

The invention further provides an isolated nucleic acid molecule having the nucleotide sequence shown in FIGS. 1A, 1B, and 1C (SEQ ID NO:1) or the nucleotide sequence of the follistatin-3 cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the follistatin-3 gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO: 1 which consists of positions 1–810 of SEQ ID NO:1.

In addition, the invention provides nucleic acid molecules having nucleotide sequences related to extensive portions of SEQ ID NO:1 which have been determined from the following related cDNA clones: HHPDX66R (SEQ ID NO:4), HDTAH61R (SEQ ID NO:5), HSBAV55R (SEQ ID NO:6), HUKFS32R (SEQ ID NO:7), HOOAD78R (SEQ ID NO:8), HAQAG52R (SEQ ID NO:9), HTLEJ56R (SEQ ID NO:10), HLMNX90R (SEQ ID NO:11).

Further, the invention includes a polynucleotide comprising any portion of at least about 30 nucleotides, preferably at least about 50 nucleotides, of SEQ ID NO:1 from. residue 1 to 500. More preferably, the invention includes a polynucleotide comprising nucleotide residues 100–500, 200–500, 300–500, 400–500, 100–400, 200–400, 300–400, 100–300, 200–300, 100–200, 100–2495, 250–2495, 500–2495, 1000–2495, 1500–2495, 2000–2495, 100–2000, 250–2000, 500–2000, 1000–2000, 1500–2000, 100–1500, 250–1500, 500–1500, 1000–1500, 100–1000, 250–1000, and 500–1000.

More generally, by a fragment of an isolated nucleic acid molecule having the nucleotide sequence of the deposited cDNA or the nucleotide sequence shown in FIGS. 1A, 1B, and 1C (SEQ ID NO:1) is intended fragments at least about 15 nt, and more preferably at least about 20 nt, still more preferably at least about 30 nt, and even more preferably, at least about 40 nt in length which have uses that include, but are not limited to, as diagnostic probes and primers as discussed herein. Of course, larger fragments 50–300 nt in length are also useful according to the present invention as are fragments. corresponding to most, if not all of the nucleotide sequence of the deposited cDNA or as shown in FIGS. 1A, 1B, and 1C (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A, 1B, and 1C (SEQ ID NO:1). Preferred nucleic acid fragments of the present invention include nucleic acid molecules encoding epitope-bearing portions of the follistatin-3 polypeptide as identified in FIG. 3 and described in more detail below.

In specific embodiments, the polynucleotide fragments of the invention encode a polypeptide which demonstrates a follistatin-3 functional activity. By a polypeptide demonstrating follistatin-3 "functional activity" is meant, a polypeptide capable of displaying one or more known functional activities associated with a complete, mature or active form of the follistatin-3 polypeptide. Such functional activities include, but are not limited to, biological activity ((e.g., modulating the follicle stimulating hormone (FSH) synthetic pathway, increasing estradiol production, binding activin, stimulating of gonadotropin biosynthesis and secretion, regulating ovarian and placental steroidogenesis, and oocyte and spermatogonial maturation factor)), antigenicity [ability to bind (or compete with a follistatin-3 polypeptide for binding) to an anti-follistatin-3 antibody], immuunogenicity (ability to generate antibody which binds to a follistatin-3 polypeptide), the ability to form polymers with other follistatin-3 or inhibin or TGF-β polypeptides, and ability to bind to a receptor or ligand (e.g., an inhibin) for a follistatin-3 polypeptide.

Preferred nucleic acid fragments of the present invention also include nucleic acid molecules encoding one or more of the following domains of follistatin-3: amino acid residues 7–16, 34–45, 78–86, 91–100, 108–122, 131–145, 156–169, 184–192, and 196–210 of SEQ ID NO:2.

In specific embodiments, the polynucleotide fragments of the invention encode antigenic regions. Non-limiting examples of antigenic polypeptides or peptides that can be used to generate follistatin-3-specific antibodies include: a polypeptide comprising amino acid residues: Leu-14 to Ala-20, Ser-46 to Ile-55, Gly-88 to Pro-97, Gly-l 13 to Leu-133, Arg-138 to Glu-146, Pro-177 to Thr-191, and Gly-219 to Val-237 of SEQ ID NO:2.

In additional embodiments, the polynucleotides of the invention encode functional attributes of follistatin-3. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of follistatin-3.

The data representing the structural or functional attributes of follistatin-3 set forth in FIG. 3 and/or Table I, as described above, was generated using the various modules and algorithms of the DNA*STAR set on default parameters. In a preferred embodiment, the data presented in columns VIII, IX, XIII, and XIV of Table I can be used to determine regions of follistatin-3 which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table I, be represented or identified by using tabular representations of the data presented in FIG. 3. The DNA*STAR computer algorithm used to generate FIG. 3 (set on the original default parameters) was used to present the data in FIG. 3 in a tabular format (See Table I). The tabular format of the data in FIG. 3 may be used to easily determine specific boundaries of a preferred region.

The above-mentioned preferred regions set out in FIG. 3 and in Table I include, but are not limited to, regions of the aforementioned types identified by analysis of the amino acid sequence set out in FIGS. 1A, 1B, and 1C. As set out in FIG. 3 and in Table I, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

Among highly preferred fragments in this regard are those that comprise reigons of follistatin-3 that combine several structural features, such as two, three, four, five or more of the features set out above and in Table I.

TABLE I

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | 0.31 | −0.24 | * | * | . | 1.07 | 1.11 |
| Arg | 2 | . | . | B | . | . | . | . | 0.49 | −0.17 | * | * | . | 1.13 | 0.88 |
| Pro | 3 | . | . | . | . | T | . | . | 0.53 | −0.17 | * | * | . | 1.89 | 1.06 |
| Gly | 4 | . | . | . | . | T | . | . | 0.71 | −0.17 | * | * | . | 2.10 | 1.06 |
| Ala | 5 | . | . | . | . | . | T | C | 0.29 | −0.36 | . | * | F | 1.89 | 0.84 |
| Pro | 6 | . | . | . | . | . | T | C | 0.60 | 0.33 | . | * | F | 1.08 | 0.45 |
| Gly | 7 | . | . | . | . | . | T | C | 0.28 | 0.81 | . | * | F | 0.57 | 0.48 |
| Pro | 8 | . | . | B | . | . | T | . | −0.32 | 0.81 | . | . | F | 0.16 | 0.73 |
| Leu | 9 | . | . | B | . | . | . | . | −0.19 | 1.00 | . | . | F | −0.25 | 0.39 |
| Trp | 10 | . | . | B | . | . | . | . | 0.11 | 1.00 | . | . | . | −0.40 | 0.61 |
| Pro | 11 | . | . | B | . | . | . | . | −0.02 | 1.49 | . | . | . | −0.40 | 0.41 |
| Leu | 12 | . | . | B | . | . | T | . | −0.27 | 1.49 | . | . | . | −0.20 | 0.49 |
| Pro | 13 | . | . | . | . | T | T | . | −0.87 | 1.30 | . | . | . | 0.20 | 0.48 |
| Trp | 14 | . | . | . | . | T | T | . | −0.64 | 1.07 | . | . | . | 0.20 | 0.25 |
| Gly | 15 | . | . | . | . | . | T | C | −0.64 | 1.14 | . | . | . | 0.00 | 0.31 |
| Ala | 16 | . | A | . | . | . | . | C | −1.02 | 1.37 | . | . | . | −0.40 | 0.21 |
| Leu | 17 | . | A | B | . | . | . | . | −1.07 | 1.44 | . | . | . | −0.60 | 0.20 |
| Ala | 18 | . | A | B | B | . | . | . | −1.20 | 1.17 | . | . | . | −0.60 | 0.15 |
| Trp | 19 | . | A | B | B | . | . | . | −1.61 | 1.17 | . | . | . | −0.60 | 0.15 |
| Ala | 20 | . | A | B | B | . | . | . | −2.12 | 1.46 | . | . | . | −0.60 | 0.16 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Val | 21 | . | A | B | B | . | . | . | −1.83 | 1.41 | . | . | . | −0.60 | 0.11 |
| Gly | 22 | . | A | B | B | . | . | . | −1.32 | 1.30 | . | . | . | −0.60 | 0.15 |
| Phe | 23 | . | . | B | B | . | . | . | −1.33 | 0.77 | . | . | . | −0.60 | 0.19 |
| Val | 24 | . | . | B | B | . | . | . | −1.39 | 0.89 | . | . | . | −0.60 | 0.26 |
| Ser | 25 | . | . | B | . | . | . | . | −1.10 | 0.67 | * | . | . | −0.40 | 0.26 |
| Ser | 26 | . | . | B | . | . | . | . | −0.59 | 0.63 | . | . | F | −0.25 | 0.40 |
| Met | 27 | . | . | . | . | T | . | . | −0.24 | 0.27 | . | . | F | 0.45 | 0.53 |
| Gly | 28 | . | . | . | . | T | T | . | 0.24 | 0.03 | . | . | F | 0.82 | 0.64 |
| Ser | 29 | . | . | . | . | T | T | . | 0.51 | 0.07 | . | . | F | 0.99 | 0.74 |
| Gly | 30 | . | . | . | . | . | T | C | 0.60 | 0.19 | . | . | F | 0.96 | 0.76 |
| Asn | 31 | . | . | . | . | . | T | C | 0.56 | −0.00 | . | . | F | 1.88 | 1.18 |
| Pro | 32 | . | . | . | . | . | . | C | 0.81 | −0.00 | . | . | F | 1.70 | 0.87 |
| Ala | 33 | . | . | . | . | . | T | C | 0.30 | 0.04 | . | . | F | 1.13 | 0.87 |
| Pro | 34 | . | . | . | . | T | T | . | −0.07 | 0.26 | . | . | F | 1.16 | 0.40 |
| Gly | 35 | . | . | . | . | T | T | . | −0.01 | 0.43 | * | . | F | 0.69 | 0.14 |
| Gly | 36 | . | . | B | . | . | T | . | −0.82 | 0.91 | * | . | F | 0.12 | 0.15 |
| Val | 37 | . | A | B | . | . | . | . | −0.61 | 1.10 | * | . | . | −0.60 | 0.08 |
| Cys | 38 | . | A | B | . | . | . | . | −0.02 | 1.07 | * | . | . | −0.60 | 0.14 |
| Trp | 39 | . | A | B | . | . | . | . | −0.16 | 1.04 | * | . | . | −0.60 | 0.24 |
| Leu | 40 | . | A | B | . | . | . | . | 0.19 | 1.04 | * | . | . | −0.32 | 0.32 |
| Gln | 41 | . | . | B | . | . | T | . | 0.53 | 0.80 | * | . | F | 0.66 | 1.02 |
| Gln | 42 | . | . | . | . | T | T | . | 0.80 | 0.23 | * | . | F | 1.64 | 1.68 |
| Gly | 43 | . | . | . | . | T | T | . | 1.16 | −0.19 | * | . | F | 2.52 | 2.06 |
| Gln | 44 | . | . | . | . | T | T | . | 0.78 | −0.39 | * | . | F | 2.80 | 1.72 |
| Glu | 45 | . | . | . | . | T | . | . | 1.29 | −0.21 | * | . | F | 2.17 | 0.53 |
| Ala | 46 | . | . | . | . | T | T | . | 0.48 | −0.23 | * | . | F | 2.09 | 0.72 |
| Thr | 47 | . | . | B | . | . | T | . | −0.38 | 0.03 | . | . | . | 0.66 | 0.34 |
| Cys | 48 | . | . | B | . | . | T | . | −0.84 | 0.27 | . | . | . | 0.38 | 0.15 |
| Ser | 49 | . | . | B | . | . | T | . | −0.84 | 0.96 | . | . | . | −0.20 | 0.12 |
| Leu | 50 | . | . | B | B | . | . | . | −1.16 | 0.86 | . | * | . | −0.60 | 0.14 |
| Val | 51 | . | . | B | B | . | . | . | −0.57 | 0.86 | . | * | . | −0.60 | 0.39 |
| Leu | 52 | . | . | B | B | . | . | . | −1.11 | 0.29 | . | * | . | −0.30 | 0.48 |
| Gln | 53 | . | . | B | B | . | . | . | −0.76 | 0.54 | * | * | F | −0.45 | 0.43 |
| Thr | 54 | . | . | B | B | . | . | . | −0.34 | 0.34 | * | . | F | −0.15 | 0.85 |
| Asp | 55 | . | . | B | B | . | . | . | −0.12 | −0.30 | * | * | F | 0.60 | 2.01 |
| Val | 56 | . | A | B | B | . | . | . | 0.73 | −0.49 | * | . | F | 0.60 | 1.17 |
| Thr | 57 | . | A | B | B | . | . | . | 0.88 | −0.89 | * | * | F | 0.90 | 1.41 |
| Arg | 58 | . | A | B | B | . | . | . | 0.21 | −0.80 | * | * | F | 0.75 | 0.45 |
| Ala | 59 | . | A | B | B | . | . | . | −0.07 | −0.23 | * | * | . | 0.30 | 0.33 |
| Glu | 60 | . | A | B | B | . | . | . | −0.37 | −0.37 | * | * | . | 0.30 | 0.23 |
| Cys | 61 | . | A | B | . | . | . | . | 0.14 | −0.47 | * | * | . | 0.55 | 0.16 |
| Cys | 62 | . | . | . | . | T | T | . | 0.46 | −0.04 | * | * | . | 1.60 | 0.15 |
| Ala | 63 | . | . | . | . | T | T | . | −0.54 | −0.14 | * | * | . | 1.85 | 0.14 |
| Ser | 64 | . | . | . | . | T | T | . | 0.04 | 0.54 | . | * | F | 1.35 | 0.19 |
| Gly | 65 | . | . | . | . | T | T | . | −0.27 | −0.03 | . | * | F | 2.50 | 0.58 |
| Asn | 66 | . | . | . | . | T | T | . | −0.19 | −0.11 | . | * | F | 2.25 | 0.83 |
| Ile | 67 | . | . | B | . | . | T | . | 0.19 | −0.11 | * | * | F | 1.60 | 0.62 |
| Asp | 68 | . | . | B | . | . | T | . | 0.48 | 0.41 | * | * | F | 0.45 | 0.66 |
| Thr | 69 | . | . | B | . | . | T | . | 0.78 | 0.37 | * | * | F | 0.50 | 0.55 |
| Ala | 70 | . | . | B | . | . | . | . | 0.31 | 0.37 | * | * | . | 0.05 | 1.26 |
| Trp | 71 | . | . | B | . | . | T | . | −0.00 | 0.37 | * | . | . | 0.10 | 0.62 |
| Ser | 72 | . | . | B | . | . | T | . | 0.86 | 0.86 | * | . | . | 0.20 | 0.62 |
| Asn | 73 | . | . | B | . | . | T | . | 0.64 | 0.87 | * | . | . | 0.20 | 0.84 |
| Leu | 74 | . | . | . | . | . | T | C | 0.61 | 0.80 | * | . | . | 0.43 | 1.24 |
| Thr | 75 | . | . | . | . | . | . | C | 1.20 | 0.31 | * | . | . | 0.66 | 0.91 |
| His | 76 | . | . | . | . | . | T | C | 1.53 | 0.33 | * | . | F | 1.29 | 0.91 |
| Pro | 77 | . | . | . | . | . | T | C | 0.94 | −0.07 | * | . | F | 2.32 | 2.22 |
| Gly | 78 | . | . | . | . | T | T | . | 0.94 | −0.07 | * | * | F | 2.80 | 1.08 |
| Asn | 79 | . | . | . | . | T | T | . | 0.94 | −0.16 | * | . | F | 2.52 | 1.27 |
| Lys | 80 | . | . | B | . | . | . | . | 0.44 | 0.03 | * | * | F | 0.89 | 0.68 |
| Ile | 81 | . | . | B | . | . | . | . | 0.13 | 0.29 | . | . | F | 0.61 | 0.57 |
| Asn | 82 | . | . | B | . | . | . | . | −0.36 | 0.29 | . | * | . | 0.38 | 0.35 |
| Leu | 83 | . | . | B | B | . | . | . | −0.82 | 0.67 | . | . | . | −0.60 | 0.15 |
| Leu | 84 | . | . | B | B | . | . | . | −1.17 | 1.36 | . | * | . | −0.60 | 0.18 |
| Gly | 85 | . | . | B | B | . | . | . | −2.02 | 1.10 | . | * | . | −0.60 | 0.11 |
| Phe | 86 | . | . | B | B | . | . | . | −1.99 | 1.39 | . | . | . | −0.60 | 0.11 |
| Leu | 87 | . | . | B | B | . | . | . | −2.02 | 1.34 | . | . | . | −0.60 | 0.10 |
| Gly | 88 | . | . | B | B | . | . | . | −1.88 | 1.16 | * | . | . | −0.60 | 0.13 |
| Leu | 89 | . | . | B | B | . | . | . | −1.88 | 1.30 | . | . | . | −0.60 | 0.08 |
| Val | 90 | . | . | B | B | . | . | . | −1.74 | 1.20 | * | . | . | −0.60 | 0.08 |
| His | 91 | . | . | B | B | . | . | . | −1.71 | 0.94 | * | . | . | −0.60 | 0.13 |
| Cys | 92 | . | . | B | B | . | . | . | −0.86 | 1.09 | . | . | . | −0.60 | 0.08 |
| Leu | 93 | . | . | B | B | . | . | . | −0.51 | 0.40 | . | . | . | 0.01 | 0.23 |
| Pro | 94 | . | . | . | B | T | . | . | −0.00 | −0.24 | . | . | . | 1.32 | 0.28 |
| Cys | 95 | . | . | . | . | T | T | . | 0.19 | −0.36 | . | . | . | 2.03 | 0.70 |
| Lys | 96 | . | . | . | . | T | T | . | 0.22 | −0.36 | . | . | F | 2.49 | 0.46 |
| Asp | 97 | . | . | . | . | T | T | . | 0.54 | −1.04 | * | . | F | 3.10 | 0.49 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Ser | 98 | . | . | . | . | T | T | . | 0.50 | -1.04 | * | . | F | 2.79 | 0.91 |
| Cys | 99 | . | . | . | . | T | T | . | 0.71 | -0.97 | * | . | F | 2.48 | 0.34 |
| Asp | 100 | . | . | B | . | . | T | . | 0.71 | -0.97 | * | . | F | 1.77 | 0.35 |
| Gly | 101 | . | . | B | . | . | T | . | 0.32 | -0.40 | * | . | F | 1.47 | 0.14 |
| Val | 102 | . | . | B | . | . | T | . | 0.11 | -0.36 | * | . | . | 1.32 | 0.26 |
| Glu | 103 | . | . | B | . | . | . | . | 0.07 | -0.50 | * | . | . | 1.73 | 0.24 |
| Cys | 104 | . | . | . | . | T | . | . | 0.78 | -0.07 | * | . | F | 2.29 | 0.24 |
| Gly | 105 | . | . | . | . | T | T | . | 0.19 | -0.50 | * | . | F | 3.10 | 0.64 |
| Pro | 106 | . | . | . | . | T | T | . | -0.13 | -0.64 | * | . | F | 2.79 | 0.38 |
| Gly | 107 | . | . | . | . | T | T | . | 0.83 | -0.07 | * | . | F | 2.18 | 0.38 |
| Lys | 108 | . | . | . | . | T | T | . | 0.23 | -0.64 | * | . | F | 2.17 | 0.74 |
| Ala | 109 | . | A | B | . | . | . | . | 0.09 | -0.46 | * | . | . | 0.61 | 0.48 |
| Cys | 110 | . | A | B | . | . | . | . | 0.09 | -0.20 | * | . | . | 0.30 | 0.40 |
| Arg | 111 | . | A | B | . | . | . | . | -0.04 | -0.20 | * | . | . | 0.30 | 0.20 |
| Met | 112 | . | A | B | . | . | . | . | 0.41 | 0.23 | * | . | . | -0.30 | 0.19 |
| Leu | 113 | . | A | . | . | T | . | . | 0.16 | -0.27 | * | * | . | 1.04 | 0.70 |
| Gly | 114 | . | A | . | . | T | . | . | 0.86 | -0.41 | * | * | F | 1.53 | 0.55 |
| Gly | 115 | . | . | . | . | T | . | . | 0.86 | -0.41 | * | * | F | 2.22 | 1.10 |
| Arg | 116 | . | . | . | . | . | T | C | 0.74 | -0.46 | * | * | F | 2.41 | 0.71 |
| Pro | 117 | . | . | . | . | T | T | . | 0.68 | -1.14 | . | * | F | 3.40 | 1.25 |
| Arg | 118 | . | . | . | . | T | T | . | 0.90 | -1.00 | . | * | F | 2.91 | 0.68 |
| Cys | 119 | . | . | B | . | . | T | . | 1.03 | -0.93 | . | * | . | 2.02 | 0.35 |
| Glu | 120 | . | . | B | . | . | . | . | 1.38 | -0.50 | . | * | . | 1.73 | 0.35 |
| Cys | 121 | . | . | B | . | . | . | . | 0.60 | -0.93 | . | * | . | 1.64 | 0.30 |
| Ala | 122 | . | . | B | . | . | T | . | 0.51 | -0.36 | . | * | . | 1.45 | 0.30 |
| Pro | 123 | . | . | . | . | T | T | . | 0.06 | -0.54 | . | * | F | 2.55 | 0.23 |
| Asp | 124 | . | . | . | . | T | T | . | -0.09 | -0.11 | . | . | F | 2.50 | 0.43 |
| Cys | 125 | . | . | . | . | T | T | . | -0.30 | -0.00 | . | . | F | 2.25 | 0.35 |
| Ser | 126 | . | . | . | . | T | . | . | -0.22 | -0.07 | * | * | F | 1.80 | 0.35 |
| Gly | 127 | . | . | . | . | T | . | . | 0.48 | -0.00 | * | * | F | 1.55 | 0.21 |
| Leu | 128 | . | . | B | . | . | . | . | -0.12 | -0.00 | * | * | . | 0.75 | 0.77 |
| Pro | 129 | . | . | B | . | . | . | . | -0.12 | 0.11 | . | * | . | -0.10 | 0.47 |
| Ala | 130 | . | . | B | . | . | . | . | -0.31 | 0.13 | . | * | . | -0.10 | 0.83 |
| Arg | 131 | . | . | B | B | . | . | . | -0.68 | 0.34 | . | * | . | -0.30 | 0.74 |
| Leu | 132 | . | . | B | B | . | . | . | -0.68 | 0.23 | . | * | . | -0.30 | 0.26 |
| Gln | 133 | . | . | B | B | . | . | . | -0.17 | 0.23 | * | * | . | -0.30 | 0.25 |
| Val | 134 | . | . | B | B | . | . | . | 0.04 | 0.11 | * | * | . | -0.30 | 0.17 |
| Cys | 135 | . | . | B | B | . | . | . | 0.29 | 0.11 | * | * | . | -0.02 | 0.35 |
| Gly | 136 | . | . | B | . | . | T | . | -0.41 | -0.14 | * | * | F | 1.41 | 0.20 |
| Ser | 137 | . | . | . | . | T | T | . | 0.09 | -0.04 | . | . | F | 2.09 | 0.27 |
| Asp | 138 | . | . | . | . | T | T | . | -0.16 | -0.20 | . | * | F | 2.37 | 0.73 |
| Gly | 139 | . | . | . | . | T | T | . | 0.81 | -0.01 | . | . | F | 2.80 | 1.16 |
| Ala | 140 | . | . | . | . | T | . | . | 1.48 | -0.44 | . | . | F | 2.32 | 1.70 |
| Thr | 141 | . | . | B | . | . | . | . | 1.82 | -0.83 | . | . | . | 1.99 | 1.70 |
| Tyr | 142 | . | . | B | . | . | T | . | 1.46 | -0.83 | . | * | . | 2.11 | 2.97 |
| Arg | 143 | . | . | B | . | . | T | . | 1.46 | -0.69 | . | * | F | 2.18 | 1.57 |
| Asp | 144 | . | . | B | . | . | T | . | 0.99 | -1.19 | . | * | F | 2.10 | 1.89 |
| Glu | 145 | . | . | B | . | . | T | . | 1.69 | -0.99 | . | * | . | 2.00 | 0.99 |
| Cys | 146 | . | A | B | . | . | . | . | 1.41 | -1.74 | . | * | . | 1.40 | 0.99 |
| Glu | 147 | A | A | . | . | . | . | . | 1.07 | -1.24 | . | * | . | 1.20 | 0.60 |
| Leu | 148 | A | A | . | . | . | . | . | 1.07 | -0.74 | . | * | . | 1.00 | 0.35 |
| Arg | 149 | A | A | . | . | . | . | . | 0.40 | -0.74 | . | * | . | 0.95 | 1.28 |
| Ala | 150 | A | A | . | . | . | . | . | 0.51 | -0.74 | * | * | . | 0.60 | 0.40 |
| Ala | 151 | . | A | . | . | T | . | . | 0.83 | -0.74 | . | * | . | 1.00 | 0.94 |
| Arg | 152 | . | A | . | . | T | . | . | 0.80 | -1.00 | . | * | . | 1.00 | 0.48 |
| Cys | 153 | . | A | . | . | T | . | . | 1.40 | -0.50 | . | * | . | 1.27 | 0.64 |
| Arg | 154 | . | A | . | . | T | . | . | 1.29 | -0.57 | . | * | . | 1.54 | 0.98 |
| Gly | 155 | . | A | . | . | T | . | . | 1.07 | -1.07 | . | * | F | 1.96 | 0.84 |
| His | 156 | . | . | . | . | . | T | C | 1.36 | -0.39 | . | * | F | 2.28 | 1.29 |
| Pro | 157 | . | . | . | . | . | T | C | 0.39 | -0.57 | . | * | F | 2.70 | 0.88 |
| Asp | 158 | . | . | . | . | T | T | . | 0.46 | 0.07 | * | * | F | 1.73 | 0.66 |
| Leu | 159 | . | . | B | . | . | T | . | 0.10 | 0.26 | * | * | . | 0.91 | 0.48 |
| Ser | 160 | . | . | B | B | . | . | . | 0.56 | 0.51 | * | * | . | -0.06 | 0.49 |
| Val | 161 | . | . | B | B | . | . | . | 0.24 | 0.09 | . | * | . | -0.03 | 0.57 |
| Met | 162 | . | . | B | B | . | . | . | 0.57 | 0.51 | . | * | . | -0.26 | 0.69 |
| Tyr | 163 | . | . | B | . | . | T | . | -0.10 | -0.17 | * | * | . | 1.53 | 1.00 |
| Arg | 164 | . | . | B | . | . | T | . | 0.82 | 0.01 | . | * | . | 1.12 | 0.72 |
| Gly | 165 | . | . | . | . | T | T | . | 1.17 | -0.63 | . | * | F | 3.06 | 1.43 |
| Arg | 166 | . | . | . | . | T | T | . | 1.72 | -1.24 | . | * | F | 3.40 | 1.83 |
| Cys | 167 | . | . | . | . | T | . | . | 1.66 | -1.61 | * | * | F | 2.86 | 1.25 |
| Arg | 168 | . | . | . | . | T | T | . | 1.90 | -1.04 | * | * | F | 2.57 | 0.68 |
| Lys | 169 | . | . | . | . | T | T | . | 1.76 | -1.47 | * | * | F | 2.23 | 0.60 |
| Ser | 170 | . | . | . | . | T | T | . | 1.24 | -0.97 | * | * | F | 2.04 | 1.52 |
| Cys | 171 | . | . | . | . | T | T | . | 0.28 | -0.90 | * | * | . | 1.40 | 0.58 |
| Glu | 172 | . | . | B | B | . | . | . | 0.28 | -0.26 | * | . | . | 0.30 | 0.21 |
| His | 173 | . | . | B | B | . | . | . | -0.04 | 0.31 | . | . | . | -0.30 | 0.09 |
| Val | 174 | . | . | B | B | . | . | . | 0.02 | 0.36 | . | * | . | -0.02 | 0.25 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Val | 175 | . | . | B | B | . | . | . | 0.11 | −0.21 | . | * | . | 0.86 | 0.28 |
| Cys | 176 | . | . | B | . | . | T | . | 0.78 | 0.21 | . | * | . | 0.94 | 0.32 |
| Pro | 177 | . | . | . | . | T | T | . | 0.48 | 0.11 | . | * | F | 1.77 | 0.74 |
| Arg | 178 | . | . | . | . | T | T | . | −0.16 | −0.14 | . | * | F | 2.80 | 1.34 |
| Pro | 179 | . | . | . | . | T | T | . | −0.16 | −0.21 | . | * | F | 2.52 | 1.34 |
| Gln | 180 | . | . | . | B | T | . | . | −0.16 | −0.14 | * | * | F | 1.69 | 0.64 |
| Ser | 181 | . | . | B | B | . | . | . | 0.51 | 0.07 | * | * | F | 0.41 | 0.24 |
| Cys | 182 | . | . | B | B | . | . | . | 0.72 | 0.07 | * | * | . | −0.02 | 0.26 |
| Val | 183 | . | . | B | B | . | . | . | 0.30 | 0.04 | * | * | . | −0.30 | 0.26 |
| Val | 184 | . | . | B | B | . | . | . | 0.17 | 0.13 | . | . | . | 0.02 | 0.28 |
| Asp | 185 | . | . | B | B | . | . | . | −0.13 | 0.17 | . | . | F | 0.41 | 0.52 |
| Gln | 186 | . | . | B | . | . | T | . | −0.42 | −0.01 | . | . | F | 1.69 | 0.94 |
| Thr | 187 | . | . | . | . | T | T | . | 0.21 | −0.16 | . | . | F | 2.52 | 1.28 |
| Gly | 188 | . | . | . | . | T | T | . | 0.40 | −0.30 | . | . | F | 2.80 | 1.04 |
| Ser | 189 | . | . | . | . | T | T | . | 0.40 | 0.27 | . | . | F | 1.77 | 0.32 |
| Ala | 190 | . | . | B | B | T | . | . | −0.46 | 0.51 | . | . | . | 0.64 | 0.17 |
| His | 191 | . | . | B | B | . | . | . | −1.12 | 0.67 | * | . | . | −0.04 | 0.12 |
| Cys | 192 | . | . | B | B | . | . | . | −0.70 | 0.81 | * | * | . | −0.32 | 0.05 |
| Val | 193 | . | . | B | B | . | . | . | −0.94 | 0.43 | * | . | . | −0.60 | 0.10 |
| Val | 194 | . | . | B | B | . | . | . | −1.23 | 0.43 | * | . | . | −0.60 | 0.07 |
| Cys | 195 | . | . | B | B | . | . | . | −0.86 | 0.43 | * | . | . | −0.60 | 0.14 |
| Arg | 196 | . | . | B | B | . | . | . | −1.49 | 0.29 | * | . | . | −0.30 | 0.28 |
| Ala | 197 | . | . | B | B | . | . | . | −1.03 | 0.21 | * | . | . | −0.30 | 0.20 |
| Ala | 198 | . | . | B | . | . | T | . | −1.03 | −0.00 | * | . | . | 0.70 | 0.59 |
| Pro | 199 | . | . | B | . | . | T | . | −0.39 | 0.07 | * | . | . | 0.10 | 0.22 |
| Cys | 200 | . | . | B | . | . | T | . | −0.02 | 0.50 | * | . | . | −0.20 | 0.34 |
| Pro | 201 | . | . | B | . | . | T | . | −0.43 | 0.39 | * | . | . | 0.10 | 0.45 |
| Val | 202 | . | . | B | . | . | . | . | −0.06 | 0.27 | . | . | F | 0.05 | 0.39 |
| Pro | 203 | . | . | . | . | T | . | . | 0.19 | 0.27 | . | . | F | 0.88 | 1.13 |
| Ser | 204 | . | . | . | . | T | . | . | 0.40 | 0.13 | . | . | F | 1.01 | 0.72 |
| Ser | 205 | . | . | . | . | . | T | C | 1.07 | 0.10 | * | . | F | 1.44 | 1.69 |
| Pro | 206 | . | . | . | . | T | T | . | 0.47 | −0.54 | * | . | F | 2.82 | 1.89 |
| Gly | 207 | . | . | . | . | T | P | . | 0.66 | −0.29 | . | . | F | 2.80 | 1.16 |
| Gln | 208 | . | . | B | . | . | T | . | 0.52 | −0.10 | . | . | F | 1.97 | 0.47 |
| Glu | 209 | . | . | B | . | . | . | . | 0.82 | −0.06 | . | . | F | 1.49 | 0.30 |
| Leu | 210 | . | . | B | . | . | . | . | 1.12 | −0.09 | . | . | F | 1.37 | 0.48 |
| Cys | 211 | . | . | B | . | . | T | . | 1.33 | −0.11 | . | . | F | 1.45 | 0.45 |
| Gly | 212 | . | . | . | . | T | T | . | 0.82 | −0.11 | . | . | F | 1.73 | 0.42 |
| Asn | 213 | . | . | . | . | T | T | . | 0.51 | 0.53 | . | * | F | 0.99 | 0.38 |
| Asn | 214 | . | . | . | . | T | T | . | 0.27 | 0.33 | . | * | F | 1.60 | 1.01 |
| Asn | 215 | . | . | . | B | T | . | . | 0.19 | 0.51 | . | . | F | 0.74 | 1.60 |
| Val | 216 | . | . | B | B | . | . | . | 0.56 | 0.77 | * | . | . | −0.12 | 0.70 |
| Thr | 217 | . | . | B | B | . | . | . | 0.60 | 0.76 | * | . | . | −0.28 | 0.58 |
| Tyr | 218 | . | . | B | B | . | . | . | −0.07 | 0.74 | . | . | . | −0.44 | 0.48 |
| Ile | 219 | . | . | B | B | . | . | . | −0.10 | 0.91 | . | . | . | −0.60 | 0.35 |
| Ser | 220 | . | . | B | . | . | T | . | −0.70 | 0.77 | * | * | . | −0.20 | 0.33 |
| Ser | 221 | . | . | B | . | . | T | . | 0.27 | 0.90 | * | . | . | −0.20 | 0.21 |
| Cys | 222 | . | . | B | . | . | T | . | 0.58 | 0.14 | * | . | . | 0.10 | 0.58 |
| His | 223 | . | . | B | . | . | T | . | 0.23 | −0.14 | * | . | . | 0.70 | 0.75 |
| Met | 224 | . | . | . | . | T | . | . | 0.81 | −0.03 | * | . | . | 0.90 | 0.57 |
| Arg | 225 | . | . | B | B | . | . | . | 0.44 | 0.07 | * | * | . | −0.15 | 1.53 |
| Gln | 226 | . | . | B | B | . | . | . | 0.04 | 0.07 | * | . | . | −0.30 | 0.60 |
| Ala | 227 | . | . | B | B | . | . | . | −0.10 | 0.36 | * | . | . | −0.30 | 0.53 |
| Thr | 228 | . | . | B | B | . | . | . | −0.41 | 0.43 | * | * | . | −0.60 | 0.22 |
| Cys | 229 | . | . | B | B | . | . | . | 0.30 | 0.86 | * | * | . | −0.60 | 0.13 |
| Phe | 230 | . | . | B | B | . | . | . | −0.11 | 0.46 | * | . | . | −0.60 | 0.25 |
| Leu | 231 | . | . | B | B | . | . | . | −1.00 | 0.34 | * | . | . | −0.30 | 0.23 |
| Gly | 232 | . | . | . | . | T | T | . | −0.76 | 0.54 | * | . | . | 0.20 | 0.30 |
| Arg | 233 | . | . | . | . | T | T | . | −1.30 | 0.40 | . | * | F | 0.65 | 0.34 |
| Ser | 234 | . | . | . | . | T | T | . | −0.52 | 0.26 | . | . | F | 0.65 | 0.31 |
| Ile | 235 | . | . | B | . | . | T | . | 0.14 | −0.43 | . | . | . | 0.70 | 0.61 |
| Gly | 236 | . | . | B | B | . | . | . | 0.37 | −0.36 | . | . | . | 0.30 | 0.42 |
| Val | 237 | . | . | B | B | . | . | . | 0.37 | 0.14 | . | . | . | −0.30 | 0.32 |
| Arg | 238 | . | . | B | B | . | . | . | −0.04 | 0.19 | . | * | . | −0.30 | 0.45 |
| His | 239 | . | . | B | . | . | T | . | −0.41 | −0.11 | * | * | . | 0.70 | 0.61 |
| Ala | 240 | . | . | . | . | T | T | . | −0.11 | 0.03 | * | * | . | 0.50 | 0.44 |
| Gly | 241 | . | . | . | . | T | T | . | −0.11 | −0.11 | * | . | . | 1.10 | 0.23 |
| Ser | 242 | . | . | . | . | T | T | . | 0.43 | 0.31 | * | * | . | 0.80 | 0.16 |
| Cys | 243 | . | . | . | . | T | T | . | 0.11 | 0.30 | * | . | . | 1.10 | 0.24 |
| Ala | 244 | . | . | . | . | T | T | . | 0.14 | 0.23 | . | . | . | 1.40 | 0.37 |
| Gly | 245 | . | . | . | . | . | T | C | 0.73 | −0.20 | . | . | F | 2.25 | 0.47 |
| Thr | 246 | . | . | . | . | . | T | C | 0.87 | −0.59 | . | . | F | 3.00 | 1.53 |
| Pro | 247 | . | . | . | . | . | . | C | 0.96 | −0.73 | . | . | F | 2.50 | 2.35 |
| Glu | 248 | . | . | . | . | . | . | C | 1.28 | −0.80 | . | . | F | 2.50 | 3.67 |
| Glu | 249 | . | . | . | . | . | . | C | 1.52 | −0.80 | . | . | F | 2.50 | 2.52 |
| Pro | 250 | . | . | . | . | . | T | C | 1.87 | −0.86 | . | . | F | 2.70 | 1.61 |
| Pro | 251 | . | . | . | . | . | T | C | 1.88 | −1.29 | . | . | F | 2.70 | 1.61 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Gly | 252 | . | . | . | . | . | T | C | 1.50 | −0.90 | . | . | F | 3.00 | 1.25 |
| Gly | 253 | . | . | . | . | . | T | C | 1.50 | −0.40 | . | . | F | 2.25 | 0.81 |
| Glu | 254 | . | A | . | . | . | . | C | 1.50 | −0.83 | . | . | F | 1.85 | 0.91 |
| Ser | 255 | . | A | . | . | . | . | C | 1.71 | −1.26 | . | . | F | 1.70 | 1.60 |
| Ala | 256 | A | A | . | . | . | . | . | 1.92 | −1.69 | * | . | F | 1.20 | 2.79 |
| Glu | 257 | A | A | . | . | . | . | . | 2.27 | −2.11 | * | . | F | 0.90 | 2.79 |
| Glu | 258 | A | A | . | . | . | . | . | 1.91 | −1.71 | * | . | F | 0.90 | 3.35 |
| Glu | 259 | A | A | . | . | . | . | . | 1.06 | −1.31 | * | . | F | 0.90 | 2.87 |
| Glu | 260 | A | A | . | . | . | . | . | 0.97 | −1.17 | * | . | F | 0.90 | 1.23 |
| Asn | 261 | A | A | . | . | . | . | . | 1.17 | −0.74 | * | . | . | 0.60 | 0.91 |
| Phe | 262 | A | A | . | . | . | . | . | 0.78 | −0.31 | . | . | . | 0.30 | 0.67 |
| Val | 263 | A | A | . | . | . | . | . | 0.39 | 0.11 | . | . | . | −0.30 | 0.49 |

In another aspect, the invention provides an isolated nucleic acid molecule comprising a polynucleotide which hybridizes under strigent hybridization condition to a portion of the polynucleotide in a nucleic acid molecule of the invention described above, for instance, the cDNA clone contained in ATCC® Deposit No. 209197, a polynucleotide sequence encoding the follistatin-3 polypeptide having the amino acid sequence depicted in FIGS. 1A–C (SEQ ID NO:2), or fragments (i.e., portions) thereof (as described herein). By "stringent hybridization conditions" is intended one-night incubation an 42° C. in a solution comprising: 50% formamide. 5×SSC (750mM NaCl, 75 mM trisodium citrate), 50 mM sodium phosphate (p7.6), 5× Denhardts solution, 10% dexuan sulfate, and 20 μg/ml denatured, Sheared salmon sperm DNA, followed by washing the tilters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A, 1B, and 1C (SEQ ID NO:1)). Of course, a polynucleotide which hybridizes only to a poly A sequence (such as the 3' terminal poly(A) tract of the follistatin-3 cDNA shown in FIGS. 1A, 1B, and 1C (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

In preferred embodiments, polynucleotides which hybridize to the reference polynucleotides disclosed herein encode polypeptides which either retain substantially the same functional or biological activity as the mature form of the follistatin-3 polypeptide encoded by the polynucleotide sequence depicted in FIGS. 1A, 1B, and 1C (SEQ ID NO:1) or the clone contained in the deposit (HDTAH85).

Alternative embodiments are directed to polynucleotides which hybridize to the reference polynucleotide (i.e., a polynucleotide sequence disclosed herein), but do not retain biological activity. While these polynucleotides do not retain biological activity, they have uses, such as, for example, as probes for the polynucleotides of SEQ ID NO:1, for recovery of the polynucleotides, as diagnostic probes, and as PCR primers.

As indicated, nucleic acid molecules of the present invention which encode a follistatin-3 polypeptide may include, but are not limited to, those encoding the amino acid sequence of the mature polypeptide, by itself; and the coding sequence for the mature polypeptide and additional sequences, such as those encoding the about 26 amino acid leader or secretory sequence, such as a pre-, or pro- or prepro-protein sequence; the coding sequence of the mature polypeptide, with or without the aforementioned additional coding sequences.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described by Gentz and colleagues (*Proc. Natl. Acad. Sci. USA* 86:821–824 (1989)), for instance, hexa-histidine provides for convenient purification of the fusion protein. The "HA" tag is another peptide useful for purification which corresponds to an epitope derived from the influenza hemagglutinin protein, which has been described by Wilson and coworkers (*Cell* 37:767 (1984)). As discussed below, other such fusion proteins include the follistatin-3 fused to Fc at the N- or C-terminus.

The present invention further relates to variants of the nucleic acid molecules of the present invention, which encode portions, analogs or derivatives of the follistatin-3 polypeptide. Variants may occur naturally, such as a natural allelic variant. By an "allelic variant" is intended one of several alternate forms of a gene occupying a given locus on a chromosome of an organism (*Genes II*, Lewin, B., ed., John Wiley & Sons, New York (1985)). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the follistatin-3 polypeptide or portions thereof. Also especially preferred in this regard are conservative substitutions.

Most highly preferred are nucleic acid molecules encoding the mature protein having the amino acid sequence shown in SEQ ID NO:2 or the mature follistatin-3 amino acid sequence encoded by the deposited cDNA clone.

Further embodiment include an isolated nucleic acid molecule comprising a polynucleotide having a nucleotide sequence a least 90% identical, and more preferably at least 95%, 96%, 97%, 98% or 99% identical to a polynucleotide selected from the group consisting of (a) a nucleotide Sequence encoding the follistatin-3 polypeptide having the complete amino acid sequence in SEQ ID NO:2 (i.e., positions −26 to 237 of SEQ ID NO:2); (b) a nucleotide sequence encoding the follistatin-3 polypeptide having the complete amino acid sequence in SEQ ID NO:2 excepting the N-terminal methionine (i.e., positions −25 to 237 of SEQ ID NO:2); (C) a nucleotide sequence encoding the predicted mature follistatin-3 polypeptide having the amino acid sequence at positions 1 to 237 in SEQ ID NO:2; (d) a nucleotide sequence encoding the follistatin-3 polypeptide having the complete amino acid sequence encoded by the cDNA clone contained in ATCC® deposit No. 209197; (e) a nucleotide sequence encoding the follistatin-3 polypeptide having the complete amino acid sequence excepting the N-terminal methionine encoded by the cDNA clone contained in ATCC® Deposit No. 209197; (1) a nucleotide sequence encoding the mature follistatin-3 polypeptide having the amino acid sequence encoded by the cDNA clone contained in ATCC® Deposit No. 209197; and (g) a nucleotide sequence complementary to any of the nucleotide sequences in (a), (b), (c), (d), (e) or (f) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e), (f) or (g), above, or a polynucleotide which hybridizes under stringent hybridization conditions to a polynucleotide in (a), (b), (c), (d), (e), (f) or (g), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a follistatin-3 polypeptide having an amino acid sequence in (a), (b), (c), (d), (e) or (f), above. A further nucleic acid embodiment of the invention relates to an isolated nucleic acid molecule comprising a polynucleotide which encodes the amino acid sequence of a follistatin-3 polypeptide having an amino acid sequence which contains at least one conservative amino acid substitution, but not more than 50 conservative amino acid substitutions, even more preferably, not more than 40 conservative amino acid substitutions, still more preferably not more than 30 conservative amino acid substitutions, and still even more preferably not more than 20 conservative amino acid substitutions. Of course, in order of ever-increasing preference, it is highly preferable for a polynucleotide which encodes the amino acid sequence of a follistatin-3 polypeptide to have an amino acid sequence which contains not more than 7–10, 5–10, 3–7, 3–5, 2–5, 1–5, 1–3, 10, 9, 8, 7, 6, 5, 4, 3, 2 or 1 conservative amino acid substitutions.

The present invention also relates to recombinant vectors, which include the isolated nucleic acid molecules of the present invention, and to host cells containing the recombinant vectors, as well as to methods of making such vectors and host cells and for using them for production of follistatin-3 polypeptides or peptides by recombinant techniques.

By a polynucleotide having a nucleotide sequence at least, for example, 95% "identical" to a reference nucleotide sequence encoding a follistatin-3 polypeptide is intended that the nucleotide sequence of the polynucleotide is identical to the reference sequence except that the polynucleotide sequence may include up to five point mutations per each 100 nucleotides of the reference nucleotide sequences encoding the follistatin-3 polypeptides. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIGS. 1A, 1B, and 1C, or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman to find the best segment of homology between two sequences (*Advances in Applied Mathematics* 2:482–489 (1981)). When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed. A preferred method for determing the best overall match between a query sequence (a sequence of the present invention) and a subject sequence, also referred to as a global sequence alignment, can be determined using the FASTDB computer program based on the algorithm of Brutlag and colleagues (*Comp. App. Biosci.* 6:237–245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score;

For example, a 90 base subject sequence is aligned to a 100 base query sequence to determine percent identity. The deletions occur at the 5' end of the subject sequence and therefore, the FASTDB alignment does not show a matched/alignement of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

The present application is directed to nucleic acid molecules at least 90%, 95%, 96%, 97%, 98% or 99% identical to the nucleic acid sequence shown in FIGS. 1A, 1B, and 1C (SEQ ID NO:1) or to the nucleic acid sequence of the deposited cDNA, irrespective of whether they encode a polypeptide having follistatin-3 activity. This is because even where a particular nucleic acid molecule does not encode a polypeptide having follistatin-3 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having follistatin-3 activity include, inter alia, (1) isolating the follistatin-3 gene or allelic variants thereof in a cDNA library; (2) in situ hybridization (e.g., "FISH") to metaphase chromosomal spreads to provide precise chromosomal location of the follistatin-3 gene, as described by Verma and colleagues (*Human Chromosomes: A Manual of Basic Techniques*, Pergamon Press, New York. (1988)); and Northern Blot analysis for detecting follistatin-3 mRNA expression in specific tissues.

Preferred, however, are nucleic acid molecules having sequences at least 90%, 95%, 96%, 97%, 98% or 99% identical to the nucleic acid sequence shown in FIGS. 1A, 1B, and 1C (SEQ ID NO:1) or to the nucleic acid sequence of the deposited cDNA which do, in fact, encode a polypeptide having follistatin-3 activity. By "a polypeptide having follistatin-3 activity" is intended polypeptides exhibiting activity similar, but not necessarily identical, to an activity of the mature follistatin-3 polypeptide of the invention, as measured in a particular biological assay. For example, the follistatin-3 polypeptide of the present invention-inhibits the binding of activin to the activin receptor. An activin receptor-binding inhibition assay is described by Hashimoto and colleagues (*J. Biol. Chem.* 272:13835–13842 (1997)). Briefly, the assay involves culturing rat pituitary cells ($5\times10^5$ cells) in 24-well plates in the presence of [$^{125}$I]-activin A (40 ng/mL; activin A is labeled using the chloramine-T method as described by Hasegawa and coworkers (*Endocrinol. Japan* 33:645–654 (1986)) and follistatin-3 or a mutein thereof (200 $\mu$g/mL). A baseline of activin-binding is determined by affinity cross-linking [$^{125}$I]-activin A to the pituitary cells using the bifunctional chemical cross-linker disuccinimidyl suberate (DSS) in the absence of follistatin-3. Cross-linking is achieved by washing cells once with binding buffer (DMEM containing 25 mM HEPES (pH 7.4) and 0.2% bovine serum albumen) and incubating on ice for 2 h with 40 ng/mL [$^{125}$I]-activin A in the binding buffer. Following incubation, cells are washed 3 times with ice-cold PBS and incubated in PBS containing 1 mM DSS for 20 min on ice. The reaction is then quenched with PBS. The cells are removed from the culture dish by scraping, rinsed with a Tris solution (20 mM Tris-HCl (pH 7.2) containing 2 mM EDTA, 5 mM benzamidine, 2 mM phenylmethylsulfonyl fluoride (PMSF), 2 mM N-ethylaleimide, and 2 mM diisopropyl fluorophosphate), centrifuged, and resuspended in solubilization buffer (50 mM Tris-HCl (pH 7.2) containing 150 mM NaCl, 2 mM EDTA, 5 mM benzamidine, 2 mM PMSF, 2 mM N-ethylaleimide, 2 mM diisopropyl fluorophosphate, 1% Triton X-100, and 10% glycerol), and stirred gently on ice for 1 h. The cell lysates are introduced into 2% SDS and boiled at 100° C. for 10 min. The resulting affinity-labeled lysates are then subject to SDS-PAGE (7.5 or 8% gels). Following SDS-PAGE, gels are fixed, stained with 0.25% Coomassie Brilliant Blue R-250, destained, air-dried, and then visualized by autoradiography. Inhibition of activin binding of the activin receptor is analyzed in samples with which follistatin-3 or a mutein thereof (200 $\mu$g/mL) are incubated with labeled activin in the binding buffer incubation described above. The degree to which the formation of affinity cross-linked activin/activin receptor complexes is decreased correlates with the ability of follistatin-3 or a mutein thereof to bind to labeled activin protein. As such, the relative binding affinity of activin for its receptor versus follistatin-3 or a mutein thereof can be quantitated. Such activity is useful for regulating the effective amount of activin present in a given system.

Follistatin-3 binds to activin in a dose-dependent manner in the above-described assay. While polypeptides of the invention need not demonstrate dose-dependent follistatin-3 activity in a bioassay, it is preferred that, by "a polypeptide having follistatin-3 activity" is meant a polypeptide that also exhibits any of the same binding activities in the above-described assays in a dose-dependent manner. Thus, although the degree of dose-dependent activity need not be identical to that of the follistatin-3, most preferably, "a polypeptide having follistatin-3 activity" will exhibit substantially similar dose-dependence in a given activity as compared to the follistatin-3 (i.e., the candidate polypeptide will exhibit greater activity or not more than about 25-fold less and, preferably, not more than about tenfold less activity relative to the reference follistatin-3).

Like follistatin-1, follistatin-3 inhibits the secretion of FSH. An assay for measuring the suppression of spontaneous FSH release from primary cultured rat pituitary cells is well known in the art (Hasegawa, Y., et al., *Endocrinol. Jpn.* 33:645–654 (1986)). Briefly, freshly isolated pituitary cells are suspended in DMEM containing gentamicin (35 μg/mL), fungizone (1 μg/mL), 0.05% glutamine, 0.1% sodium bicarbonate, 10% horse serum, and 2.5% fetal bovine serum at a density of $3\times10^5$ cells/mL, and plated in 96-well culture plates ($6\times10^4$ cells/0.2 mL/well). Various amounts (0.1–100 ng/mL) of follistatin-3 are then added to the culture medium. After culturing for 3 days at 37° C. (5% $CO_2$), cultured media are assayed for quantity of secreted FSH by a double antibody RIA method using an RIA kit and plotted as FSH Secreted (ng/mL/72 h) versus Protein Added (ng/mL).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIGS. 1A, 1B, and 1C (SEQ ID NO:1) will encode a polypeptide "having follistatin-3 activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having follistatin-3 activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

While the follistatin-3 polypeptides (including fragments, variants derivatives, and analogs) of the invention can be chemically synthesized (e.g., see Creighton, 1983, Proteins: Structures and Molecular Principles, W.H. Freeman & Co., New York), follistatin-3 polypeptides may advantageously be produced by recombinant DNA technology using techniques well known in the art for expressing gene sequences and/or nucleic acid coding sequences. Such methods can be used to construct expression vectors containing the polynucleotides of the invention and appropriate transcriptional and translational control signals. These methods include, for example, in vitro recombinant DNA techniques, synthetic techniques, and in vivo genetic recombination. See, for example, the techniques described in Sambrook et al., 1989, supra; Ausubel et al., 1989, supra; Caruthers et al., 1980, Nuc. Acids Res. Symp. Ser. 7:215–233; Crea and Horn, 1980, Nuc. Acids Res. 9(10):2331; Matteucci and Caruthers, 1980, Tetrahedron Letters 21:719; and Chow and Kempe, 1981, Nuc. Acids Res. 9(12):2807–2817. Alternatively, RNA capable of producing follistatin-3 sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

Thus, in one embodiment, the present invention relates to vectors which include the isolated DNA molecules (i.e., polynucleotides) of the present invention, host cells which are genetically engineered with the recombinant vectors, and the production of follistatin-3 polypeptides or fragments thereof by recombinant techniques using these host cells or host cells that have otherwise been genetically engineered using techniques known in art to express a polypeptide of the invention. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

In one embodiment, the polynucleotide of the invention is operatively associated with an appropriate heterologous regulatory element (e.g., a promoter or enhancer or both), such as the phage lambda PL promoter, the *E. coli* lac, trp, phoA and tac promoters, the SV40 early and late promoters and promoters of retroviral LTRs, to name a few. Other suitable promoters will be known to the skilled artisan.

In embodiments in which vectors contain expression constructs, these constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Vectors preferred for use in bacteria include pHE4-5, pQE70, pQE60 and pQE-9 (QIAGEN, Inc., supra); pBS vectors, Phagescript vectors, Bluescript vectors, pNH8A, pNH16a, pNH18A, pNH46A (Stratagene); and ptrc99a, pKK223-3, pKK233-3, pDR540, pRIT5 (Pharmacia). Among preferred eukaryotic vectors are pWLNEO, pSV2CAT, pOG44, pXT1, and pSG (Stratagene); and pSVK3, pBPV, pMSG and pSVL (Pharmacia). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals (for example, Davis, et al., *Basic Methods In Molecular Biology* (1986)).

In addition to encompassing host cells containing the vector constructs discussed herein, the invention also encompasses primary, secondary, and immortalized host cells of vertebrate origin, particularly those of mammalian origin, that have been engineered to delete or replace endogenous genetic material (e.g., foulistatin-3 coding sequence), and/or to include genetic material (e.g. heterologous polynucleotide sequences) that is operably associated with follistatin-3 polynucleotides of the invention, and which activates, alters, and/or amplifies endogenous follistatin-3 polynucleotides. For example, techniques known in the art may be used to operably associate heterologous control regions (e.g. promoter and/or enhancer) and endogenous follistatin-3 polynucleotide sequences via homologous recombination (see, e.g. U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra, et al., Nature 342:435–438 (1989), the disclosures of each of which are hereby incorporated by reference in their entireties).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5 (Bennett, D., et al., *J. Molecular Recognition* 8:52–58 (1995); Johanson, K., et al., *J. Biol. Chem.* 270:9459–9471 (1995)).

The follistatin-3 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Included-within the scope of the invention are follistatin-3 polypeptides (including fragments, variants, derivatives and analogs) which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including, but not limited to, specific chemical cleavage by cyanogen bromide, trypsin, chymotrypsin, papain, V8 protease, NaBH4; acetylation, formylation, oxidation, reduction; metabolic synthesis in the presence of tunicamycin; etc. In a specific embodiment, the compositions of the invention are conjugated to other molecules to increase their water-solubility (e.g., polyethylene glycol), half-life, or ability to bind targeted tissue.

Polypeptides and Fragments

The invention further provides an isolated follistatin-3 polypeptide having the amino acid sequence encoded by the deposited cDNA, or the amino acid sequence in SEQ ID NO:2, or a peptide or polypeptide comprising fragment (i.e., a portion) of the above polypeptides.

The polypeptides and polynucleotides of the present invention are preferably provided in an isolated form, and preferably are purified to a point within the range of near complete (e.g., >90% pure) to complete (e.g., >99% pure) homogeneity. The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Also intended as an "isolated polypeptide" are polypeptides that have been purified partially or substantially from a recombinant host cell. For example, a recombinantly produced version of a follistatin-3 polypeptide can be substantially purified by the one-step method described by Smith and Johnson (*Gene* 67:31–40 (1988)). Such polynucleotides could be part of a vector and/or such polynucleotides or polypeptides could be part of a composition, and still be isolated in that such vector or composition is not part of its natural environment. Isolated polypeptides and polynucleotides according to the present invention also include such molecules produced naturally or synthetically. Polypeptides and polynucleotides of the invention also can be purified from natural or-recombinant sources using anti-follistatin-3 antibodies of the invention which may routinely be generated and utilized using methods known in the art.

The present invention also encompasses fragments of the above-described follistatin-3 polypeptides. Polypeptide fragments of the present invention include polypeptides comprising an amino acid sequence contained in SEQ ID NO:2, encoded by the cDNA contained in the deposited clone, or encoded by nucleic acids which hybridize (e.g., under stringent hybridization conditions) to the nucleotide sequence contained in the deposited clones, that shown in FIGS. 1A, 1B, and 1C (SEQ ID NO:1), or the complementary strand thereto.

The polynucleotide fragments of the invention encode a polypeptide which demonstrates a functional activity. By a polypeptide demonstrating "functional activity" is meant, a polypeptide capable of displaying one or more known functional activities associated with a complete, mature or active form of the follistatin-3 polypeptide. Such functional activities include, but are not limited to, biological activity ((e.g., modulating the follicle stimulating hormone (FSH) synthetic pathway, increasing estradiol production, binding activin, stimulating gonadotropin biosynthesis and secretion, regulating of ovarian and placental steroidogenesis, and oocyte and spermatogonial maturation factor)), antigenicity [ability to bind (or compete with a follistatin-3 polypeptide for binding) to an anti-follistatin-3 antibody], immunogenicity (ability to generate antibody which binds to a follistatin-3 polypeptide), the ability to form polymers with other follistatin-3 or inhibin or TGF-b polypeptides, and ability to bind to a receptor or ligand for a follistatin-3 polypeptide (e.g., an activin).

Polypeptide fragments may be "free-standing" or comprised within a larger polypeptide of which the fragment forms a part or region, most preferably as a single continuous region. Representative examples of polypeptide fragments of the invention, included, for example, fragments that comprise or alternatively, consist of, from about amino acid residues, 1 to 20, 21 to 40, 41 to 60, 61 to 83, 84 to 100, 101 to 120, 121 to 140, 141 to 160, 161 to 180, 181 to 200, 201 to 220, 201 to 224, 210 to 231, 221 to 240, or 241 to 263 of SEQ ID NO:2. Moreover, polypeptide fragments can be at least about 20, 30, 40, 50, 60, 70, 80, 90, 100, 110, 120, 130, 140, 150, 160, 170, 180, 190, 200, 210, 220, 230, 240, 250, 260 amino acids in length. In this context "about" includes the particularly recited ranges, larger or smaller by several (i.e. 5, 4, 3, 2 or 1) amino acids, at either extreme or at both extremes.

In other embodiments, the fragments or polypeptides of the invention (i.e., those described herein) are not larger than 250, 225, 200, 185, 175, 170, 165, 160, 155, 150, 145, 140, 135, 130, 125, 120, 115, 110, 105, 100, 90, 80, 75, 60, 50, 40, 30 or 25 amino acids residues in length.

Additional embodiments encompass polypeptide fragments comprising one, two, three, four, five, or more functional attributes of follistatin-3 polypeptides of the invention, such as, one or more Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index, or any combination thereof, as disclosed in FIG. 3 and in Table I as described herein.

Preferred polypeptides of the invention comprise, or alternatively, consist of amino acid residues 7–16, 34–45, 78–86, 91–100, 108–122, 131–145, 156–169, 184–192, and/or 196–210 of SEQ ID NO:2. Polynucleotides encoding these polypeptides are also encompassed by the invention, as are polynucleotides that hybridize to the complementary strand of these encoding polynucleotides under high stringency conditions (e.g., as described herein) and polypeptides encoded by these hybridizing polynucleotides.

In specific embodiments, polypeptide fragments of the invention comprise, or alternatively, consist of, amino acid residues Leu-14 to Ala-20, Ser-46 to Ile-55, Gly-88 to Pro-97, Gly-113 to Leu-133, Arg-138 to Glu-146, Pro-177 to Thr-191, and/or Gly-219 to Val-237 of SEQ ID NO:2. These polypeptide fragments have been determined to bear antigenic epitopes of the follistatin-3 by the analysis of the Jameson-Wolf antigenic index, as shown in FIG. 3 and Table I, above. Polynucleotides encoding these polypeptides are also encompassed by the invention, as are polynucleotides that hybridize to the complementary strand of these encoding polynucleotides under high stringency conditions (e.g., as described herein) and polypeptides encoded by these hybridizing polynucleotides.

As described in detail below, the polypeptides of the present invention can also be used to raise polyclonal and monoclonal antibodies, which are useful in assays for detecting follistatin-3 expression as described below or as agonists and antagonists capable of enhancing or inhibiting follistatin-3 function. Further, such polypeptides can be used in the yeast two-hybrid system to "capture" follistatin-3 binding proteins which are also candidate agonists and antagonists according to the present invention. The yeast two hybrid system is described by Fields and Song (*Nature* 340:245–246 (1989)).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope". The number of immunogenic epitopes of a protein generally is less than the number of antigenic epitopes (see, for instance, Geysen, et al., *Proc. Natl. Acad. Sci. USA* 81:3998–4002 (1983)).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein (see, for instance, Sutcliffe, J. G., et al., *Science* 219:660–666 (1983)). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention (see, for instance, Wilson, et al., *Cell* 37:767–778 (1984)).

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate follistatin-3-specific antibodies include: a polypeptide comprising amino acid residues: Leu-14 to Ala-20, Ser-46 to Ile-55, Gly-88 to Pro-97, Gly-113 to Leu-133, Arg-138 to Glu-146, Pro-177 to Thr-191, and/or Gly-219 to Val-237 of SEQ ID NO:2. These polypeptide fragments have been determined to bear antigenic epitopes of the follistatin-3 by the analysis of the Jameson-Wolf antigenic index, as shown in FIG. 3 and Table I, above.

The epitope-bearing peptides and polypeptides of the invention may be produced by any conventional means (see, for example, Houghten, R. A., et al., *Proc. Natl. Acad. Sci. USA* 82:5131–5135 (1985); and U.S. Pat. No. 4,631,211 to Houghten, et al. (1986)).

Epitope-bearing peptides and polypeptides of the invention are used to induce antibodies according to methods well known in the art (see, for instance, Sutcliffe, et al., supra; Wilson, et al., supra; Chow, M., et al., *Proc. Natl. Acad. Sci. USA* 82:910–914; and Bittle, F. J., et al., *J. Gen. Virol.* 66:2347–2354 (1985)). Immunogenic epitope-bearing peptides of the invention, i.e., those parts of a protein that elicit an antibody response when the whole protein is the immunogen, are identified according to methods known in the art (see, for instance, Geysen, et al., supra). Further still, U.S. Pat. No. 5,194,392, issued to Geysen, describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092, issued to Geysen, describes a method of detecting or determining a sequence of monomers which is a topographical equivalent of a ligand which is complementary to the ligand binding site of a particular receptor of interest. Similarly, U.S. Pat. No. 5,480,971, issued to Houghten and colleagues, on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

To improve or alter the characteristics of follistatin-3 polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron and colleagues (*J. Biol. Chem.*, 268:2984–2988 (1993)) reported modified KGF proteins that had heparin binding activity even if 3, 8, or 27 N-terminal amino acid residues were missing. In the present case, since the protein of the invention is a member of the inhibin-related polypeptide family, deletions of N-terminal amino acids up to the cysteine at position 12 of SEQ ID NO:2 may retain some biological activity such as binding activin or an activin-like molecule. Polypeptides having further N-terminal deletions including the cysteine-12 residue in SEQ ID NO:2 would not be expected to retain such biological activities because it is known that this residue is likely required for forming a disulfide bridge to provide structural stability which is needed for protein-protein interaction and is in the beginning of the conserved domain required for biological activities.

However, even if deletion of one or more amino acids from the N-terminus of a protein results in modification of loss of one or more biological functions of the protein, other functional or biological activities may still be retained. Thus, the ability of the shortened protein to induce and/or bind to antibodies which recognize the complete or mature of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the follistatin-3 shown in SEQ ID NO:2, up to the cysteine residue at position number 12, and polynucleotides encoding such polypeptides. In particular, the present invention provides polypeptides comprising the amino acid sequence of residues $n^1$-237 of SEQ ID NO:2, where $n^1$ is an integer in the range of −26-$^{12}$, and 12 is the position of the first residue from the N-terminus of the complete follistatin-3 polypeptide (shown in SEQ ID NO:2) believed to be required for activin-binding or activin-like protein-binding activity of the follistatin-3.

More in particular, the invention provides polynucleotides encoding polypeptides having the amino acid sequence of residues of −26-237, −25-237, −24-237, −23-237, −22-237, −21-237, −20-237, −19-237, −18-237, −17-237, −16-237, −15-237, −14-237, −13-237, −12-237, −10-237, −9-237, −8-237, −7-237, −6-237, −5-237, −4-237, −3-237, −2-237, −1-237, 1-237, 2-237, 3-237, 4-237, 5-237, 6-237, 7-237, 8-237, 9-237, 10-237, 11-237, and 12-237 of SEQ ID NO:2. Polynucleotides encoding these polypeptides also are provided.

Similarly, many examples of biologically functional C-terminal deletion muteins are known. For instance, Interferon gamma shows up to ten times higher activities by deleting 8–10 amino acid residues from the carboxy terminus of the protein (Dobeli, et al., *J. Biotechnology* 7:199–216 (1988)). In the present case, since the protein of the invention is a member of the activin-related polypeptide family, deletions of C-terminal amino acids up to the cysteine at position 217 of SEQ ID NO:2 may retain some biological activity such as binding activin or an activin-like molecule. Polypeptides having further C-terminal deletions including the cysteine residue at position 217 of SEQ ID NO:2 would not be expected to retain such biological activities because it is known that this residue is likely required for forming a disulfide bridge to provide structural stability which is needed for protein-protein interactions and is the beginning of the conserved domain required for biological activities.

However, even if deletion of one or more amino acids from the C-terminus of a protein results in modification of loss of one or more biological functions of the protein, other functional or biological activities may still be retained. Thus, the ability of the shortened protein to induce and/or bind to antibodies which recognize the complete or mature form of the protein generally will be retained when less than the majority of the residues of the complete or mature form of the protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the follistatin-3 shown in SEQ ID NO:2, up to the cysteine residue at position 217 of SEQ ID NO:2, and polynucleotides encoding such polypeptides. In particular, the present invention provides polypeptides having the amino acid sequence of residues −26-$m^1$ of the amino acid sequence in SEQ ID NO:2, where m' is any integer in the range of 217 to 237, and residue 217 is the position of the first residue from the C-terminus of the complete follistatin-3 polypeptide (shown in SEQ ID NO:2) believed to be required for the activin-binding or activin-like protein-binding of the follistatin-3.

More in particular, the invention provides polynucleotides encoding polypeptides having the amino acid sequence of residues −26-217, −26-218, −26-219, −26-220, −26-221, −26-222, −26-223, −26-224, −26-225, −26-226, −26-227, −26-228, −26-229, −26-230, −26-231, −26-232, −26-233, −26-234, −26-235, −26-236, and −26-237 of SEQ ID NO:2. Polynucleotides encoding these polypeptides also are provided.

The invention also provides polypeptides having one or more amino acids deleted from both the amino and the carboxyl termini, which may be described generally as having residues $n^1$-$m^1$ of SEQ ID NO:2, where $n^1$ and $m^1$ are integers as described above.

Also included are a nucleotide seqaence encoding a polypeptide consisting of a portion of the complete follistatin-3 amino acid sequence encoded by the cDNA clone contained in ATCC® Deposit No. 209197, where this portion exclude from 1 to abota 37 amino acids from the amino terminus of the complete amino acid sequence encoded by tue cDNA clone contained in ATCC® Depsoit No. 209197, or from 1 to about 20 amino acid from the carboxy terminus, of any cwnbinarion of the above amino terminal and carboxy terminal deletion, of the complete ammo acid sequence encoded by the cDNA clone contdrncd ifl ATCC® Deposit No. 209197. Polynucleotides encoaing all of the above deletion mutant polypeptide forms also are provided.

As mentioned above, even if deletion of one or more amino acids from the N-terminus of a protein results in modification of loss of one or more functions of the protein, other functional or biological activities may still be retained. Thus, the ability of the shortened follistatin-3 mutein to induce and/or bind to antibodies which recognize the complete or mature of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art. It is not unlikely that a follistatin-3 mutein with a large number of deleted N-terminal amino acid residues may retain some biological or immungenic activities. In fact, peptides composed of as few as six follistatin-3 amino acid residues may often evoke an immune response.

Accordingly, the present invention further provides polypeptides having one or more residues deleted from the amino terminus of the follistatin-3 amino acid sequence shown in SEQ ID NO:2, up to the glutamic acid residue at position number 258 and polynucleotides encoding such polypeptides. In particular, the present invention provides polypeptides comprising the amino acid sequence of residues $n^2$-263 of FIGS. 1A, 1B, and 1C (SEQ ID NO:2), where $n^2$ is an integer in the range of 2 to 258, and 259 is the position of the first residue from the N-terminus of the complete follistatin-3 polypeptide believed to be required for at least immunogenic activity of the follistatin-3.

More in particular, the invention provides polynucleotides encoding polypeptides comprising, or alternatively consisting of, the amino acid sequence of residues of R-2 to V-263; P-3 to V-263; G-4 to V-263; A-5 to V-263; P-6 to V-263; G-7 to V-263; P-8 to V-263; L-9 to V-263; W-10 to V-263; P-11 to V-263; L-12 to V-263; P-13 to V-263; W-14 to V-263; G-15 to V-263; A-16 to V-263; L-17 to V-263; A-18 to V-263; W-19 to V-263; A-20 to V-263; V-21 to V-263; G-22 to V-263; F-23 to V-263; V-24 to V-263; S-25 to V-263; S-26 to V-263; M-27 to V-263; G-28 to V-263; S-29 to V-263; G-30 to V-263; N-31 to V-263; P-32 to V-263; A-33 to V-263; P-34 to V-263; G-35 to V-263; G-36 to V-263; V-37 to V-263; C-38 to V-263; W-39 to V-263; L-40 to V-263; Q-41 to V-263; Q-42 to V-263; G-43 to V-263; Q-44 to V-263; E-45 to V-263; A-46 to V-263; T-47 to V-263; C-48 to V-263; S-49 to V-263; L-50 to V-263; V-51 to V-263; L-52 to V-263; Q-53 to V-263; T-54 to V-263; D-55 to V-263; V-56 to V-263; T-57 to V-263; R-58 to V-263; A-59 to V-263; E-60 to V-263; C-61 to V-263; C-62 to V-263; A-63 to V-263; S-64 to V-263; G-65 to V-263; N-66 to V-263; I-67 to V-263; D-68 to V-263; T-69 to V-263; A-70 to V-263; W-71 to V-263; S-72 to V-263; N-73 to V-263; L-74 to V-263; T-75 to V-263; H-76 to V-263; P-77 to V-263; G-78 to V-263; N-79 to V-263; K-80 to V-263; I-81 to V-263; N-82 to V-263; L-83 to V-263; L-84 to V-263; G-85 to V-263; F-86 to V-263; L-87 to V-263; G-88 to V-263; L-89 to V-263; V-90 to V-263; H-91 to V-263; C-92 to V-263; L-93 to V-263; P-94 to V-263; C-95 to V-263; K-96 to V-263; D-97 to V-263; S-98 to V-263; C-99 to V-263; D-100 to V-263; G-101 to V-263; V-102 to V-263; E-103 to V-263; C-104 to V-263; G-105 to V-263; P-106 to V-263; G-107 to V-263; K-108 to V-263; A-109 to V-263; C-110 to V-263; R-111 to V-263; M-112 to V-263; L-113 to V-263; G-114 to V-263; G-115 to V-263; R-116 to V-263; P-117 to V-263; R-118 to V-263; C-119 to V-263; E-120 to V-263; C-121 to V-263; A-122 to V-263; P-123 to V-263; D-124 to V-263; C-125 to V-263; S-126 to V-263; G-127 to V-263; L-128 to V-263; P-129 to V-263; A-130 to V-263; R-131 to V-263; L-132 to V-263; Q-133 to V-263; V-134 to V-263; C-135 to V-263; G-136 to V-263; S-137 to V-263; D-138 to V-263; G-139 to V-263; A-140 to V-263; T-141 to V-263; Y-142 to V-263; R-143 to V-263; D-144 to V-263; E-145 to V-263; C-146 to V-263; E-147 to V-263; L-148 to V-263; R-149 to V-263; A-150 to V-263; A-151 to V-263; R-152 to V-263; C-153 to V-263; R-154 to V-263; G-155 to V-263; H-156 to V-263; P-157 to V-263; D-158 to V-263; L-159 to V-263; S-160 to V-263; V-161 to V-263; M-162 to V-263; Y-163 to V-263; R-164 to V-263; G-165 to V-263; R-166 to V-263; C-167 to V-263; R-168 to V-263; K-169 to V-263; S-170 to V-263; C-171 to V-263; E-172 to V-263; H-173 to V-263; V-174 to V-263; V-175 to V-263; C-176 to V-263; P-177 to V-263; R-178 to V-263; P-179 to V-263; Q-180 to V-263; S-181 to V-263; C-182 to V-263; V-183 to V-263; V-184 to V-263; D-185 to V-263; Q-186 to V-263; T-187 to V-263; G-188 to V-263; S-189 to V-263; A-190 to V-263; H-191 to V-263; C-192 to V-263; V-193 to V-263; V-194 to V-263; C-195 to V-263; R-196 to V-263; A-197 to V-263; A-198 to V-263; P-199 to V-263; C-200 to V-263; P-201 to V-263; V-202 to V-263; P-203 to V-263; S-204 to V-263; S-205 to V-263; P-206 to V-263; G-207 to V-263; Q-208 to V-263; E-209 to V-263; L-210 to V-263; C-211 to V-263; G-212 to V-263; N-213 to V-263; N-214 to V-263; N-215 to V-263; V-216 to V-263; T-217 to V-263; Y-218 to V-263; I-219 to V-263; S-220 to V-263; S-221 to V-263; C-222 to V-263; H-223 to V-263; M-224 to V-263; R-225 to V-263; Q-226 to V-263; A-227 to V-263; T-228 to V-263; C-229 to V-263; F-230 to V-263; L-231 to V-263; G-232 to V-263; R-233 to V-263; S-234 to V-263; I-235 to V-263; G-236 to V-263; V-237 to V-263; R-238 to V-263; H-239 to V-263; A-240 to V-263; G-241 to V-263; S-242 to V-263; C-243 to V-263; A-244 to V-263; G-245 to V-263; T-246 to V-263; P-247 to V-263; E-248 to V-263; E-249 to V-263; P-250 to V-263; P-251 to V-263; G-252 to V-263; G-253 to V-263; E-254 to V-263; S-255 to V-263; A-256 to V-263; E-257 to V-263; and E-258 to V-263 of the follistatin-3 amino acid sequence shown in FIGS. 1A, 1B, and 1C (which is identical to the sequence shown as SEQ ID NO:2, with the exception that the amino acid residues in FIGS. 1A, 1B, and 1C are numbered consecutively from 1 through 263 from the N-terminus to the C-terminus, while the amino acid residues in SEQ ID NO:2 are numbered consecutively from −26 through 237 to reflect the position of the predicted signal peptide). Polynucleotides encoding these polypeptides are also encompassed by the invention.

Also as mentioned above, even if deletion of one or more amino acids from the C-terminus of a protein results in modification of loss of one or more biological functions of the protein, other functional or biological activities may still be retained. Thus, the ability of the shortened follistatin-3 mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that a follistatin-3 mutein with a large number of deleted C-terminal amino acid residues may retain some biological or immungenic activities. In fact, peptides composed of as few as six follistatin-3 amino acid residues may often evoke an immune response.

Accordingly, the present invention further provides polypeptides having one or more residues deleted from the carboxy terminus of the amino acid sequence of the follistatin-3 shown in SEQ ID NO:2, up to the proline residue at position number 6, and polynucleotides encoding such polypeptides. In particular, the present invention provides polypeptides comprising the amino acid sequence of residues 1-$m^2$ of SEQ ID NO:2, where $m^2$ is an integer in the range of 6 to 262, and 6 is the position of the first residue from the C-terminus of the complete follistatin-3 polypeptide believed to be required for at least immunogenic activity of the follistatin-3.

More in particular, the invention provides polynucleotides encoding polypeptides comprising, or alternatively consisting of, the amino acid sequence of residues M-1 to F-262; M-1 to N-261; M-1 to E-260; M-1 to E-259; M-1 to E-258; M-1 to E-257; M-1 to A-256; M-1 to S-255; M-1 to E-254; M-1 to G-253; M-1 to G-252; M-1 to P-251; M-1 to P-250; M-1 to E-249; M-1 to E-248; M-1 to P-247; M-1 to T-246; M-1 to G-245; M-1 to A-244; M-1 to C-243; M-1 to S-242; M-l to G-241; M-1 to A-240; M-1 to H-239; M-1 to R-238; M-1 to V-237; M-1 to G-236; M-1 to 1–235;M-1 to S-234; M-1 to R-233; M-1 to G-232; M-1 to L-231; M-1 to F-230; M-1 to C-229; M-1 to T-228; M-1 to A-227; M-1 to Q-226; M-1 to R-225; M-1 to M-224; M-1 to H-223; M-1 to C-222; M-1 to S-221; M-1 to S-220; M-1 to I-219; M-1 to Y-218; M-1 to T-217; M-1 to V-216; M-1 to N-215; M-1 to N-214; M-1 to N-213; M-1 to G-212; M-1 to C-211; M-1 to L-210; M-1 to E-209; M-1 to Q-208; M-1 to G-207; M-1 to P-206; M-1 to S-205; M-1 to S-204; M-1 to P-203; M-1 to V-202; M-1 to-P-201; M-1 to C-200; M-1 to P-199; M-1 to A-198; M-1 to A-197; M-1 to R-196; M-1 to C-195; M-1 to V-194; M-1 to V-193; M-1 to C-192; M-1 to H-191; M-1 to A-190; M-1 to S-189; M-1 to G-188; M-1 to T-187; M-1 to Q-186; M-1 to D-185; M-1 to V-184; M-1 to V-183; M-1 to C-182; M-1 to S-181; M-1 to Q-180; M-1 to P-179; M-1 to R-178; M-1 to P-177; M-1 to C-176; M-1 to V-175; M-1 to V-174; M-1 to H-173; M-1 to E-172; M-1 to C-171; M-1 to S-170; M-1 to K-169; M-1 to R-168; M-1 to C-167; M-1 to R-166; M-1 to G-165; M-1 to R-164; M-1 to Y-163; M-1 to M-162; M-1 to V-161; M-1 to S-160; M-1 to L-159; M-1 to D-158; M-1 to P-157; M-1 to H-156; M-1 to G-155; M-1 to R-154; M-1 to C-153; M-1 to R-152; M-1 to A-151; M-1 to A-150; M-1 to R-149; M-1 to L-148; M-1 to E-147; M-1 to C-146; M-1 to E-145; M-1 to D-144; M-1 to R-143; M-1 to Y-142; M-1 to T-141; M-1 to A-140; M-1 to G-139; M-1 to D-138; M-1 to S-137; M-1 to G-136; M-1 to C-135; M-1 to V-134; M-1 to Q-133; M-1 to L-132; M-1 to R-131; M-1 to A-130; M-1 to P-129; M-1 to L-128; M-1 to G-127; M-1 to S-126; M-1 to C-125; M-1 to D-124; M-1 to P-123; M-1 to A-122; M-1 to C-121; M-1 to E-120; M-1 to C-i 19; M-1 to R-118; M-1 to P-117; M-1 to R-116; M-1 to G-115; M-1 to G-114; M-1 to L-113; M-1 to M-112; M-1 to R-111; M-1 to C-110; M-1 to A-109; M-1 to K-108; M-1 to G-107; M-1 to P-106; M-1 to G-105; M-1 to C-104; M-1 to E-103; M-1 to V-102; M-1 to G-101; M-1 to D-100; M-1 to C-99; M-1 to S-98; M-1 to D-97; M-1 to K-96; M-1 to C-95; M-1 to P-94; M-1 to L-93; M-1 to C-92; M-1 to H-91; M-1 to V-90; M-1 to L-89; M-1 to G-88; M-1 to L-87; M-1 to F-86; M-1 to G-85; M-1 to L-84; M-1 to L-83; M-1 to N-82; M-1 to I-81; M-1 to K-80; M-1 to N-79; M-1 to G-78; M-1 to P-77; M-1 to H-76; M-1 to T-75; M-1 to L-74; M-1 to N-73; M-1 to S-72; M-1 to W-71; M-1 to A-70; M-1 to T-69; M-1 to D-68; M-1 to I-67; M-1 to N-66; M-1 to G-65; M-1 to S-64; M-1 to A-63; M-1 to C-62; M-1 to C-61; M-1 to E-60; M-1 to A-59; M-1 to R-58; M-1 to T-57; M-1 to V-56; M-1 to D-55; M-1 to T-54; M-1 to Q-53; M-1 to L-52; M-1 to V-51; M-1 to L-50; M-1 to S-49; M-1 to C-48; M-1 to T-47; M-1 to A-46; M-1 to E-45; M-1 to Q-44; M-1 to G-43; M-1 to Q-42; M-1 to Q-41; M-1 to L-40; M-1 to W-39; M-1 to C-38; M-1 to V-37; M-1 to G-36; M-1 to G-35; M-1 to P-34; M-1 to A-33; M-1 to P-32; M-1 to N-31; M-1 to G-30; M-1 to S-29; M-1 to G-28; M-1 to M-27; M-1 to S-26; M-1 to S-25; M-1 to V-24; M-1 to F-23; M-1 to G-22; M-1 to V-21; M-1 to A-20; M-1 to W-19; M-1 to A-18; M-1 to L-17; M-1 to A-16; M-1 to G-15; M-l to W-14; M-1 to P-13; M-1 to L-12; M-1 to P-11; M-1 to W-10; M-1 to L-9; M-1 to P-8; M-1 to G-7; M-1 to P-6 of the sequence of the follistatin-3 sequence shown in FIGS. 1A, 1B, and 1C (which is identical to the sequence shown as SEQ ID NO:2, with the exception that the amino acid residues in FIGS. 1A, 1B, and 1C are numbered consecutively from 1 through 263 from the N-terminus to the C-terminus, while the amino acid residues in SEQ ID NO:2 are numbered consecutively from −26 through 237 to reflect the position of the predicted signal peptide). Polynucleotides encoding these polypeptides also are provided.

The invention also provides polypeptides having one or more amino acids deleted from both the amino and the carboxyl termini of a follistatin-3 polypeptide, which may be described generally as having residues $n^2$-$m^2$ of FIGS. 1A, 1B, and 1C (SEQ ID NO:2), where $n^2$ and $m^2$ are integers as described above.

In addition to terminal deletion forms of the protein discussed above, it also will be recognized by one of ordinary skill in the art that some amino acid sequences of the follistatin-3 polypeptide can be varied without significant effect of the structure or function of the protein. If such differences in sequence are contemplated, it should be remembered that there will be critical areas on the protein which determine activity.

Thus, the invention further includes variations of the follistatin-3 polypeptide which show substantial follistatin-3 polypeptide activity or which include regions of follistatin-3 such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided wherein the authors indicate that there are two main approaches for studying the tolerance of an amino acid sequence to change (Bowie, J. U., et al., *Science* 247:1306–1310 (1990)),. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side chains are generally conserved. Other such phenotypically silent substitutions are described by Bowie and coworkers (supra) and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the follistatin-3 of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table II).

TABLE II

| Conservative Amino Acid Substitutions. | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Embodiments of the invention are directed to polypeptides which comprise the amino acid sequence of a follistatin-3 polypeptide described herein, but having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions, when compared with the follistatin-3 polynucleotide sequence described herein. Of course, in order of ever-increasing preference, it is highly preferable for a peptide or polypeptide to have an amino acid sequence which comprises the amino acid sequence of a follistatin-3 polypeptide, which contains at least one, but not more than 10, 9, 8, 7, 6, 5, 4, 3, 2 or 1 conservative amino acid substitutions.

In further specific embodiments, the number of substitutions, additions or deletions in the amino acid sequence of FIGS. 1A, 1B, and 1C (SEQ ID NO:2), a polypeptide sequence encoded by the deposited clones, and/or any of the polypeptide fragments described herein is 75, 70, 60, 50, 40, 35, 30, 25, 20, 15, 10, 9, 8, 7, 6, 5, 4, 3, 2, 1 or 150–50, 100–50, 50–20, 30–20, 20–15, 20–10, 15–10, 10–1, 5–10, 1–5, 1–3 or 1–2.

To improve or alter the characteristics of follistatin-3 polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Thus, the invention also encompasses follistatin-3 derivatives and analogs that have one or more amino acid residues deleted, added, or substituted to generate follistatin-3 polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to acheive, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognitions sequences in the follistatin-3 polypeptides of the invention, and/or an amino acid deletion at the second position of any one or more such recognition sequences will prevent glycosylation of the follistatin-3 polypeptide at the modified tripeptide sequence (see, e.g., Miyajima, A., et al., *EMBO J.* 5(6): 1193–1197 (1986)).

Amino acids in-the follistatin-3 polypeptides of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard, et al., *Clin. Exp. Immunol.* 2:331–340 (1967); Robbins, et al., *Diabetes* 36:838–845 (1987); Cleland, et al., *Crit. Rev. Therapeutic Drug Carrier Systems* 10:307–377. (1993)).

A mutational analysis of the two N-linked glycosylation sites (Asn-95 and Asn-259) of follistatin-1 was conducted by Inouye and colleagues (*Biochem. Biophys. Res. Comm.* 179:352–358 (1991)). As described in the analysis, disruption of either or both of the N-linked glycosylation sites (by mutation of Thr-97 and Thr-261 to alanine) had no discernable effect on activin-binding and FSH secretion. However, results of the same study suggest that insertion of two amino acid residues (lysine and leucine) between residues Asn-2 and Cys-3 of follistatin-1 completely abolishes its inhibitory activity on FSH secretion from the pituitary, as well as its ability to bind activin. The asparagine and surrounding residues described in this analysis are weakly conserved between follistatin-1 and follistatin-3. There are however, two potential N-linked glycosylation sites in the sequence of follistatin-3 (N-73 and N-215; see FIG. 1A). In addition, 4 out of 5 amino acids making up the sequence near the amino terminus, at which point Inouye and coworkers made their two amino acid insertion (supra), are conserved. Consequently, the extreme amino terminal region of the predicted mature follistatin-3 polypeptide may have a high potential for exhibiting a deleterious effect through mutation.

The polypeptides of the present invention are preferably provided in an isolated form, and preferably are substantially purified. A recombinantly produced version of the follistatin-3 polypeptide can be substantially purified by the one-step method described by Smith and Johnson (*Gene* 67:31–40 (1988)). Polypeptides of the invention also can be purified from natural or recombinant sources using anti-Follistatin-3 antibodies of the invention in methods which are well known in the art of protein purification.

The invention further provides an isolated follistatin-3 polypeptide comprising an amino acid sequence selected from the group consisting of: (a) the amino acid sequence of the full-length follistatin-3 polypeptide having the complete amino acid sequence shown in SEQ ID NO:2 (i.e., positions −26 to 237 of SEQ ID NO:2); (b) the amino acid sequence of the full-length follistatin-3 polypeptide having the complete amino acid sequence shown in SEQ ID NO:2 excepting the N-terminal methionine (i.e., positions −25 to 237 of SEQ ID NO:2); (c) the amino acid sequence of the predicted mature follistatin-3 polypeptide having the amino acid sequence at positions 1 to 237 in SEQ ID NO:2; (d) the amino acid sequence of the full-length follistatin-3 polypeptide having the complete amino acid sequence encoded by the cDNA clone contained in ATCC® 4 Deposit No. 209197; (e) the amino acid sequence of the full-length follistatin-3 polypeptide having the complete amino acid sequence excepting the N-terminal methionine encoded by the cDNA clone contained in ATCC® Deposit No. 209197; and (t) the amino acid sequence of the mature follistatin-3 polypeptide having the amino acid sequence encoded by the cDNA clone contained in ATCC® Deposit No. 209197. The polypeptides of the present invention also include polypeptides having an amino acid sequence at least 80% identical, more preferably at least 90% identical, arid still more preferably 95%, 96%, 97%, 98% or 99% identical to those described in (a), (b), (c), (d), (e) or (f) above, as well as polypeptides having an amino acid sequence with at least 90% similarity, and more preferably at least 95% similarity, to chose above.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited cDNA or to the polypeptide of SEQ ID NO:2, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of a follistatin-3 polypeptide is intended that the amino acid sequence of the polypeptide is identical to the reference sequence except that the polypeptide sequence may include up to five amino acid alterations per each 100 amino acids of the reference amino acid of the follistatin-3 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A, 1B, and 1C (SEQ ID NO:2), the amino acid sequence encoded by deposited cDNA clone HDTAH85, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The invention also encompasses fusion proteins in which the full-length follistatin-3 polypeptide or fragment, variant, derivative, or analog thereof is fused to an unrelated protein. These fusion proteins can be routinely designed on the basis of the follistatin-3 nucleotide and polypeptide sequences disclosed herein. For example, as one of skill in the art will appreciate, follistatin-3 polypeptides and fragments (including epitope-bearing fragments) thereof described herein can be combined with parts of the constant domain of immunoglobulins (IgG), resulting in chimeric (fusion) polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker, et al., *Nature* 331:84–86 (1988)). Fusion proteins that have a disulfide-linked dimeric structure due to the IgG part can also be more efficient in binding and neutralizing other molecules than the monomeric follistatin-3 polypeptide or polypeptide fragments alone (Fountoulakis, et al., *J. Biochem.* 270:3958–3964 (1995)). Examples of follistatin-3 fusion proteins that are encompassed by the invention include, but are not limited to, fusion of the follistatin-3 polypeptide sequences to any amino acid sequence that allows the fusion proteins to be displayed on the cell surface (e.g. the IgG Fc domain); or fusions to an enzyme, fluorescent protein, or luminescent protein which provides a marker function.

The polypeptides of the present invention have uses which include, but are not limited to, a molecular weight marker on SDS-PAGE gels or on molecular sieve gel filtration columns using methods well known to those of skill in the art. Additionally, as described in detail herein, the polypeptides of the present invention can also be used to raise polyclonal and monoclonal antibodies, which are useful in assays for detecting follistatin-3 expression as described below or as agonists and antagonists capable of enhancing or inhibiting follistatin-3 function. Further, such polypeptides can be used in the yeast two-hybrid system to "capture" follistatin-3 polypeptide binding proteins which are also candidate agonists and antagonists according to the present invention. The yeast two hybrid system is described by Fields and Song (*Nature* 340:245–246 (1989)).

Antibodies

Follistatin-3 polypeptide-specific antibodies for use in the present invention can be raised against the intact follistatin-3 polypeptide or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to follistatin-3. Fab and F(ab')2 fragments lack the Fc fragment of intact antibody, clear more rapidly from the circulation, and may have less non-specific tissue binding of an intact antibody (Wahl, et al., *J. Nucl. Med.* 24:316–325 (1983)). Thus, these fragments are preferred.

The antibodies of the present invention may be prepared by any of a variety of methods. For example, cells expressing the follistatin-3 or an antigenic fragment thereof can be administered to an animal in order to induce the production of sera containing polyclonal antibodies. In a preferred method, a preparation of follistatin-3 polypeptide is prepared and purified to render it substantially free of natural contaminants. Such a preparation is then introduced into an animal in order to produce polyclonal antisera of greater specific activity.

In the most preferred method, the antibodies of the present invention are monoclonal antibodies (or follistatin-3 binding fragments thereof). Such monoclonal antibodies can be prepared using hybridoma technology (Kohler, et al., Nature 256:495 (1975); Kohler, et al., *Eur. J. Immunol.* 6:511 (1976); Kohler, et al., *Eur. J. Immunol.* 6:292 (1976); Hammerling, et al., in: *Monoclonal Antibodies and T-Cell Hybridomas*, Elsevier, N.Y., (1981) pp. 563–681)). In general, such procedures involve immunizing an animal (preferably a mouse) with a follistatin-3 antigen or, more preferably, with a follistatin-3-expressing cell. Suitable cells can be recognized by their capacity to bind anti-Follistatin-3 antibody. Such cells may be cultured in any suitable tissue culture medium; however, it is preferable to culture cells in Earle's modified Eagle's medium supplemented with 10% fetal bovine serum (inactivated at about 56° C), and supplemented with about 10 μg/ml of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, Rockville, Md. After fusion, the resulting hybridoma cells are selectively maintained in HAT medium, and then cloned by limiting dilution as described by Wands and colleagues (*Gastroenterology* 80:225–232 (1981)). The hybridoma cells obtained through such a selection are then assayed to identify clones which secrete antibodies capable of binding the follistatin-3 antigen.

Alternatively, additional antibodies capable of binding to the follistatin-3 antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, follistatin-3-specific antibodies are used to immunize an animal, preferably a mouse. The splenocytes of such an animal are then used to produce hybridoma cells, and the hybridoma cells are screened to identify clones which produce an antibody whose ability to bind to the follistatin-3-specific antibody can be blocked by the follistatin-3 antigen. Such antibodies comprise anti-idiotypic antibodies to the follistatin-3-specific antibody and can be used to immunize an animal to induce formation of further follistatin-3-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, follistatin-3-binding fragments can be produced through the application of recombinant DNA technology or through synthetic chemistry.

For in vivo use of anti-Follistatin-3 in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art (Morrison, *Science* 229:1202 (1985); Oi, et al., *BioTechniques* 4:214 (1986); Cabilly, et al., U.S. Pat. No. 4,816,567; Taniguchi, et al., EP 171496; Morrison, et al., EP 173494; Neuberger, et al., WO 8601533; Robinson, et al., WO 8702671; Boulianne, et al., *Nature* 312:643 (1984); Neuberger, et al., *Nature* 314:268 (1985).

Reproductive System—and Cell Growth and Differentiation-Related Disorders

Diagnosis

The present inventors have discovered that follistatin-3 is expressed not only in Hodgkin's Lymphoma, but also in synovial fibroblasts, gall bladder, resting and serum-induced smooth muscle, testes, Merkel cells, HEL cells, hippocampus, TNF-α-and IFN-induced epithelial cells, keratinocyte, amygdala depression, HL-60 cells, hepatoma, progesterone-treated epidermal cells, endothelial cells, HSC 172 cells, epithelioid sarcoma, activated T-cells, breast lymph node, pancreatic carcinoma, fetal dura mater, fetal lung, epididymis, placenta, dendritic cells, rejected kidney, and uterine cancer. For a number of reproductive system-related disorders and disorders related to the regulation of cell growth and differentiation, substantially altered (increased or decreased) levels of follistatin-3 gene expression can be detected in reproductive system tissue or other cells or bodily fluids (e.g., sera, plasma, urine, synovial fluid or spinal fluid) taken from an individual having such a disorder, relative to a "standard" follistatin-3 gene expression level, that is, the follistatin-3 expression level in reproductive system tissues or bodily fluids from an individual not having the reproductive system or cell growth and differentiation disorder. Thus, the invention provides a diagnostic method useful during diagnosis of a reproductive system or cell growth and differentiation disorder, which involves measuring the expression level of the gene encoding the follistatin-3 polypeptide in reproductive system tissue or other cells or body fluid from an individual and comparing the measured gene expression level with a standard-follistatin-3 gene expression level, whereby an increase or decrease in the gene expression level compared to the standard is indicative of a reproductive or cell growth and differentiation system disorder.

In particular, it is believed that certain tissues in mammals with cancer of various cells and tissues of the reproductive or other systems express significantly reduced levels of the follistatin-3 polypeptide and mRNA encoding the follistatin-3 polypeptide when compared to a corresponding "standard" level. Further, it is believed that enhanced levels of the follistatin-3 polypeptide can be detected in certain body fluids (e.g., sera, plasma, urine, and spinal fluid) from mammals with such a cancer when compared to sera from mammals of the same species not having the cancer.

Thus, the invention provides a diagnostic method useful during diagnosis of reproductive system or cell growth and differentiation disorders, including cancers of these systems, which involves measuring the expression level of the gene encoding the follistatin-3 polypeptide in reproductive system tissue or other cells or body fluid from an individual and comparing the measured gene expression level with a standard follistatin-3 gene expression level, whereby an increase or decrease in the gene expression level compared to the standard is indicative of a reproductive system disorder or a disorder of the regulation of cell growth and differentiation.

Where a diagnosis of a disorder in the reproductive or other system including diagnosis of a tumor, has already been made according to conventional methods, the present invention is useful as a prognostic indicator, whereby patients exhibiting depressed follistatin-3 gene expression will experience a worse clinical outcome relative to patients expressing the gene at a level nearer the standard level.

By "assaying the expression level of the gene encoding the follistatin-3 polypeptide" is intended qualitatively or quantitatively measuring or estimating the level of the follistatin-3 polypeptide or the level of the mRNA encoding the follistatin-3 polypeptide in a first biological sample either directly (e.g., by determining or estimating absolute polypeptide level or mRNA level) or relatively (e.g., by comparing to the follistatin-3 polypeptide level or mRNA level in a second biological sample). Preferably, the follistatin-3 polypeptide level or mRNA level in the first biological sample is measured or estimated and compared to a standard follistatin-3 polypeptide level or mRNA level, the standard being taken from a second biological sample obtained from an individual not having the disorder or being determined by averaging levels from a population of individuals not having a disorder of the reproductive system or of regulation of cell growth and differentiation. As will be appreciated in the art, once a standard follistatin-3 polypeptide level or mRNA level is known, it can be used repeatedly as a standard for comparison.

By "biological sample" is intended any biological sample obtained from an individual, body fluid, cell line, tissue culture, or other source which contains follistatin-3 polypeptide or mRNA. As indicated, biological samples include body fluids (such as sera, plasma, urine, synovial fluid and spinal fluid) which contain free follistatin-3 polypeptide, reproductive system tissue, and other tissue sources found to express complete or mature follistatin-3 or a follistatin-3 receptor. Methods for obtaining tissue biopsies and body fluids from mammals are well known in the art. Where the biological sample is to include mRNA, a tissue biopsy is the preferred source.

The present invention is useful for diagnosis or treatment of various reproductive system-related disorders and disorders of the regulation of cell growth and differentiation in mammals, preferably humans. Such disorders include tumors, cancers, interstitial lung disease, and any disregulation of the growth and differentiation patterns of cell function including, but not limited to, autoimmunity, arthritis, leukemias, lymphomas, immunosuppression, immunity, humoral immunity, inflammatory bowel disease, myelosuppression and the like.

Total cellular RNA can be isolated from a biological sample using any suitable technique such as the single-step guanidinium-thiocyanate-phenol-chloroform method described by Chomczynski and Sacchi (*Anal. Biochem.* 162:156–159 (1987)). Levels of mRNA encoding the follistatin-3 polypeptide are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying follistatin-3 polypeptide levels in a biological sample can occur using antibody-based techniques. For example, follistatin-3 polypeptide expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting follistatin-3 polypeptide gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying follistatin-3 polypeptide levels in a biological sample obtained from an individual, follistatin-3 polypeptide can also be detected in vivo by imaging. Antibody labels or markers for in vivo imaging of follistatin-3 polypeptide include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A follistatin-3 polypeptide-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain follistatin-3 polypeptide. In vivo tumor imaging is described by Burchiel and coworkers (Chapter 13 in *Tumor Imaging: The Radiochemical Detection of Cancer*, Burchiel, S. W. and Rhodes, B. A., eds., Masson Publishing Inc. (1982)).

Treatment

As noted above, follistatin-3 polynucleotides and polypeptides are useful for diagnosis of conditions involving abnormally high or low expression of follistatin-3 activities. Given the cells and tissues where follistatin-3 is expressed as well as the activities modulated by follistatin-3, it is readily apparent that a substantially altered (increased or decreased) level of expression of follistatin-3 in an individual compared to the standard or "normal" level produces pathological conditions related to the bodily system(s) in which follistatin-3 is expressed and/or is active.

It will also be appreciated by one of ordinary skill that, since the follistatin-3 polypeptide of the invention is a member of the inhibin-related protein family the mature secreted form of the protein may be released in soluble form from the cells which express the follistatin-3 by proteolytic cleavage. Therefore, when follistatin-3 mature form is added from an exogenous source to cells, tissues or the body of an individual, the protein will exert its physiological activities on its target cells of that individual.

Therefore, it will be appreciated that conditions caused by a decrease in the standard or normal level of Follistatin-3 activity in an individual, particularly disorders of the reproductive system, can be treated by administration of follistatin-3 polypeptide (in the form of the mature protein). Thus, the invention also provides a method of treatment of an individual in need of an increased level of follistatin-3 activity comprising administering to such an individual a pharmaceutical composition comprising an amount of an isolated follistatin-3 polypeptide of the invention, particularly a mature form of the follistatin-3 protein of the invention, effective to increase the follistatin-3 activity level in such an individual.

Follistatin-3 may be used to treat male sterility by its innate ability to bind activin and, as a result, prevent activin-binding to its receptor. Activin receptor-binding results in a suppression of FSH secretion. Increased levels of FSH, in turn, result in an increase in spermatogenesis (Ying, S.-Y. *Endocrine Rev*. 9:267–293 (1988)). Thus, a decrease in the effective concentration of activin will result in an FSH-mediated increase in spermatogenesis. In addition, since activin elicits a number of biological effects including the modulation of gonadal androgen biosynthesis (Hsueh, A. J. W., et al., *Proc. Natl. Acad. Sci. USA* 84:5082–5086 (1987)), the attenuation of growth hormone secretion (Bilezikjian, L. M., et al., *Endocrinology* 126:2369–2376 (1990), the promotion of erythroid cell differentiation (Eto, Y., et al., *Biochem. Biophys. Res. Comm*. 142:1095–1103 (1987)), the induction of mesoderm formation (Smith, J. C., et al., *Nature* 345:729–731 (1990)), and the maintenance of nerve cell survival (Schubert, D., et al., *Nature* 344:868–870 (1990)), and since follistatin-3 directly inhibits activin acitivity, follistatin-3 may be used to therapeutically regulate, as well as diagnostically evaluate, the conditions and events listed above. Follistatin-3 may also be used to inhibit the activin-induced differentiation of follicular granulosa cells (Nakamura, T., et al., *Biochim. Biophys. Acta* 1135:103–109 (1992)). Follistatin-3 may be used therapeutically to regulate autocrine endothelial cell activity and, as a result, induce angiogenesis (Kozian, D. H., et al., *Lab. Invest*. 76:267–276 (1997)). Follistatin-3 may also be used to inhibit the activity of activin and thereby prevent the observed activin-mediated inhibition of basal and androgen-stimulated proliferation and induction of apoptosis (Wang, Q. F., et al., *Endocrinology* 137:5476–5483 (1996)). Treatment to increase the expression or the presence of follistatin-3 may be used to inhibit the progression of gonadotroph adenomas, osteosarcomas, hepatomas, and other tumors and cancers including bone, breast, colon, lymphomas, leukemias, epithelial carcinomas, pancreatic, stomach, liver, lung, melanoma, prostate, ovarian, uterine, bladder, gliomas, retinoblastomas, sarcomas, and the like (Penabad, J. L., et al., *J. Clin. Endocrinol. Metab*. 81:3397–3403 (1996); Kato, M. V., et al., *Oncogene* 12:1361–1364 (1996)). Follistatin-3 may also be employed to stimulate wound healing. In this same manner, follistatin-3 may also be employed to treat other fibrotic disorders, including liver cirrhosis, osteoarthritis and pulmonary fibrosis. Follistatin-3 also increases the presence of eosinophils which have the distinctive function of killing the larvae of parasites that invade tissues, as in schistosomiasis, trichinosis and ascariasis. It may also be employed to regulate hematopoiesis, by regulating the activation and differentiation of various hematopoietic progenitor cells, for example, to release mature leukocytes from the bone marrow following chemotherapy, i.e., in stem cell mobilization. Follistatin-3 may also be employed to treat sepsis. Follistatin-3 may also be used to treat a number of disease states known to those of skill in the art which may be therapeutically regulated by exploiting the prohibitive interation of follistatin-3 with the activin molecule.

Formulations and Administration

The follistatin-3 polypeptide composition will be formulated and dosed in a fashion consistent with good medical practice, taking into account the clinical condition of the individual patient (especially the side effects of treatment with follistatin-3 polypeptide alone), the site of delivery of the follistatin-3 polypeptide composition, the method of administration, the scheduling of administration, and other factors known to practitioners. The "effective amount" of follistatin-3 polypeptide for purposes herein is thus determined by such considerations.

As a general proposition, the total pharmaceutically effective amount of follistatin-3 polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the follistatin-3 polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the follistatin-3 of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The follistatin-3 polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U., et al., *Biopolymers* 22:547–556 (1983)), poly (2-hydroxyethyl methacrylate; Langer, R., et al., *J. Biomed. Mater. Res*. 15:167–277 (1981), and Langer, R., *Chem. Tech*. 12:98–105 (1982)), ethylene vinyl acetate (Langer, R., et al., Id.) or poly-D-(−)-3-hydroxybutyric acid (EP 133,988). Sustained-release follistatin-3 polypeptide compositions also include liposomally entrapped follistatin-3 polypeptide. Liposomes containing follistatin-3 polypeptide are prepared by methods known in the art (DE 3,218,121; Epstein, et al., *Proc. Natl. Acad. Sci*. (*USA*) 82:3688–3692 (1985); Hwang, et al., *Proc. Natl. Acad. Sci*. (*USA*) 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324). Ordinarily, the liposomes are of the small (about 200–800 Angstroms) unilamellar type in which the lipid content is greater than about 30 mol. percent cholesterol, the selected proportion being adjusted for the optimal follistatin-3 polypeptide therapy.

For parenteral administration, in one embodiment, the follistatin-3 polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the follistatin-3 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The follistatin-3 polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of follistatin-3 polypeptide salts.

Follistatin-3 polypeptide to be used for therapeutic administration must be sterile. Sterility is readily accomplished by filtration through sterile filtration membranes (e.g., 0.2 micron membranes). Therapeutic follistatin-3 polypeptide compositions generally are placed into a container having a sterile access port, for example, an intravenous solution bag or vial having a stopper pierceable by a hypodermic injection needle.

Follistatin-3 polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous follistatin-3 polypeptide solution, and the resulting mixture is lyophilized. The infusion solution is prepared by reconstituting the lyophilized follistatin-3 polypeptide using bacteriostatic water-for-injection (WFI).

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of follistatin-3 on cells, such as its interaction with follistatin-3-binding molecules such as activin, an activin-like molecule, or a follistatin-3 receptor molecule. An agonists is a compound which increases the natural biological functions of follistatin-3 or which functions in a manner similar to follistatin-3, while antagonists decrease or eliminate such functions.

In another aspect of this embodiment the invention provides a method for identifying an activin-like molecule or a receptor protein or other ligand-binding protein which binds specifically to a follistatin-3 polypeptide. For example, a cellular compartment, such as a membrane or a preparation thereof, may be prepared from a cell that expresses a molecule that binds follistatin-3. The preparation is incubated with labeled follistatin-3 and complexes of follistatin-3 bound to the activin-like molecule, receptor or other binding protein are isolated and characterized according to routine methods known in the art. Alternatively, the follistatin-3 polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds follistatin-3, such as a molecule of a signaling or regulatory pathway modulated by follistatin-3. The preparation is incubated with labeled follistatin-3 in the absence or the presence of a candidate molecule which may be a follistatin-3 agonists or antagonist. The ability of the candidate molecule to bind the binding molecule is reflected in decreased binding of the labeled ligand. Molecules which bind gratuitously, i.e., without inducing the effects of follistatin-3 on binding the follistatin-3 binding molecule, are most likely to be good antagonists. Molecules that bind well and elicit effects that are the same as or closely related to follistatin-3 are agonists.

Follistatin-3-like effects of potential agonists and antagonists may by measured, for instance, by determining activity of a second messenger system following interaction of the candidate molecule with a cell or appropriate cell preparation, and comparing the effect with that of follistatin-3 or molecules that elicit the same effects as follistatin-3. Second messenger systems that may be useful in this regard include but are not limited to AMP guanylate cyclase, ion channel or phosphoinositide hydrolysis second messenger systems.

Another example of an assay for follistatin-3 antagonists is a competitive assay that combines follistatin-3 and a potential antagonist with membrane-bound follistatin-3 receptor molecules or recombinant follistatin-3 receptor molecules under appropriate conditions for a competitive inhibition assay. Follistatin-3 can be labeled, such as by radioactivity, such that the number of follistatin-3 molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing follistatin-3-induced activities, thereby preventing the action of follistatin-3 by excluding follistatin-3 from binding.

Other potential antagonists include antisense molecules. Antisense technology can be used to control gene expression through antisense DNA or RNA or through triple-helix formation. Antisense techniques are discussed in a number of studies (for example, Okano, *J. Neurochem.* 56:560 (1991); "Oligodeoxynucleotides as Antisense Inhibitors of Gene Expression." CRC Press, Boca Raton, Fla. (1988)). Triple helix formation is discussed in a number of studies, as well (for instance, Lee, et al., *Nucleic Acids Research* 6:3073 (1979); Cooney, et al., *Science* 241:456 (1988); Dervan, et al., *Science* 251:1360 (1991)). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of follistatin-3. The antisense RNA oligonucleotide hybridizes to the mRNA in vivo and blocks translation of the mRNA molecule into follistatin-3 polypeptide. The oligonucleotides described above can also be delivered to cells such that the antisense RNA or DNA may be expressed in vivo to inhibit production of follistatin-3.

The agonists and antagonists may be employed in a composition with a pharmaceutically acceptable carrier, e.g., as described above.

Antagonists of follistatin-3 may be employed, for instance, to treat a deficiency in FSH, estrogen, and other hormones. Follistatin-1 and follistatin-3 are potent inhibitors of FSH and estrogen production and secretion. As a result, a deficiency of these or related hormones may be corrected or ameliorated through the use of a follistatin-3 antagonist. A follistatin-3 antagonist may be used to prevent or inhibit or reduce the production of spermatozoa by inhibiting the interaction of follistatin-3 with activin. Antagonists of follistatin-3 may also be used to modulate gonadal androgen biosynthesis, attenuate growth hormone secretion, promote the differentiation of follicular granulosa, erythroid, and other cell types, induce mesoderm formation, and increase the survival of nerve cells. A follistatin-3 antagonist may be used to inhibit angiogenesis related to or independent of tumorigenesis. Follistatin-3 antagonists may also be useful in increasing the activity of activin and thereby increasing the observed activin-mediated inhibition of basal and androgen-stimulated proliferation and induction of apoptosis. Antagonists of follistatin-3 may be used to regulate the hormonal and growth factor environment, and consequently, the activity of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes. The antagonists may also be employed to treat infectious diseases including silicosis, sarcoidosis, idiopathic pulmonary fibrosis by alterring the activation state of mononuclear phagocytes. They may also be employed to treat idiopathic hyper-eosinophilic syndrome by preventing eosinophil production and activation. Endotoxic shock may also be treated by the antagonists by preventing the activation of macrophages. Any of the above antagonists may be employed in a composition with a pharmaceutically acceptable carrier, e.g., as hereinafter described.

Gene Mapping

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a follistatin-3 gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp (for a review of this technique, see Verma, et al., *Human Chromosomes: A Manual Of Basic Techniques*, Pergamon Press, New York. (1988)).

Once a sequence has been mapped to a precise chromosomal location, the physical position of the sequence on the chromosome can be correlated with genetic map data. Such data are found, for example, on the World Wide Web (McKusick, V. *Mendelian Inheritance In Man*, available on-line through Johns Hopkins University, Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1(a)

Expression and Purification of "His-tagged" Follistatin-3 in *E. coli*

The bacterial expression vector pHE-4 is used for bacterial expression in this example. pHE-4 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6× His tag") covalently linked to the amino terminus of that polypeptide.

The DNA sequence encoding the desired portion of follistatin-3 comprising the mature form of the follistatin-3 amino acid sequence is amplified from the deposited cDNA clone using PCR oligonucleotide primers which anneal to the amino terminal sequences of the desired portion of follistatin-3 and to sequences in the deposited construct 3' to the cDNA coding sequence. Additional nucleotides containing restriction sites to facilitate cloning in the pHE-4 vector are added to the 5' and 3' primer sequences, respectively.

For cloning the mature form of the follistatin-3 protein, the 5' primer has the sequence 5' TCA CGC CAT ATG GGC TCG GGG AAC C 3' (SEQ ID NO:12) containing the underlined Nde I restriction site followed by 16 nucleotides of the amino terminal coding sequence of the mature follistatin-3 sequence in SEQ ID NO:2. One of ordinary skill in the art would appreciate, of course, that the point in the protein coding sequence where the 5' primer begins may be varied to amplify a DNA segment encoding any desired portion of the complete follistatin-3 protein shorter or longer than the mature form of the protein. The 3' primer has the sequence 5' CAT CCG GGTACC TTA TTA CAC GAA GTT CTC TTC CTC TTC TG 3' (SEQ ID NO:13) containing the underlined Asp 718 restriction site followed by two stop codons and 23 nucleotides complementary to the 3' end of the coding sequence of the follistatin-3 DNA sequence in FIGS. 1A, 1B, and 1C.

The amplified follistatin-3 DNA fragment and the vector pHE4 are digested with Nde I and Asp 718 and the digested DNAs are then ligated together. Insertion of the follistatin-3 DNA into the restricted pHE4 vector places the follistatin-3 protein coding region downstream from the IPTG-inducible promoter and in-frame with an initiating AUG and the six histidine codons.

The ligation mixture is transformed into competent *E. coli* cells using standard procedures such as those described by Sambrook and colleagues (*Molecular Cloning: a Laboratory Manual*, *2nd Ed*.; Cold Spring Harbor Laboratory Press, Cold Spring Harbor, N.Y. (1989)). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing follistatin-3 protein, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to-1:250. The cells are grown to an optical density at 600 nm ("OD600") of between 0.4 and 0.6. Isopropyl-β-D-thiogalactopyranoside ("IPTG") is then added to a final concentration of 1 mM to induce transcription from the lac repressor sensitive promoter, by inactivating the lacd repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the follistatin-3 is loaded onto a nickel-nitrilo-tri-acetic acid ("Ni-NTA") affinity resin column (QIAGEN, Inc., supra). Proteins with a 6× His tag bind to the Ni-NTA resin with high affinity and can be purified in a simple one-step procedure (for details see: The QIAexpressionist, 1995, QIAGEN, Inc., sipra). Briefly the supernatant is loaded onto the column in 6 M guanidine-HCl; pH 8, the column is first washed with 10 volumes of 6 M guanidine-HCl, pH 8, then washed with 10 volumes of 6 M guanidine-HCl pH 6, and finally the follistatin-3 is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° The following alternative method may be used to purify follistatin-3 expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the follistatin-3 polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded follistatin-3 polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 MM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the follistatin-3 polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40-mM sodium acetate, pH 6.0, 200 mM NaCl. The CM-20 column is then eluted using a 10 column volume linear gradient ranging from 0.2 M NaCl, 50 MM sodium acetate, pH 6.0 to 1.0 M NaCl, 50 mM sodium acetate, pH 6.5. Fractions are collected under constant $A_{280}$ monitoring of the effluent. Fractions containing the follistatin-3 polypeptide (determined, for instance, by 16% SDS-PAGE) are then pooled.

The resultant follistatin-3 polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 μg/ml according to LAL assays.

Example 2

Cloning and Expression of Follistatin-3 protein in a Baculovirus Expression System In this illustrative example, the plasmid shuttle vector pA2 is used to insert the cloned DNA encoding complete protein, including its naturally associated secretory signal (leader) sequence, into a baculovirus to express the mature follistatin-3 protein, using standard methods as described by Summers and colleagues (*A Manual of Methods for Baculovirus Vectors and Insect Cell Culture Procedures*, Texas Agricultural Experimental Station Bulletin No. 1555 (1987)). This expression vector contains the strong polyhedrin promoter of the *Autographa californica* nuclear polyhedrosis virus (AcMNPV) followed by convenient restriction sites such as Bam HI, Xba I and Asp 718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors could be used in place of the vector above, such as pAc373, pVL941 and pAcIMI, as one skilled in the art would readily appreciate, as long as the construct provides appropriately located signals for transcription, translation, secretion and the like, including a signal peptide and an in-frame AUG as required. Such vectors are described, for instance, by Luckow and coworkers (Virology 170:31–39 (1989)).

The cDNA sequence encoding the full length follistatin-3 protein in the deposited clone, including the AUG initiation codon and the naturally associated leader sequence shown in SEQ ID NO:2, is amplified using PCR oligonucleotide primers corresponding to the 5' and 3' sequences of the gene. The 5' primer has the sequence 5' CAT CGC GGA TCC GCC ATC ATG CGT CCC GGG GCG CCA GGG C 3' (SEQ ID NO:14) containing the underlined Bam HI restriction enzyme site, an efficient signal for initiation of translation in eukaryotic cells (Kozak, M., *J. Mol. Biol.* 196:947–950 (1987)), followed by 22 of nucleotides of the sequence of the complete follistatin-3 protein shown in FIG. 1A, beginning with the AUG initiation codon. The 3' primer has the sequence 5' CAT CCG GGT ACC TCA CAC GAA GTT CTC TTC CTC TTC TG 3' (SEQ ID NO:15) containing the underlined Asp 718 restriction site followed by 23 nucleotides complementary to the 3' noncoding sequence in FIG. 1A.

The amplified fragment is isolated from a 1% agarose gel using a commercially available kit ("Geneclean," BIO 101 Inc., La Jolla, Calif.). The fragment then is digested with Bam HI and Asp 718 and again is purified on a 1% agarose gel. This fragment is designated herein F1.

The plasmid is digested with the restriction enzymes Bam HI and Asp 718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue (Statagene Cloning Systems, La Jolla, Calif.) cells are transformed with the ligation mixture and spread on culture plates. Bacteria are identified that contain the plasmid with the human follistatin-3 gene by digesting DNA from individual colonies using Bam HI and Asp 718 and then analyzing the digestion product by gel electrophoresis. The sequence of the cloned fragment is confirmed by DNA sequencing. This plasmid is designated herein pA2Follistatin-3.

Five μg of the piasmid pA2Follistatin-3 is co-transfected with 1.0 μg of a commercially available lincartaed baculovirus DNA ("BaculoGold™ baculovirus DNA". Pharmiagen. San Diego. Calif.), using the lipofeetion method described by Felgner and colleaguew (*Proc. Natl. Acad. Sci. USA* 84:7413–7417 (1987)). One μg of BaculoGold™ virus DNA and 5 μg of the plasmid pA2Follistatin-3 are mixed in a sterile well of a microtiter plate containing 50 μl of serum-free Graces medium (Life Technologies Inc., Gaitbersburg, Md.). Afterwards, 10 μl Lipofecun plus 90 μl Grace's medium are added, mixed and incubated for 15 minutes room temperature. Then the transfeccion mixture is added drop-wise to Sf9 insect cells (ATCC® CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith (supra). An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-Follistatin-3.

To verify the expression of the follistatin-3 gene Sf9 cells are grown in Grace's medium supplemented with 10% heat-inactivated FBS. The cells are infected with the recombinant baculovirus V-Follistatin-3 at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 $\mu$Ci of $^{35}$S-methionine and 5 $\mu$Ci $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the mature form of the follistatin-3 protein, and thus the cleavage point and length of the naturally associated secretory signal peptide.

Follistatin-3 protein has been produced by the above described process in a baculovirus expression system. The resultant follistatin-3 polypeptide was isolated and C-terminal sequencing analysis was used to confirm the prediction that the N-terminal 26 amino acids of the full-length follistatin-3 polypeptide shown in FIGS. 1A, 1B, and 1C (and in SEQ ID NO:2) are cleaved and that the mature form of the follistatin-3 polypeptide begins with methionine-27 as the N-terminal residue according to the numbering scheme of FIGS. 1A, 1B, and 1C (which is identical to methionine-1 according to the numbering scheme of SEQ ID NO:2). Of course, it is important to remember that the observed mature form of a secreted protein may vary according to a number of factors as detailed above.

Example 3

Cloning and Expression of Follistatin-3 in Mammalian Cells

A typical mammalian expression vector contains the promoter clement, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTVLI, HIVI and the early promoter of the cycomegalovirus (CMV). However, cellular elements can also be used (e.g., the human actin promoter). Suitable expression vectors for use in practicing the present invention include, for example, vectors such as pSVL and pMSG (Pharmacia. Uppsala, Sweden), pRSVcar (ATCC® 37152), pSV2dhfr (ATCC® 37146) and pBC12MI (ATCC® 67102). Mammalian host cells that could be used include, human Hela, 293. H9 and Jurkat cells, moUse NIH3T3 and C127 cells, Cos 1, Cos 7 and CV1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS; Murphy, et al., *Biochem J.* 227:277–279 (1991); Bebbington, et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression-vectors pC1 and pC4 contain the strong promoter (LTR) of the Rous Sarcoma Virus (Cullen, et al., *Mol. Cel. Biol.* 5:438–447 (1985)) plus a fragment of the CMV-enhancer (Boshart, et al., *Cell* 41:521–530 (1985)). Multiple cloning sites, e.g., with the restriction enzyme cleavage sites Bam HI, Xba I and Asp 718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pFollistatin-3HA, is made by cloning a portion of the cDNA encoding the mature form of the follistatin-3 protein into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CIV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson and colleagues (*Cell* 37:767 (1984)). The fusion of the HA tag to the target protein allows easy detection and recovery of the recombinant protein with an antibody that recognizes the HA epitope. pcDNAIII contains, in addition, the selectable neomycin marker. A DNA fragment encoding the complete follistatin-3 polypeptide is cloned into the polylinker region of the vector so that recombinant protein expression is directed by the CMV promoter. The plasmid construction strategy is as follows. The follistatin-3 cDNA of the deposited clone is amplified using primers that contain convenient restriction sites, much as described above for construction of vectors for expression of follistatin-3 in *E. coli*. Suitable primers include the following, which are used in this example. The 5' primer, containing the underlined Baam HI site, a Kozak sequence, an AUG start codon, and 22 nucleotides of the 5' coding region of the complete follistatin-3 polypeptide, has the following sequence: 5' CAT CGC <u>GGA TCC</u> GCC ACC ATG CGT CCC GGG GCG CCA GGG C 3' (SEQ ID NO:16). The 3' primer, containing the underlined Asp 718 and 23 of nucleotides complementary to the 3' coding sequence immediately before the-stop codon, has the following sequence: 5' TCA CCG <u>CTCGAG</u> CAC GAA GTT CTC TTC CTC TTC TG 3' (SEQ ID NO:17).

The PCR amplified DNA fragment and the vector, pcDNAI/Amp, are digested with Bam HI and Asp 718 and then ligated. The ligation mixture is transformed into *E. coli* strain SURE (Stratagene Cloning Systems, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the complete follistatin-3 polypeptide For expression of recombinant follistatin-3, COS cells are transfected with an expression vector, as described above, using DEAE-dextran, as described, for instance, by Sambrook and coworkers (*Molecular Cloning: a Laboratory Manual*, Cold Spring Laboratory Press, Cold Spring Harbor, N.Y. (1989)). Cells are incubated under conditions for expression of follistatin-3 by the vector.

Expression of the follistatin-3-HA fusion protein is detected by radiolabeling and immunoprecipitation, using methods described in, for example Harlow and colleagues (*Antibodies: A Laboratory Manual, 2nd Ed.*; Cold Spring Harbor Laboratory Press, Cold Spring Harbor, N.Y. (1988)). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson and colleagues (supra). Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of follistatin-3 polypeptde. Plasmid pC4 is a derivative of the plasmid pSV2-dhfr (ATCC® Accession No. 37146) The plasmid contains the mouse DHFR gene under control of the SV40 early promoter. Chinese hamster ovary- or other cells lacking dihydrofolart activity that are transfected with these placmids can be selected by growing the cells in a selective medium (alpha minus MEM,. Life Technologies) supplemented With the chemotherapuric agent methotrexate. The amplification of the DHFR genes in cells resistant to methotrexate (MTX) has ben well documented (see, e.g., Alt, F. W., et al., *J. Biol. Chem.* 253:1357–1370(1978); Hamlin, J. L. and Ma, C. *Biochem. et Biophys. Acta,* 1097:107–143 (1990); Page, M. J. and Sydenham, M. A. *Biotechnology* 9:64–68 (1991)). Cells grown in iocreasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Mol. Cell. Biol.* 5:438–447 (1985)) plus a fragment isolated from the enhancer of the immediate early gene of human cytomegalovirus (CMV; Boshart, et al., *Cell* 41:521–530 (1985)). Downstream of the promoter are the following single restriction enzyme cleavage sites that allow the integration of the genes: Bam HI, Xba I, and Asp 718. Behind these cloning sites the plasmid contains the 3' intron and polyadenylation site of the rat preproinsulin gene. Other high efficiency promoters can also be used for the expression, e.g., the human B-actin promoter, the SV40 early or late promoters or the long terminal repeats from other retroviruses, e.g., HIV and HTLVI. Clontech's Tet-Off and Tet-On gene expression systems and similar systems can be used to express the follistatin-3 polypeptide in a regulated way in mammalian cells (Gossen, M., and Bujard, H. *Proc. Natl. Acad. Sci. USA* 89:5547–5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes Bam HI and Asp 718 and then dephosphorylated using calf intestinal phosphates by procedures known in the art. The vector is then isolated from a 1% agarose gel. The DNA sequence encoding the complete follistatin-3 polypeptide is amplified using PCR oligonucleotide primers corresponding to the 5' and 3' sequences of the desired portion of the gene. The 5' primer containing the underlined Bam HI site, a Kozak sequence, an AUG start codon, and 22 nucleotides of the 5' coding region of the complete follistatin-3 polypeptide, has the following sequence: 5' CAT CGC <u>GGATCC</u> GCC ACC ATG CGT CCC GGG GCG CCA GGG C 3' (SEQ ID NO:18). The 3' primer, containing the underlined Asp 718 restriction site and 23 of nucleotides complementary to the 3' coding sequence immediately before the stop codon as shown in FIG. 1A (SEQ ID NO:1), has the following sequence: 5' CAT CCG <u>GGT ACC</u> TCA CAC GAA GTT CTC TTC CTC TTC TG 3' (SEQ ID NO:19).

The amplified fragment is digested with the endonucleases Bam HI and Asp 718 and then purified again on a 1% agarose gel. The isolated fragment and the dephosphorylated vector are then ligated with T4 DNA ligase. *E. coli* HB 101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using lipofectin (Felgner, et al., sitpra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Follistatin-3 protein has been produced by the above-described process in a CHO cell expression system. The resultant follistatin-3 polypeptide was isolated and C-terminal sequencing analysis was used to confirm the prediction that the N-terminal 26 amino acids of the full-length follistatin-3 polypeptide shown in FIGS. 1A, 1B, and 1C (and in SEQ ID NO:2) are cleaved and that the mature form of the follistatin-3 polypeptide begins with methionine-27 as the N-terminal residue according to the numbering scheme of FIGS. 1A, 1B, and 1C (which is identical to methionine-1 according to the numbering scheme of SEQ ID NO:2). Of course, it is important to remember that the observed mature form of a secreted protein may vary according to a number of factors as detailed above.

Example 4

Tissue Distribution of Follistatin-3 mRNA Expression

Northern blot analysis was carried out to examine follistatin-3 gene expression in human tissues, using methods described by, among others, Sambrook and colleagues (supra). A cDNA probe containing the entire nucleotide sequence of the follistatin-3 protein (SEQ ID NO:1) was labeled with $^{32}$p using the rediprime™ DNA labeling system (Amersham Life Science), according to manufacturer's instructions. After labeling, the probe was purified using a CHROMA SPIN-100™ column (Clontech Laboratories, Inc.), according to manufacturer's protocol number PT1200–1. The purified labeled probe was then used to examine various human tissues for follistatin-3 mRNA.

Multiple Tissue Northern (MTN) blots containing various human tissues (H) or human immune system tissues (IM) were obtained from Clontech and were examined with the labeled probe using ExpressHyb™ hybridization solution (Clontech) according to manufacturer's protocol number PT1190–1. Following hybridization and washing, the blots were mounted and exposed to film at −70° C. overnight, and films developed according to standard procedures. The follistatin-3-specific probe recognized an mRNA species of approximately 2.6 kb in most tissues examined.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the Sequence Listing submitted herewith, and the Sequence Listing submitted with U.S. Provisional Application Serial No. 60/056,248, filed on Aug. 29, 1997 (to which the present application claims benefit of the filing date under 35 U.S.C. § 119(e)), in both computer and paper forms are hereby incorporated by reference in their entireties.

What is claimed is:

1. An isolated antibody or fragment thereof that specifically binds to a protein selected from the group consisting of:

(a) a protein whose amino acid sequence consists of amino acid residues −26 to +237 of SEQ ID NO:2;

(b) a protein whose amino acid sequence consists of amino acid residues +1 to +237 of SEQ ID NO:2;

(c) a protein whose amino acid sequence consists of a portion of SEQ ID NO:2, wherein said portion is at least 30 contiguous amino acid residues in length; and (d) a protein whose amino acid sequence consists of a portion of SEQ ID NO:2, wherein said portion is at least 50 contiguous amino acid residues in length.

2. The antibody or fragment thereof of claim 1 that specifically binds protein (a).

3. The antibody or fragment thereof of claim 1 that specifically binds protein (b).

4. The antibody or fragment thereof of claim 1 that specifically binds protein (c).

5. The antibody or fragment thereof of claim 1 that specifically binds protein (d).

6. The antibody or fragment thereof of claim 2 that specifically binds protein (d).

7. The antibody or fragment thereof of claim 3 wherein said protein bound by said antibody or fragment thereof is glycosylated.

8. The antibody or fragment thereof of claim 3 wherein said antibody or fragment thereof is human.

9. The antibody or fragment thereof of claim 3 wherein said antibody or fragment thereof is polyclonal.

10. The antibody or fragment thereof of claim 3 which is selected from the group consisting of:

(a) a chimeric antibody or fragment thereof (b) a humanized antibody or fragment thereof;

(c) a single chain antibody; and (d) a Fab fragment.

11. The antibody or fragment thereof of claim 3 which is labeled.

12. The antibody or fragment thereof of claim 11 wherein the label is selected from the group consisting of:

(a) an enzyme;

(b) a fluorescent label;

(c) a luminescent label; and (d) a bioluminescent label.

13. The antibody or fragment thereof of claim 3 wherein said antibody or fragment thereof specifically binds to said protein in a Western blot.

14. The antibody or fragment thereof of claim 3 wherein said antibody or fragment thereof specifically binds to said protein in an ELISA.

15. An isolated cell that produces the antibody or fragment thereof of claim 3.

16. A hybridoma that produces the antibody or fragment thereof of claim 3.

17. A method of detecting follistatin-3 in a biological sample comprising:

(a) contacting the biological sample with the antibody or fragment thereof of claim 3; and (b) detecting follistatin-3 protein in the biological sample.

18. The method of claim 17 wherein the antibody or fragment thereof is polyclonal.

19. An isolated antibody or fragment thereof obtained from an animal that has been immunized with a protein selected from the group consisting of:

(a) a protein whose amino acid sequence consists of amino acid residues −26 to +237 of SEQ ID NO:2;

(b) a protein whose amino acid sequence consists of amino acid residues 1 to +237 of SEQ ID NO:2;

(c) a protein Comprising the amino acid sequence of at least 30 contiguous amino acid residues of SEQ ID NO:2; and (d) a protein comprising the amino acid sequence of at least 50 contiguous amino acid residues of SEQ ID NO:2;

wherein said antibody or fragment thereof specifically binds to said amino acid sequence.

20. The antibody or fragment thereof of claim 19 obtained from an animal immunized with protein (a).

21. The antibody or fragment thereof of claim 19 obtained from an animal immunized with protein (b).

22. The antibody or fragment thereof of claim 19 obtained from an animal immunized with protein (c).

23. The antibody or fragment thereof of claim 19 obtained from an animal immunized with protein (d).

24. The antibody or fragment thereof of claim 19 wherein said antibody or fragment thereof is monoclonal.

25. The antibody or fragment thereof of claim 19 wherein said antibody or fragment thereof is polyclonal.

26. The antibody or fragment thereof of claim 19 which is selected from the group consisting of:

(a) a chimeric antibody or fragment thereof;

(b) a humanized antibody or fragment thereof;

(c) a single chain antibody; and (d) a Fab fragment.

27. An isolated monoclonal antibody or fragment thereof that specifically binds to as protein selected from the group consisting of:

(a) a protein whose amino acid sequence consists of amino acid residues −26 to +237 of SEQ ID NO:2;

(b) a protein whose amino acid sequence consists of amino acid residues +1 to +237 of SEQ ID NO:2;

(c) a protein whose amino acid sequence consists of a portion of SEQ ID NO:2, wherein said portion is at least 30 contiguous is amino acid residues in length; and (d) a protein whose amino acid sequence consists of a portion of SEQ ID NO:2, wherein said portion is at least 50 contiguous is amino acid residues in length.

28. The antibody or fragment thereof of claim 27 that specifically binds protein (a).

29. The antibody or fragment thereof of claim 27 that specifically binds protean (b).

30. The antibody or fragment thereof of claim 27 that specifically binds protein (c).

31. The antibody or fragment thereof of claim 27 that specifically binds protein (d).

32. The antibody or fragment thereof of claim 28 that specifically binds protein (c).

33. The antibody or fragment thereof of claim 29 that wherein said protein bound by said antibody or fragment thereof is glycosylated.

34. The antibody or fragment thereof of claim 29 that wherein said antibody or fragment thereof is human.

35. The antibody or fragment thereof of claim 29 that which is selected from the group consisting of:

(a) a chimeric antibody or fragment thereof;

(b) a humanized antibody or fragment thereof;

(c) a single chain antibody: and (d) a Fab fragment.

36. The antibody or fragment thereof of claim 29 which is labeled.

37. The antibody or fragment thereof of claim 36 wherein the label is selected from the group consisting of:

(a) an enzyme;

(b) a fluorescent label;

(c) a luminescent label; and (d) a bioluminescent label.

38. The antibody or fragment thereof of claim 29 wherein said antibody of fragment thereof specifically binds to said protein in a Western blot.

39. The antibody or fragment thereof of claim 29 wherein said antibody or fragment thereof specifically binds to said protein in an ELISA.

40. An isolated cell that produces the antibody or fragment thereof of claim 29.

41. A hybridoma that produces the antibody or fragment thereof of claim 29.

42. A method of detecting follistatin-3 protein in a biological sample comprising:

(a) contacting the biological sample with the antibody or fragment thereof if claim 29; and (b) detecting follistatin-3 protein in the biological sample.

43. An isolated antibody or fragment thereof that specifically binds to a protein selected from the group consisting of:

(a) a protein whose amino acid sequence consists of the amino acid sequence of the full-length polypeptide encoded by the cDNA contained in ATCC® Deposit Number 209199;

(b) a protein whose amino acid sequence consists of the amino acid sequence of the mature form of the polypeptide encoded by the cDNA contained in ATCC® Deposit Number 209199;

(c) a protein whose amino acid sequence consists of the amino acid sequence of a portion of the polypeptide encoded by the cDNA contained in ATCC® Deposit Number 209199, wherein said portion is at least 30 contiguous amino acid residues in length; and (d) a protein whose amino acid sequence Consists of the amino acid sequence of a portion of the polypeptide encoded by the cDNA contained in ATCC® Deposit Number 209199, wherein said portion is at least 50 contiguous amino acid residues in length.

44. The antibody or fragment thereof of claim 43 that specifically binds protein (a).

45. The antibody or fragment thereof of claim 43 that specifically binds protein (b).

46. The antibody or fragment thereof of claim 43 that specifically binds protein (c).

47. The antibody or fragment thereof of claim 43 that specifically binds protein (d).

48. The antibody or fragment thereof of claim 44 that specifically binds protein (c).

49. The antibody or fragment thereof of claim 45 that wherein said protein bound by said antibody or fragment thereof is glycosylated.

50. The antibody or fragment thereof of claim 45 that wherein said antibody or fragment thereof is human.

51. The antibody or fragment thereof of claim 45 wherein said antibody or fragment thereof is polyclonal.

52. The antibody or fragment thereof of claim 45 which is selected from the group consisting of:

(a) a chimeric antibody or fragment thereof;

(b) a humanized antibody or fragment thereof;

(c) a single chain antibody; and (d) a Fab fragment.

53. The antibody or fragment thereof of claim 45 which is labeled.

54. The antibody or fragment thereof of claim 45 wherein the label is selected from the group consisting of:

(a) an enzyme;

(b) a fluorescent label;

(c) a luminescent label; and (d) a bioluminescent label.

55. The antibody or fragment thereof of claim 45 wherein said antibody or fragment thereof specifically binds to said protein in a Western blot.

56. The antibody or fragment thereof of claim 45 wherein said antibody or fragment thereof specifically binds to said protein in an ELISA.

57. An isolated cell that produces the antibody or fragment thereof of claim 45.

58. A hybridoma that produces the antibody or fragment thereof of claim 45.

59. A method of detecting follistatin-3 protein in a biological sample comprising:

(a) contacting the biological sample with the antibody or fragment thereof of claim 45; and (b) detecting follistatin-3 protein in the biological sample.

60. The method of claim 59 wherein the antibody or fragment thereof is polyclonal.

61. An isolated antibody or fragment thereof obtained from an animal that has been immunized with a protein selected from the group consisting of:

(a) a protein comprising the amino acid sequence of the full-length polypeptide encoded by the cDNA contained in ATCC® Deposit Number 209199;

(b) a protein comprising the amino acid sequence of the mature form of the polypeptide encoded by the cDNA contained in ATCC® Deposit Number 209199;

(c) a protein comprising the amino acid sequence of at least 30 contiguous amino acid residues of the polypeptide encoded by the cDNA contained in ATCC® Deposit Number 209199; and (d) a protein comprising the amino acid sequence of at least 50 contiguous amino acid residues the polypeptide encoded by the cDNA contained in ATCC® Deposit Number 209199;

wherein said antibody or fragment thereof specifically binds to said amino acid sequence.

62. The antibody or fragment thereof of claim 61 obtained from an animal immunized with protein (a).

63. The antibody or fragment thereof of claim 61 obtained from an animal immunized with protein (b).

64. The antibody or fragment thereof of claim 61 obtained from an animal immunized with protein (c).

65. The antibody or fragment thereof of claim 61 obtained from an animal immunized with protein (d).

66. The antibody or fragment thereof of claim 61 wherein the antibody or fragment thereof is monoclonal.

67. The antibody or fragment thereof of claim 61 wherein the antibody or fragment thereof is polyclonal.

68. The antibody or fragment thereof of claim 61 which is selected from the group consisting of:

(a) a chimeric antibody or fragment thereof;

(b) a humanized antibody or fragment thereof;

(c) a single chain antibody; and (d) a Fab fragment.

69. An isolated monoclonal antibody or fragment thereof that specifically binds to a protein selected from the group consisting of:

(a) a protein whose amino acid sequence consists of the amino acid sequence of the full-length polypeptide encoded by the cDNA contained in ATCC® Deposit Number 209199;

(b) a protein whose amino acid sequence consists of the amino acid sequence of the mature form of the polypeptide encoded by the cDNA contained in ATCC® Deposit Number 209199;

(c) a protein whose amino acid sequence consists of the amino acid sequence of a portion of the polypeptide encoded by the cDNA contained in ATCC® Deposit Number 209199, wherein said portion is at least 30 contiguous amino acid residues in length; and (d) a protein whose amino acid sequence consists of the amino acid sequence of a portion of the polypeptide encoded by the cDNA contained in ATCC® Deposit Number 209199, wherein said portion is at least 50 contiguous amino acid residues in length.

70. The antibody or fragment thereof of claim 69 that specifically binds protein (a).

71. The antibody or fragment thereof of claim 69 that specifically binds protein (b).

72. The antibody or fragment thereof of claim 69 that specifically binds protein (c).

73. The antibody or fragment thereof of claim 69 that specifically binds protein (d).

74. The antibody or fragment thereof of claim 70 that specifically binds protein (c).

75. The antibody or fragment thereof of claim 71 that wherein said protein bound by said antibody or fragment thereof is glycosylated.

76. The antibody or fragment thereof of claim 71 that wherein said antibody or fragment thereof is human.

77. The antibody or fragment thereof of claim 71 that which is selected from the group consisting of:

(a) a chimeric antibody or fragment thereof;

(b) a humanized antibody or fragment thereof;

(c) a single chain antibody; and (d) a Fab fragment.

78. The antibody or fragment thereof of claim 71 which is labeled.

79. The antibody or fragment thereof of claim 78 wherein the label is selected from the group consisting of:

(a) an enzyme;

(b) a fluorescent label;

(c) a luminescent label; and (d) a bioluminescent label.

80. The antibody or fragment thereof of claim 71 wherein said antibody or fragment thereof specifically binds to said protein in a Western blot.

81. The antibody or fragment thereof of claim 71 wherein said antibody or fragment thereof specifically binds to said protein in an ELISA.

82. An isolated cell that produces the antibody or fragment thereof of claim 71.

83. A hybridoma that produces the antibody or fragment thereof of claim 71.

84. A method of detecting follistatin-3 protein in a biological sample comprising:

(a) contacting the biological sample with the antibody or fragment thereof of claim 71; and (b) detecting the follistatin-3 protein in the biological sample.

85. An isolated antibody or fragment thereof that specifically binds follistatin-3 protein purified from a cell culture wherein said follistatin-3 protein is encoded by a polynucleotide encoding amino acid −26 to +237 of SEQ ID NO:2.

86. The antibody or fragment thereof of claim 85 wherein said antibody or fragment thereof is monoclonal.

87. The antibody or fragment thereof of claim 85 wherein said antibody or fragment thereof is polyclonal.

88. The antibody or fragment thereof of claim 85 wherein said antibody or fragment thereof is human.

89. The antibody or fragment thereof of claim 85 which is selected from the group consisting of:

(a) chimeric antibody or fragment thereof;

(b) a humanized antibody or fragment thereof;

(c) a single chain antibody; and (d) a Fab fragment.

90. The antibody or fragment thereof of claim 85 wherein said antibody or fragment thereof specifically binds to said protein in a Western blot.

91. The antibody or fragment thereof of claim 85 wherein said antibody or fragment thereof specifically binds to said protein in an ELISA.

* * * * *

UNITED STATES PATENT AND TRADEMARK OFFICE

CERTIFICATE OF CORRECTION

PATENT NO. : 6,921,644 B2
DATED : July 26, 2005
INVENTOR(S) : Duan et al.

It is certified that error appears in the above-identified patent and that said Letters Patent is hereby corrected as shown below:

Title page,
Item [54], Title, should read -- ANTIBODIES TO FOLLISTATIN-3 --;

Column 83,
Line 56, delete "a protein Comprising" and insert -- a protein comprising --;

Column 84,
Line 26, delete "30 contiguous is amino acid residues" and insert -- 30 contiguous amino acid residues --;
Line 30, delete "50 contiguous is amino acid residues" and insert -- 50 contiguous amino acid residues --;
Lines 41 and 45, delete "fragment thereof of claim 29 that wherein" and insert -- fragment thereof of claim 29 that wherein --;

Column 85,
Line 7, delete "fragment thereof of claim 29; and" and insert -- fragment thereof of claim 29; and --;
Line 26, delete "a protein whose amino acid sequence Consists of the" and insert -- a protein whose amino acid sequence consists of the --;
Lines 41 and 44, delete "fragment thereof of claim 45 that wherein" and insert -- fragment thereof of claim 45 wherein --;

UNITED STATES PATENT AND TRADEMARK OFFICE

CERTIFICATE OF CORRECTION

PATENT NO. : 6,921,644 B2
DATED : July 26, 2005
INVENTOR(S) : Duan et al.

It is certified that error appears in the above-identified patent and that said Letters Patent is hereby corrected as shown below:

Column 87,
Lines 15 and 18, delete "fragment thereof of claim 71 that wherein" and insert -- fragment thereof of claim 71 wherein --;
Line 20, delete "fragment thereof of claim 71 that which" and insert -- fragment thereof of claim 71 which --.

Signed and Sealed this

Twenty-seventh Day of December, 2005

JON W. DUDAS
*Director of the United States Patent and Trademark Office*

SEQUENCE LISTING

```
<160> NUMBER OF SEQ ID NOS: 19

<210> SEQ ID NO 1
<211> LENGTH: 2495
<212> TYPE: DNA
<213> ORGANISM: Homo sapiens
<220> FEATURE:
<221> NAME/KEY: CDS
<222> LOCATION: (19)..(807)
<221> NAME/KEY: mat_peptide
<222> LOCATION: (97)..(807)
<221> NAME/KEY: sig_peptide
<222> LOCATION: (19)..(96)
<221> NAME/KEY: misc_feature
<222> LOCATION: (2429)
<223> OTHER INFORMATION: n equals a, t, g, or c

<400> SEQUENCE: 1

gccgtctctg cgttcgcc atg cgt ccc ggg gcg cca ggg cca ctc tgg cct       51
                    Met Arg Pro Gly Ala Pro Gly Pro Leu Trp Pro
                        -25                 -20

ctg ccc tgg ggg gcc ctg gct tgg gcc gtg ggc ttc gtg agc tcc atg       99
Leu Pro Trp Gly Ala Leu Ala Trp Ala Val Gly Phe Val Ser Ser Met
-15                 -10                 -5                  -1   1

ggc tcg ggg aac ccc gcg ccc ggt ggt gtt tgc tgg ctc cag cag ggc      147
Gly Ser Gly Asn Pro Ala Pro Gly Gly Val Cys Trp Leu Gln Gln Gly
            5                   10                  15

cag gag gcc acc tgc agc ctg gtg ctc cag act gat gtc acc cgg gcc      195
Gln Glu Ala Thr Cys Ser Leu Val Leu Gln Thr Asp Val Thr Arg Ala
        20                  25                  30

gag tgc tgt gcc tcc ggc aac att gac acc gcc tgg tcc aac ctc acc      243
Glu Cys Cys Ala Ser Gly Asn Ile Asp Thr Ala Trp Ser Asn Leu Thr
    35                  40                  45
```

-continued

```
cac ccg ggg aac aag atc aac ctc ctc ggc ttc ttg ggc ctt gtc cac      291
His Pro Gly Asn Lys Ile Asn Leu Leu Gly Phe Leu Gly Leu Val His
 50                  55                  60                  65

tgc ctt ccc tgc aaa gat tcg tgc gac ggc gtg gag tgc ggc ccg ggc      339
Cys Leu Pro Cys Lys Asp Ser Cys Asp Gly Val Glu Cys Gly Pro Gly
                70                  75                  80

aag gcg tgc cgc atg ctg ggg ggc cgc ccg cgc tgc gag tgc gcg ccc      387
Lys Ala Cys Arg Met Leu Gly Gly Arg Pro Arg Cys Glu Cys Ala Pro
            85                  90                  95

gac tgc tcg ggg ctc ccg gcg cgg ttg cag gtc tgc ggc tca gac ggc      435
Asp Cys Ser Gly Leu Pro Ala Arg Leu Gln Val Cys Gly Ser Asp Gly
        100                 105                 110

gcc acc tac cgc gac gag tgc gag ctg cgc gcc gcg cgc tgc cgc ggc      483
Ala Thr Tyr Arg Asp Glu Cys Glu Leu Arg Ala Ala Arg Cys Arg Gly
    115                 120                 125

cac ccg gac ctg agc gtc atg tac cgg ggc cgc tgc cgc aag tcc tgt      531
His Pro Asp Leu Ser Val Met Tyr Arg Gly Arg Cys Arg Lys Ser Cys
130                 135                 140                 145

gag cac gtg gtg tgc ccg cgg cca cag tcg tgc gtc gtg gac cag acg      579
Glu His Val Val Cys Pro Arg Pro Gln Ser Cys Val Val Asp Gln Thr
                150                 155                 160

ggc agc gcc cac tgc gtg gtg tgt cga gcg gcg ccc tgc cct gtg ccc      627
Gly Ser Ala His Cys Val Val Cys Arg Ala Ala Pro Cys Pro Val Pro
            165                 170                 175

tcc agc ccc ggc cag gag ctt tgc ggc aac aac aac gtc acc tac atc      675
Ser Ser Pro Gly Gln Glu Leu Cys Gly Asn Asn Asn Val Thr Tyr Ile
        180                 185                 190

tcc tcg tgc cac atg cgc cag gcc acc tgc ttc ctg ggc cgc tcc atc      723
Ser Ser Cys His Met Arg Gln Ala Thr Cys Phe Leu Gly Arg Ser Ile
    195                 200                 205

ggc gtg cgc cac gcg ggc agc tgc gca ggc acc cct gag gag ccg cca      771
Gly Val Arg His Ala Gly Ser Cys Ala Gly Thr Pro Glu Glu Pro Pro
210                 215                 220                 225

ggt ggt gag tct gca gaa gag gaa gag aac ttc gtg tgagcctgca           817
Gly Gly Glu Ser Ala Glu Glu Glu Glu Asn Phe Val
                230                 235

ggacaggcct gggcctggtg cccgaggccc cccatcatcc cctgttattt attgccacag    877

cagagtctaa tttatatgcc acggacactc cttagagccc ggattcggac cacttgggga    937

tcccagaacc tccctgacga tatcctggaa ggactgagga agggaggcct gggggccggc    997

tggtgggtgg gatagacctg cgttccggac actgagcgcc tgatttaggg cccttctcta   1057

ggatgcccca gcccctaccc taagacctat tgccggggag gattccacac ttccgctcct   1117

ttggggataa acctattaat tattgctact atcaagaggg ctgggcattc tctgctggta   1177

attcctgaag aggcatgact gcttttctca gccccaagcc tctagtctgg gtgtgtacgg   1237

agggtctagc ctgggtgtgt acggagggtc tagcctgggt gagtacggag ggtctagcct   1297

gggtgagtac ggaggatcta gcctgggtga gtacggagag tctagcctgg gtgtgtatgg   1357

aggatctagc ctgggtgagt atggagggtc tagcctgggt gagtatggag ggtctagcct   1417

gggtgtgtat ggagggtcta gcctgggtga gtatggaggg tctagcctgg gtgtgtatgg   1477

agggtctagc ctgggtgagt atggagggtc tagcctgggt gtgtacggag ggtctagtct   1537

gagtgcgtgt ggggacctca gaacactgtg accttagccc agcaagccag gcccttcatg   1597

aaggccaaga aggctgccac cattccctgc cagcccaaga actccagctt ccccactgcc   1657

tctgtgtgcc cctttgcgtc ctgtgaaggc cattgagaaa tgcccagtgt gccccctggg   1717

aaagggcacg gcctgtgctc ctgacacggg ctgtgcttgg ccacagaacc acccagcgtc   1777
```

-continued

```
tcccctgctg ctgtccacgt cagttcatga ggcaacgtcg cgtggtctca gacgtggagc   1837

agccagcggc agctcagagc agggcactgt gtccggcgga gccaagtcca ctctggggga   1897

gctctggcgg ggaccacggg ccactgctca cccactggcc ccgagggggg tgtagacgcc   1957

aagactcacg catgtgtgac atccggagtc ctggagccgg gtgtcccagt ggcaccacta   2017

ggtgcctgct gcctccacag tggggttcac acccagggct ccttggtccc ccacaacctg   2077

ccccggccag gcctgcagac ccagactcca gccagacctg cctcacccac caatgcagcc   2137

ggggctggcg acaccagcca ggtgctggtc ttgggccagt tctcccacga cggctcaccc   2197

tcccctccat ctgcgttgat gctcagaatc gcctacctgt gcctgcgtgt aaaccacagc   2257

ctcagaccag ctatggggag aggacaacac ggaggatatc cagcttcccc ggtctggggt   2317

gaggagtgtg gggagcttgg gcatcctcct ccagcctcct ccagccccca ggcagtgcct   2377

tacctgtggt gcccagaaaa gtgcccctag gttggtgggt ctacaggagc cncagccagg   2437

cagcccaccc caccctgggg ccctgcctca ccaaggaaat aaagactcaa agaagcct     2495
```

<210> SEQ ID NO 2
<211> LENGTH: 263
<212> TYPE: PRT
<213> ORGANISM: Homo sapiens

<400> SEQUENCE: 2

```
Met Arg Pro Gly Ala Pro Gly Pro Leu Trp Pro Leu Pro Trp Gly Ala
    -25                 -20                 -15

Leu Ala Trp Ala Val Gly Phe Val Ser Ser Met Gly Ser Gly Asn Pro
-10                 -5              -1   1               5

Ala Pro Gly Gly Val Cys Trp Leu Gln Gln Gly Gln Glu Ala Thr Cys
             10                  15                  20

Ser Leu Val Leu Gln Thr Asp Val Thr Arg Ala Glu Cys Cys Ala Ser
         25                  30                  35

Gly Asn Ile Asp Thr Ala Trp Ser Asn Leu Thr His Pro Gly Asn Lys
     40                  45                  50

Ile Asn Leu Leu Gly Phe Leu Gly Leu Val His Cys Leu Pro Cys Lys
 55                  60                  65                  70

Asp Ser Cys Asp Gly Val Glu Cys Gly Pro Gly Lys Ala Cys Arg Met
                 75                  80                  85

Leu Gly Gly Arg Pro Arg Cys Glu Cys Ala Pro Asp Cys Ser Gly Leu
             90                  95                 100

Pro Ala Arg Leu Gln Val Cys Gly Ser Asp Gly Ala Thr Tyr Arg Asp
        105                 110                 115

Glu Cys Glu Leu Arg Ala Ala Arg Cys Arg Gly His Pro Asp Leu Ser
    120                 125                 130

Val Met Tyr Arg Gly Arg Cys Arg Lys Ser Cys Glu His Val Val Cys
135                 140                 145                 150

Pro Arg Pro Gln Ser Cys Val Val Asp Gln Thr Gly Ser Ala His Cys
                155                 160                 165

Val Val Cys Arg Ala Ala Pro Cys Pro Val Pro Ser Ser Pro Gly Gln
            170                 175                 180

Glu Leu Cys Gly Asn Asn Asn Val Thr Tyr Ile Ser Ser Cys His Met
        185                 190                 195

Arg Gln Ala Thr Cys Phe Leu Gly Arg Ser Ile Gly Val Arg His Ala
    200                 205                 210
```

-continued

```
Gly Ser Cys Ala Gly Thr Pro Glu Glu Pro Pro Gly Gly Glu Ser Ala
215                 220                 225                 230

Glu Glu Glu Glu Asn Phe Val
                235


<210> SEQ ID NO 3
<211> LENGTH: 317
<212> TYPE: PRT
<213> ORGANISM: Homo sapiens

<400> SEQUENCE: 3

Met Val Arg Ala Arg His Gln Pro Gly Gly Leu Cys Leu Leu Leu Leu
  1               5                  10                  15

Leu Leu Cys Gln Phe Met Glu Asp Arg Ser Ala Gln Ala Gly Asn Cys
             20                  25                  30

Trp Leu Arg Gln Ala Lys Asn Gly Arg Cys Gln Val Leu Tyr Lys Thr
         35                  40                  45

Glu Leu Ser Lys Glu Glu Cys Cys Ser Thr Gly Arg Leu Ser Thr Ser
     50                  55                  60

Trp Thr Glu Glu Asp Val Asn Asp Asn Thr Leu Phe Lys Trp Met Ile
 65                  70                  75                  80

Phe Asn Gly Gly Ala Pro Asn Cys Ile Pro Cys Lys Glu Thr Cys Glu
                 85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn
305                 310                 315


<210> SEQ ID NO 4
<211> LENGTH: 508
<212> TYPE: DNA
<213> ORGANISM: Homo sapiens
```

<220> FEATURE:
<221> NAME/KEY: misc_feature
<222> LOCATION: (377)
<223> OTHER INFORMATION: n equals a, t, g, or c
<221> NAME/KEY: misc_feature
<222> LOCATION: (379)
<223> OTHER INFORMATION: n equals a, t, g, or c
<221> NAME/KEY: misc_feature
<222> LOCATION: (428)
<223> OTHER INFORMATION: n equals a, t, g, or c
<221> NAME/KEY: misc_feature
<222> LOCATION: (439)
<223> OTHER INFORMATION: n equals a, t, g, or c
<221> NAME/KEY: misc_feature
<222> LOCATION: (444)
<223> OTHER INFORMATION: n equals a, t, g, or c
<221> NAME/KEY: misc_feature
<222> LOCATION: (452)
<223> OTHER INFORMATION: n equals a, t, g, or c
<221> NAME/KEY: misc_feature
<222> LOCATION: (461)
<223> OTHER INFORMATION: n equals a, t, g, or c
<221> NAME/KEY: misc_feature
<222> LOCATION: (466)
<223> OTHER INFORMATION: n equals a, t, g, or c
<221> NAME/KEY: misc_feature
<222> LOCATION: (468)
<223> OTHER INFORMATION: n equals a, t, g, or c
<221> NAME/KEY: misc_feature
<222> LOCATION: (470)
<223> OTHER INFORMATION: n equals a, t, g, or c
<221> NAME/KEY: misc_feature
<222> LOCATION: (475)
<223> OTHER INFORMATION: n equals a, t, g, or c
<221> NAME/KEY: misc_feature
<222> LOCATION: (485)
<223> OTHER INFORMATION: n equals a, t, g, or c
<221> NAME/KEY: misc_feature
<222> LOCATION: (501)
<223> OTHER INFORMATION: n equals a, t, g, or c
<221> NAME/KEY: misc_feature
<222> LOCATION: (505)
<223> OTHER INFORMATION: n equals a, t, g, or c
<221> NAME/KEY: misc_feature
<222> LOCATION: (399)
<223> OTHER INFORMATION: n equals a, t, g or c

<400> SEQUENCE: 4
aattcggcac gagtttctca gccccaagcc tctagtctgg gtgtgtacgg agggtctagc 60
ctgggtgtgt acggagggtc tagcctgggt gagtacggag ggtctagcct gggtgagtac 120
ggagggtcta gcctgggtga gtacggagag tctagcctgg gtgtgtatgg aggatctagc 180
ctgggtgagt atggagggtc tagcctgggt gagtatggag ggtctagcct gggtgtgtat 240
ggagggtcta gcctgggtga gtatggaggg tctagcctgg gtgtgtatgg agggtctagc 300
ctgggtgagt atggagggtc tagccttggt gtttacggag ggtctagtct gagttcgttt 360
tggggacctc agaacantnt taacctttag cccagnaanc caggccctta atgaaggcca 420
gaaggttnca ccattcctnc cctnccaaga antcaatttc nnaatncntn ttgtnccctt 480
ttggnccttt aagccattta naatncca 508

<210> SEQ ID NO 5
<211> LENGTH: 466
<212> TYPE: DNA
<213> ORGANISM: Homo sapiens
<220> FEATURE:
<221> NAME/KEY: misc_feature
<222> LOCATION: (415)
<223> OTHER INFORMATION: n equals a, t, g, or c
<221> NAME/KEY: misc_feature
<222> LOCATION: (422)
<223> OTHER INFORMATION: n equals a, t, g, or c -continued

```
<221> NAME/KEY: misc_feature
<222> LOCATION: (437)
<223> OTHER INFORMATION: n equals a, t, g, or c
<221> NAME/KEY: misc_feature
<222> LOCATION: (449)
<223> OTHER INFORMATION: n equals a, t, g, or c

<400> SEQUENCE: 5

ggcgacggcg tggagtgcgg cccgggcaag gcgtgccgca tgctgggggg ccgcccgcgc     60

tgcgagtgcg cgcccgactg ctcggggctc ccggcgcggt tgcaggtctg cggctcagac    120

ggcgccacct accgcgacga gtgcgagctg cgcgccgcgc gctgccgcgg ccacccggac    180

ctgagcgtca tgtaccgggg ccgctgccgc aagtcctgtg agcacgtggt gtgcccgcgg    240

ccacagtcgt gcgtcgtgga ccagacgggc agcgcccact gcgtggtgtg tcgaagcggc    300

gccctgccct gtgccctcca gccccggcca ggagctttgc ggccaacaac aaagttacct    360

aaatttcttc gtgccaaatg cgccaaggcc aactgcttcc tgggccggtt ccatnnggcg    420

tncgccaagc gggcaanttt cgcaagcanc cctgaaggag ccgcca                   466


<210> SEQ ID NO 6
<211> LENGTH: 337
<212> TYPE: DNA
<213> ORGANISM: Homo sapiens
<220> FEATURE:
<221> NAME/KEY: misc_feature
<222> LOCATION: (33)
<223> OTHER INFORMATION: n equals a, t, g, or c
<221> NAME/KEY: misc_feature
<222> LOCATION: (60)
<223> OTHER INFORMATION: n equals a, t, g, or c
<221> NAME/KEY: misc_feature
<222> LOCATION: (92)..(93)
<223> OTHER INFORMATION: n equals a, t, g, or c
<221> NAME/KEY: misc_feature
<222> LOCATION: (141)
<223> OTHER INFORMATION: n equals a, t, g, or c
<221> NAME/KEY: misc_feature
<222> LOCATION: (264)
<223> OTHER INFORMATION: n equals a, t, g, or c
<221> NAME/KEY: misc_feature
<222> LOCATION: (129)
<223> OTHER INFORMATION: n equals a, t, g or c

<400> SEQUENCE: 6

cttgagtgcg tgtggggacc tcagaacact gtnaccttag cccagcaagc caggcccttn     60

atgaaggcca agaaggctgc caccattccc tnncagccca agaactccag cttccccact    120

gcctctttnt gccccttgc ntcctgtgaa ggccattgag aaatgcccag tgtgccccct     180

gggaaagggc acggcctgtg ctcctgacac gggctgtgct tggccacaga accacccagc    240

gtctcccctg ctgctgtcca cgtnagttca tgaggcaacg tcgcgtggtc ttcagacgtg    300

ggagcagcca gcggcagctc aggaggcagg gcactgt                             337


<210> SEQ ID NO 7
<211> LENGTH: 298
<212> TYPE: DNA
<213> ORGANISM: Homo sapiens
<220> FEATURE:
<221> NAME/KEY: misc_feature
<222> LOCATION: (5)
<223> OTHER INFORMATION: n equals a, t, g, or c
<221> NAME/KEY: misc_feature
<222> LOCATION: (11)
<223> OTHER INFORMATION: n equals a, t, g, or c
<221> NAME/KEY: misc_feature
<222> LOCATION: (68)
<223> OTHER INFORMATION: n equals a, t, g, or c
```

```
<221> NAME/KEY: misc_feature
<222> LOCATION: (70)
<223> OTHER INFORMATION: n equals a, t, g, or c
<221> NAME/KEY: misc_feature
<222> LOCATION: (84)
<223> OTHER INFORMATION: n equals a, t, g, or c
<221> NAME/KEY: misc_feature
<222> LOCATION: (111)
<223> OTHER INFORMATION: n equals a, t, g, or c
<221> NAME/KEY: misc_feature
<222> LOCATION: (186)
<223> OTHER INFORMATION: n equals a, t, g, or c
<221> NAME/KEY: misc_feature
<222> LOCATION: (243)
<223> OTHER INFORMATION: n equals a, t, g, or c
<221> NAME/KEY: misc_feature
<222> LOCATION: (266)
<223> OTHER INFORMATION: n equals a, t, g, or c
<221> NAME/KEY: misc_feature
<222> LOCATION: (272)
<223> OTHER INFORMATION: n equals a, t, g, or c
<221> NAME/KEY: misc_feature
<222> LOCATION: (280)
<223> OTHER INFORMATION: n equals a, t, g, or c
<221> NAME/KEY: misc_feature
<222> LOCATION: (288)
<223> OTHER INFORMATION: n equals a, t, g, or c

<400> SEQUENCE: 7

ggcanagccg nctggtgggt gggatagacc tgctttccgg acactgagcg cctgatttag     60

ggcccttntn taggaatgcc ccanccccta ccctaagacc tattgccggg naggattcca    120

cacttccgct cctttgggga taaacctatt aattattgct actatcaaga gggctggggc    180

attctntgct ggtaaattcc tgaagaggca tgactgcttt tttaagcccc aagcctctag    240

ttntgggtgt tttacggagg ggtctnagcc tngggttgtn gtacgggngg ggttctta      298


<210> SEQ ID NO 8
<211> LENGTH: 186
<212> TYPE: DNA
<213> ORGANISM: Homo sapiens
<220> FEATURE:
<221> NAME/KEY: misc_feature
<222> LOCATION: (34)
<223> OTHER INFORMATION: n equals a, t, g, or c
<221> NAME/KEY: misc_feature
<222> LOCATION: (128)
<223> OTHER INFORMATION: n equals a, t, g, or c
<221> NAME/KEY: misc_feature
<222> LOCATION: (155)..(156)
<223> OTHER INFORMATION: n equals a, t, g, or c
<221> NAME/KEY: misc_feature
<222> LOCATION: (180)
<223> OTHER INFORMATION: n equals a, t, g, or c

<400> SEQUENCE: 8

ccggcggagc aaagtccact ctgggggagc tctngcgggg accacgggcc actgctcacc     60

cactggcccc gaggggggtg tagacgccaa gactcacgca tgtttgacat ccggagtcct    120

ggagccgngt gtcccagtgg caccactagg tgctnnctgc ctccacagtg ggttcacan     180

ccaggg                                                               186


<210> SEQ ID NO 9
<211> LENGTH: 308
<212> TYPE: DNA
<213> ORGANISM: Homo sapiens
<220> FEATURE:
<221> NAME/KEY: misc_feature
<222> LOCATION: (3)
<223> OTHER INFORMATION: n equals a, t, g, or c
```

-continued

<221> NAME/KEY: misc_feature
<222> LOCATION: (19)
<223> OTHER INFORMATION: n equals a, t, g, or c
<221> NAME/KEY: misc_feature
<222> LOCATION: (24)
<223> OTHER INFORMATION: n equals a, t, g, or c
<221> NAME/KEY: misc_feature
<222> LOCATION: (29)
<223> OTHER INFORMATION: n equals a, t, g, or c
<221> NAME/KEY: misc_feature
<222> LOCATION: (34)
<223> OTHER INFORMATION: n equals a, t, g, or c
<221> NAME/KEY: misc_feature
<222> LOCATION: (38)
<223> OTHER INFORMATION: n equals a, t, g, or c
<221> NAME/KEY: misc_feature
<222> LOCATION: (40)
<223> OTHER INFORMATION: n equals a, t, g, or c
<221> NAME/KEY: misc_feature
<222> LOCATION: (50)
<223> OTHER INFORMATION: n equals a, t, g, or c
<221> NAME/KEY: misc_feature
<222> LOCATION: (83)
<223> OTHER INFORMATION: n equals a, t, g, or c
<221> NAME/KEY: misc_feature
<222> LOCATION: (107)
<223> OTHER INFORMATION: n equals a, t, g, or c
<221> NAME/KEY: misc_feature
<222> LOCATION: (205)
<223> OTHER INFORMATION: n equals a, t, g, or c
<221> NAME/KEY: misc_feature
<222> LOCATION: (220)
<223> OTHER INFORMATION: n equals a, t, g, or c
<221> NAME/KEY: misc_feature
<222> LOCATION: (237)
<223> OTHER INFORMATION: n equals a, t, g, or c
<221> NAME/KEY: misc_feature
<222> LOCATION: (272)
<223> OTHER INFORMATION: n equals a, t, g, or c
<221> NAME/KEY: misc_feature
<222> LOCATION: (242)
<223> OTHER INFORMATION: n equals a, t, g, or c
<221> NAME/KEY: misc_feature
<222> LOCATION: (297)
<223> OTHER INFORMATION: n equals a, t, g, or c
<221> NAME/KEY: misc_feature
<222> LOCATION: (308)
<223> OTHER INFORMATION: n equals a, t, g, or c

<400> SEQUENCE: 9

```
ggnagaggtg acaccagcna ggtnctgtnt tggnccantn ctcccacgan ggctcaccct     60

cccctccatc tgctttaatg ctncgaatcg cctacctgtg ccctgcntgt aaaccacagc    120

tttcaaacca gctatgggga gaggacaaca cggaggatat tccagcttcc ccggtctggg    180

gtgaaggagt gtggggagct tgggncatcc tcctccagtn tcctccagcc cccaggnagt    240

gnctttaanc tgtgggttgc ccagaaaagt gncccttagg tttgttgggt tttaaangga    300

gctttaan                                                             308
```

<210> SEQ ID NO 10
<211> LENGTH: 407
<212> TYPE: DNA
<213> ORGANISM: Homo sapiens
<220> FEATURE:
<221> NAME/KEY: misc_feature
<222> LOCATION: (290)
<223> OTHER INFORMATION: n equals a, t, g, or c
<221> NAME/KEY: misc_feature
<222> LOCATION: (298)
<223> OTHER INFORMATION: n equals a, t, g, or c
<221> NAME/KEY: misc_feature
<222> LOCATION: (324)
<223> OTHER INFORMATION: n equals a, t, g, or c
<221> NAME/KEY: misc_feature
<222> LOCATION: (326)
<223> OTHER INFORMATION: n equals a, t, g, or c
<221> NAME/KEY: misc_feature
<222> LOCATION: (386)
<223> OTHER INFORMATION: n equals a, t, g, or c
<221> NAME/KEY: misc_feature
<222> LOCATION: (402)
<223> OTHER INFORMATION: n equals a, t, g, or c
<221> NAME/KEY: misc_feature
<222> LOCATION: (407)
<223> OTHER INFORMATION: n equals a, t, g, or c

<400> SEQUENCE: 10
ggcacgagcc tgggtgtgta cggagggtct agtctgagtg cgtgtggggc ctcagaacac 60
tgtgacctta gcccagcaag ccaggccttc atgaaggcaa gaaggtgcca ccattccctg 120
ccagcccaag actccagttc cccactgcct ctgtgtgccc tttgcgtcct gtgaagccat 180
tgagaaatgc ccatgtgccc ctgggaaagg gcacggctgt gtcctgacag ggtgtgtttg 240
cacagaccac caggtttcct gtgtgtcagt attatgagga acgtcggtgn ttagagtnga 300
gcagcaggga gttagagcag gatntntccg ggcaagtcc attttggggt tttgcggaca 360
gggcatgtta ccattgcccg aggggntaga gcagttagat tntgaan 407

<210> SEQ ID NO 11
<211> LENGTH: 139
<212> TYPE: DNA
<213> ORGANISM: Homo sapiens
<220> FEATURE:
<221> NAME/KEY: misc_feature
<222> LOCATION: (2)
<223> OTHER INFORMATION: n equals a, t, g, or c
<221> NAME/KEY: misc_feature
<222> LOCATION: (9)
<223> OTHER INFORMATION: n equals a, t, g, or c
<221> NAME/KEY: misc_feature
<222> LOCATION: (11)
<223> OTHER INFORMATION: n equals a, t, g, or c
<221> NAME/KEY: misc_feature
<222> LOCATION: (45)
<223> OTHER INFORMATION: n equals a, t, g, or c
<221> NAME/KEY: misc_feature
<222> LOCATION: (70)
<223> OTHER INFORMATION: n equals a, t, g, or c
<221> NAME/KEY: misc_feature
<222> LOCATION: (105)
<223> OTHER INFORMATION: n equals a, t, g, or c
<221> NAME/KEY: misc_feature
<222> LOCATION: (131)
<223> OTHER INFORMATION: n equals a, t, g, or c
<221> NAME/KEY: misc_feature
<222> LOCATION: (137)
<223> OTHER INFORMATION: n equals a, t, g, or c

<400> SEQUENCE: 11
anccagggnt ncttggtccc ccacaacctt ccccggccag gcctncagac ccagacttca 60
gccagacctn ccttaaccac caatgcagcc ggggcttgcg acaanagcag gtgctggtct 120
tggggcagtt nttccangg 139

<210> SEQ ID NO 12
<211> LENGTH: 25
<212> TYPE: DNA
<213> ORGANISM: Homo sapiens

<400> SEQUENCE: 12
tcacgccata tgggctcggg gaacc 25

-continued

```
<210> SEQ ID NO 13
<211> LENGTH: 41
<212> TYPE: DNA
<213> ORGANISM: Homo sapiens

<400> SEQUENCE: 13

catccgggta ccttattaca cgaagttctc ttcctcttct g                          41


<210> SEQ ID NO 14
<211> LENGTH: 40
<212> TYPE: DNA
<213> ORGANISM: Homo sapiens

<400> SEQUENCE: 14

catcgcggat ccgccatcat gcgtcccggg gcgccagggc                            40


<210> SEQ ID NO 15
<211> LENGTH: 38
<212> TYPE: DNA
<213> ORGANISM: Homo sapiens

<400> SEQUENCE: 15

catccgggta cctcacacga agttctcttc ctcttctg                              38


<210> SEQ ID NO 16
<211> LENGTH: 40
<212> TYPE: DNA
<213> ORGANISM: Homo sapiens

<400> SEQUENCE: 16

catcgcggat ccgccaccat gcgtcccggg gcgccagggc                            40


<210> SEQ ID NO 17
<211> LENGTH: 35
<212> TYPE: DNA
<213> ORGANISM: Homo sapiens

<400> SEQUENCE: 17

tcaccgctcg agcacgaagt tctcttcctc ttctg                                 35


<210> SEQ ID NO 18
<211> LENGTH: 40
<212> TYPE: DNA
<213> ORGANISM: Homo sapiens

<400> SEQUENCE: 18

catcgcggat ccgccaccat gcgtcccggg gcgccagggc                            40


<210> SEQ ID NO 19
<211> LENGTH: 38
<212> TYPE: DNA
<213> ORGANISM: Homo sapiens

<400> SEQUENCE: 19

catccgggta cctcacacga agttctcttc ctcttctg                              38
```